(12) United States Patent
Most et al.

(10) Patent No.: US 9,453,053 B2
(45) Date of Patent: Sep. 27, 2016

(54) SHORT PEPTIDES FOR ENHANCING MUSCLE FUNCTION

(75) Inventors: Patrick Most, Heidelberg (DE); Mirko Voelkers, Heidelberg (DE); Hugo Katus, Heidelberg (DE); Andrew Remppis, Lüneburg (DE)

(73) Assignee: UNIVERSITAT HEIDELBERG, Heidelberg (DE)

( * ) Notice: Subject to any disclaimer, the term of this patent is extended or adjusted under 35 U.S.C. 154(b) by 73 days.

(21) Appl. No.: 13/880,705

(22) PCT Filed: Oct. 20, 2011

(86) PCT No.: PCT/EP2011/005293
§ 371 (c)(1),
(2), (4) Date: Jul. 15, 2013

(87) PCT Pub. No.: WO2012/052177
PCT Pub. Date: Apr. 26, 2012

(65) Prior Publication Data
US 2013/0288971 A1    Oct. 31, 2013

Related U.S. Application Data

(60) Provisional application No. 61/405,155, filed on Oct. 20, 2010.

(51) Int. Cl.
*A61K 38/00*     (2006.01)
*C07K 14/00*     (2006.01)
*C07K 14/47*     (2006.01)
*A61K 38/17*     (2006.01)

(52) U.S. Cl.
CPC .......... *C07K 14/001* (2013.01); *C07K 14/4728* (2013.01); *A61K 38/1738* (2013.01); *C07K 2319/10* (2013.01)

(58) Field of Classification Search
CPC ...... A61K 38/02; A61K 38/03; A61K 38/04; A61K 38/043–38/38; A61K 38/1738; C07K 14/4728
See application file for complete search history.

(56) References Cited

U.S. PATENT DOCUMENTS

| 7,588,756 | B1 | 9/2009 | Katus et al. | |
| 2008/0096823 | A1* | 4/2008 | Barbut et al. | 514/14 |

FOREIGN PATENT DOCUMENTS

| DE | 19915485 A1 | 10/2000 |
| WO | WO 99/40788 * | 8/1999 |
| WO | WO2004005931 A1 | 1/2004 |
| WO | WO2007071248 A2 | 6/2007 |
| WO | WO2008054713 A2 | 5/2008 |
| WO | WO2010118878 A1 | 10/2010 |

OTHER PUBLICATIONS

National Heart, Lung and Blood Institute, Cardiomyopathy, retrieved online on Feb. 19, 2014 from URL: <https://www.nhlbi.nih.gov/health/health-topics/topics/cm/printall-index.html>, 2014.*
Nationwide Children's, Musclular Dystrophy, retrieved online on Feb. 19, 2014 from URL: <http://www.nationwidechildrens.org/muscular-dystrophy>, 2014.*
Pathirana et al, Insulin-like peptide 3 stimulates testosterone secretion in mouse Leydig cells via cAMP pathway, Regulatory Peptides 178 (2012) 102-106.*
Dawson et al, Solid-phase synthesis of ovine Leydig cell insulin-like peptide ± a putative ovine relaxin?, J. Peptide Res. 53, 1999 / 542-547.*
Teerlink et al, Relaxin for the treatment of patients with acute heart failure (Pre-RELAX-AHF): a multicentre, randomised, placebo-controlled, parallel-group, dose-fi nding phase llb study, Lancet, Apr. 25, 2009;373(9673):1429-39.*
Squire et al, The rational use of b-adrenoceptor blockers in the treatment of heart failure. The changing face of an old therapy, Br J Clin Pharmacol, Jan. 2000;49(1):1-9.*
Tan et al, Structural requirements for the interaction of sheep insulin-like factor 3 with relaxin receptors in rat atria, European Journal of Pharmacology 457 (2002) 153-160.*
Bathgate et al, International Union of Pharmacology LVII: Recommendations for the Nomenclature of Receptors for Relaxin Family Peptides, Pharmacol Rev 58:7-31, 2006.*
Hirose et al, C-Type Natriuretic Peptide Increases Myocardial Contractility and Sinus Rate Mediated by Guanylyl Cyclase-Linked Natriuretic Peptide Receptors in Isolated, Blood-Perfused Dog Heart Preparations, JPET 286:70-76, 1998.*
Phoenix Pharmaceuticals, CNP-22, (retrieved online on Oct. 1, 2014 from URL: <http://www.phoenixpeptide.com/catalog/product_info.php?products_id=4236>).*
Yalcin et al, Chronic treatment with agonists of β2-adrenergic receptors in neuropathic pain (Experimental Neurology 221 (2010) 115-121, available online Oct. 17, 2009).*
Azevedo et al, Nonselective Versus Selective b-Adrenergic Receptor Blockade in Congestive Heart Failure Differential Effects on Sympathetic Activity, Circulation. 2001;104:2194-2199.*

(Continued)

*Primary Examiner* — Marcela M Cordero Garcia
*Assistant Examiner* — Sergio Coffa
(74) *Attorney, Agent, or Firm* — Barnes & Thornburg LLP; Yonghao Hou

(57) ABSTRACT

The present invention relates to shortened peptides comprising a muscle function enhancing amino acid sequence which is derived from the S100 calcium binding protein family. Furthermore, the present invention provides said peptides for medical use, in particular, for treating or preventing disorders associated with muscular malfunction, such as skeletal muscle or cardiac muscle disorders. The present invention also provides a pharmaceutical compositions comprising said peptides and a method for treating or preventing disorders associated with muscular malfunction using said peptides or said pharmaceutical compositions.

27 Claims, 26 Drawing Sheets

(56) References Cited

OTHER PUBLICATIONS

77 Jahrestagung der Deutsche Gesellschaft fur Kardiologie Herz und Kreislaufforschung, Clinical Research in Cardiology, vol. 100, No. S1, Apr. 1, 2011, 1 page.

International Search Report and Written Opinion issued in PCT/EP2011/005293, mailed Mar. 2, 2012, 10 pages.

Rohde, David et al., "S100A1 A Multifaceted Therapeutic Target in Cardiovascular Disease", Journal of Cardiovascular Translational Research, vol. 3, No. 5, Oct. 1, 2012, pp. 525-537.

* cited by examiner

FIGURE 1

SEQ ID NO: 38
S100A1 protein: MGSELETAMETLINVFHAHSGKEGDKVKLSKKELKELLQTELSGFLDAQKDVDAVDKVMKELDENGDGEVDFQEYVVLVAALTVACNNFFWENS
(aa)                 1          10        20        30        40        50        60        70        80        90

EF-Hand                                    EF-Hand

SEQ ID NO: 39
S100A1-ct peptide:                                                                                YVVLVAALTVACNNFFWENS FIGURE 13
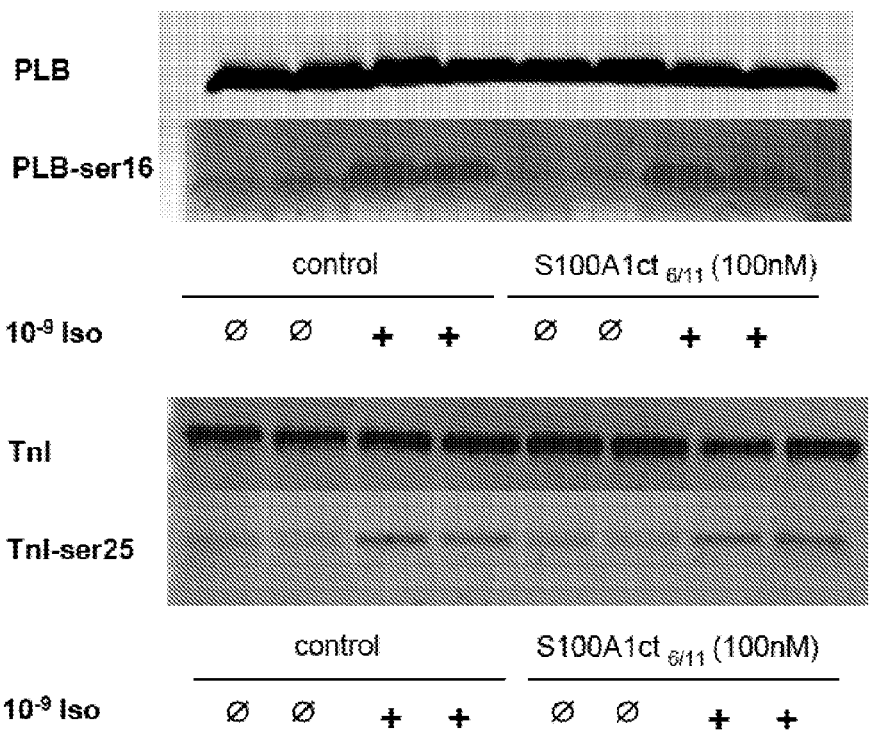
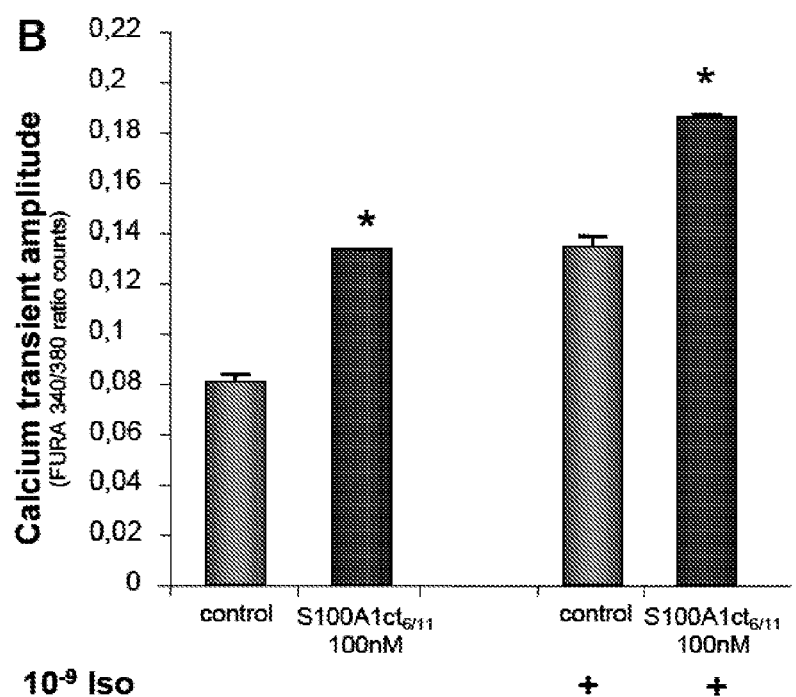

ated with muscular malfunction. For example, cardiac insufficiency, contractile ventricular dysfunction, arrhythmias, heart failure, cardiogenic shock, myocardial infarction, and dysfunction of heart valves have been associated with dysregulation of calcium handling in cardiomyocytes. Analogously, defective calcium cycling in skeletal muscle fibers has been linked with muscular dystrophy (Hopf F. W. et al., 2007, Subcell. Biochem. 45:429-64). Furthermore, mutations in the RyR calcium release channels causing disruption of calcium signaling in muscle cells have been associated with myopathies. In particular, more than 80 mutations have been identified in the skeletal muscle RyR1 calcium release channel and have been linked to malignant hyperthermia, central core disease, or multi-minicore disease. Furthermore, more than 40 mutations in the cardiac RyR2 calcium release channel leading to ventricular arrhythmias and sudden cardiac death have been reported (Dulhunty A. F. et al., 2006, J. Muscle Res. Cell Motil. 27:351-365).

SEQUENCE LISTING

```
<160> NUMBER OF SEQ ID NOS: 418

<210> SEQ ID NO 1
<211> LENGTH: 4
<212> TYPE: PRT
<213> ORGANISM: Artificial Sequence
<220> FEATURE:
<223> OTHER INFORMATION: core motif variants
<220> FEATURE:
<221> NAME/KEY: Variant
<222> LOCATION: (1)..(1)
<223> OTHER INFORMATION: Xaa at position 1 may be valine, isoleucine or
      methionine
<220> FEATURE:
<221> NAME/KEY: Variant
<222> LOCATION: (2)..(2)
<223> OTHER INFORMATION: Xaa at position 2 may be alanine, glycine or
      serine
<220> FEATURE:
<221> NAME/KEY: Variant
<222> LOCATION: (3)..(3)
<223> OTHER INFORMATION: Xaa at position 3 may be alanine or valine

<400> SEQUENCE: 1

Xaa Xaa Xaa Leu
1

<210> SEQ ID NO 2
<211> LENGTH: 10
<212> TYPE: PRT
<213> ORGANISM: Artificial Sequence
<220> FEATURE:
<223> OTHER INFORMATION: variable peptide based on amino acids 76 to 85
      of human S100A1
<220> FEATURE:
<221> NAME/KEY: Variant
<222> LOCATION: (1)..(1)
<223> OTHER INFORMATION: Xaa at position 1 may be valine or isoleucine
<220> FEATURE:
<221> NAME/KEY: Variant
<222> LOCATION: (2)..(2)
<223> OTHER INFORMATION: Xaa at position 2 may be valine 2 or isoleucine
<220> FEATURE:
<221> NAME/KEY: Variant
<222> LOCATION: (3)..(3)
<223> OTHER INFORMATION: Xaa at position 3 may be leucine or methionine
<220> FEATURE:
<221> NAME/KEY: Variant
<222> LOCATION: (4)..(4)
<223> OTHER INFORMATION: Xaa at position 4 may be valine, isoleucine or
      methionine
<220> FEATURE:
```

```
<221> NAME/KEY: Variant
<222> LOCATION: (5)..(5)
<223> OTHER INFORMATION: Xaa at position 5 may be alanine, glycine or
      serine
<220> FEATURE:
<221> NAME/KEY: Variant
<222> LOCATION: (6)..(6)
<223> OTHER INFORMATION: Xaa at position 6 may be alanine or valine
<220> FEATURE:
<221> NAME/KEY: Variant
<222> LOCATION: (8)..(8)
<223> OTHER INFORMATION: Xaa at position 8 may be threonine or alanine
<220> FEATURE:
<221> NAME/KEY: Variant
<222> LOCATION: (9)..(9)
<223> OTHER INFORMATION: Xaa at position 9 may be valine, alanine or
      isoleucine
<220> FEATURE:
<221> NAME/KEY: Variant
<222> LOCATION: (10)..(10)
<223> OTHER INFORMATION: Xaa at position 10 may be alanine, methionine
      or valine

<400> SEQUENCE: 2

Xaa Xaa Xaa Xaa Xaa Xaa Leu Xaa Xaa Xaa
1               5                   10

<210> SEQ ID NO 3
<211> LENGTH: 6
<212> TYPE: PRT
<213> ORGANISM: Artificial Sequence
<220> FEATURE:
<223> OTHER INFORMATION: hydrophilic motif
<220> FEATURE:
<221> NAME/KEY: Variant
<222> LOCATION: (1)..(1)
<223> OTHER INFORMATION: Xaa at position 1 may be aspartic acid or
      glutamic acid
<220> FEATURE:
<221> NAME/KEY: Variant
<222> LOCATION: (2)..(2)
<223> OTHER INFORMATION: Xaa at position 2 may be lysine or arginine
<220> FEATURE:
<221> NAME/KEY: Variant
<222> LOCATION: (3)..(3)
<223> OTHER INFORMATION: Xaa at position 3 may be aspartic acid or
      glutamic acid
<220> FEATURE:
<221> NAME/KEY: Variant
<222> LOCATION: (4)..(4)
<223> OTHER INFORMATION: Xaa at position 4 may be aspartic acid or
      glutamic acid
<220> FEATURE:
<221> NAME/KEY: Variant
<222> LOCATION: (5)..(5)
<223> OTHER INFORMATION: Xaa at position 5 may be proline or glycine
<220> FEATURE:
<221> NAME/KEY: Variant
<222> LOCATION: (6)..(6)
<223> OTHER INFORMATION: Xaa at position 6 may be proline or glycine

<400> SEQUENCE: 3

Xaa Xaa Xaa Xaa Xaa Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: core motif variant

<400> SEQUENCE: 4

Val Gly Ala Leu
```

```
<210> SEQ ID NO 5
<211> LENGTH: 4
<212> TYPE: PRT
<213> ORGANISM: Artificial Sequence
<220> FEATURE:
<223> OTHER INFORMATION: core motif variant

<400> SEQUENCE: 5

Ile Ala Ala Leu
1

<210> SEQ ID NO 6
<211> LENGTH: 4
<212> TYPE: PRT
<213> ORGANISM: Artificial Sequence
<220> FEATURE:
<223> OTHER INFORMATION: core motif variant

<400> SEQUENCE: 6

Val Ser Val Leu
1

<210> SEQ ID NO 7
<211> LENGTH: 4
<212> TYPE: PRT
<213> ORGANISM: Artificial Sequence
<220> FEATURE:
<223> OTHER INFORMATION: core motif variant

<400> SEQUENCE: 7

Met Gly Ala Leu
1

<210> SEQ ID NO 8
<211> LENGTH: 4
<212> TYPE: PRT
<213> ORGANISM: Artificial Sequence
<220> FEATURE:
<223> OTHER INFORMATION: core motif variant

<400> SEQUENCE: 8

Val Ala Ala Leu
1

<210> SEQ ID NO 9
<211> LENGTH: 10
<212> TYPE: PRT
<213> ORGANISM: Artificial Sequence
<220> FEATURE:
<223> OTHER INFORMATION: amino acids 76 to 85 of human S100A1

<400> SEQUENCE: 9

Val Val Leu Val Ala Ala Leu Thr Val Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 10

Val Ile Leu Val Ala Ala Leu Thr Val Ala
```

-continued

```
<210> SEQ ID NO 11
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 11

Val Val Met Val Ala Ala Leu Thr Val Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 12

Ile Ile Leu Val Gly Ala Leu Thr Val Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 13

Val Val Leu Ile Ala Ala Leu Ala Ala Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 14

Val Ile Leu Val Ser Val Leu Thr Val Ala
1               5                   10

<210> SEQ ID NO 15
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 15

Ile Ile Leu Met Gly Ala Leu Thr Val Ala
1               5                   10

<210> SEQ ID NO 16
<211> LENGTH: 10
<212> TYPE: PRT
<213> ORGANISM: Artificial Sequence
<220> FEATURE:
<223> OTHER INFORMATION: peptide variant based on amino acids 76 to 85
``` of human S100A1

<400> SEQUENCE: 16

Val Val Met Val Ala Ala Leu Thr Val Val
1               5                   10

<210> SEQ ID NO 17
<211> LENGTH: 6
<212> TYPE: PRT
<213> ORGANISM: Artificial Sequence
<220> FEATURE:
<223> OTHER INFORMATION: hydrophilic motif

<400> SEQUENCE: 17

Asp Lys Asp Asp Pro Pro
1               5

<210> SEQ ID NO 18
<211> LENGTH: 9
<212> TYPE: PRT
<213> ORGANISM: Artificial Sequence
<220> FEATURE:
<223> OTHER INFORMATION: S100A1 protein derived domain variant

<400> SEQUENCE: 18

Val Val Leu Val Ala Ala Leu Thr Val
1               5

<210> SEQ ID NO 19
<211> LENGTH: 8
<212> TYPE: PRT
<213> ORGANISM: Artificial Sequence
<220> FEATURE:
<223> OTHER INFORMATION: S100A1 protein derived domain variant

<400> SEQUENCE: 19

Val Val Leu Val Ala Ala Leu Thr
1               5

<210> SEQ ID NO 20
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 20

Val Val Leu Val Ala Ala Leu
1               5

<210> SEQ ID NO 21
<211> LENGTH: 9
<212> TYPE: PRT
<213> ORGANISM: Artificial Sequence
<220> FEATURE:
<223> OTHER INFORMATION: S100A1 protein derived domain variant

<400> SEQUENCE: 21

Val Leu Val Ala Ala Leu Thr Val Ala
1               5

<210> SEQ ID NO 22
<211> LENGTH: 8
<212> TYPE: PRT
<213> ORGANISM: Artificial Sequence
<220> FEATURE:
<223> OTHER INFORMATION: S100A1 protein derived domain variant

<400> SEQUENCE: 22

Val Leu Val Ala Ala Leu Thr Val
1               5

<210> SEQ ID NO 23
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 23

Val Leu Val Ala Ala Leu Thr
1               5

<210> SEQ ID NO 24
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 24

Val Leu Val Ala Ala Leu
1               5

<210> SEQ ID NO 25
<211> LENGTH: 8
<212> TYPE: PRT
<213> ORGANISM: Artificial Sequence
<220> FEATURE:
<223> OTHER INFORMATION: S100A1 protein derived domain variant

<400> SEQUENCE: 25

Leu Val Ala Ala Leu Thr Val Ala
1               5

<210> SEQ ID NO 26
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 26

Leu Val Ala Ala Leu Thr Val
1               5

<210> SEQ ID NO 27
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 27

Leu Val Ala Ala Leu Thr
1               5

<210> SEQ ID NO 28
<211> LENGTH: 5
<212> TYPE: PRT
<213> ORGANISM: Artificial Sequence
<220> FEATURE:
<223> OTHER INFORMATION: S100A1 protein derived domain variant

```
<400> SEQUENCE: 28

Leu Val Ala Ala Leu
1               5

<210> SEQ ID NO 29
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 29

Val Ala Ala Leu Thr Val Ala
1               5

<210> SEQ ID NO 30
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 30

Val Ala Ala Leu Thr Val
1               5

<210> SEQ ID NO 31
<211> LENGTH: 5
<212> TYPE: PRT
<213> ORGANISM: Artificial Sequence
<220> FEATURE:
<223> OTHER INFORMATION: S100A1 protein derived domain variant

<400> SEQUENCE: 31

Val Ala Ala Leu Thr
1               5

<210> SEQ ID NO 32
<211> LENGTH: 15
<212> TYPE: PRT
<213> ORGANISM: Artificial Sequence
<220> FEATURE:
<223> OTHER INFORMATION: Functional peptide (Fig. 26)

<400> SEQUENCE: 32

Asp Lys Asp Asp Pro Pro Val Leu Val Ala Ala Leu Thr Val Ala
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: Functional peptide (Fig. 26)

<400> SEQUENCE: 33

Asp Lys Asp Asp Pro Pro Leu Val Ala Ala Leu Thr Val Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Functional peptide (Fig. 26)

<400> SEQUENCE: 34
```

-continued

Asp Lys Asp Asp Pro Val Ala Ala Leu Thr Val Ala
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Functional peptide (Fig. 26)

<400> SEQUENCE: 35

Asp Lys Asp Asp Pro Pro Val Val Leu Val Ala Ala Leu Thr Val
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Functional peptide (Fig. 26)

<400> SEQUENCE: 36

Asp Lys Asp Asp Pro Pro Val Val Leu Val Ala Ala Leu Thr
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Functional peptide (Fig. 26)

<400> SEQUENCE: 37

Asp Lys Asp Asp Pro Pro Val Val Leu Val Ala Ala Leu
1               5                   10

<210> SEQ ID NO 38
<211> LENGTH: 94
<212> TYPE: PRT
<213> ORGANISM: Homo sapiens

<400> SEQUENCE: 38

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Val Asp Ala Val Asp Lys Val Met Lys Glu Leu Asp Glu
        50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90

<210> SEQ ID NO 39
<211> LENGTH: 20
<212> TYPE: PRT
<213> ORGANISM: Artificial Sequence
<220> FEATURE:
<223> OTHER INFORMATION: amino acids 75 to 94 of human S100A1

<400> SEQUENCE: 39

Tyr Val Val Leu Val Ala Ala Leu Thr Val Ala Cys Asn Asn Phe Phe
1               5                   10                  15

Trp Glu Asn Ser
            20

<210> SEQ ID NO 40
<211> LENGTH: 15
<212> TYPE: PRT
<213> ORGANISM: Artificial Sequence
<220> FEATURE:
<223> OTHER INFORMATION: amino acids 2 to 16 of human S100A1

<400> SEQUENCE: 40

Gly Ser Glu Leu Glu Thr Ala Met Glu Thr Leu Ile Asn Val Phe
1               5                   10                  15

<210> SEQ ID NO 41
<211> LENGTH: 13
<212> TYPE: PRT
<213> ORGANISM: Artificial Sequence
<220> FEATURE:
<223> OTHER INFORMATION: amino acids 42 to 54 of human S100A1

<400> SEQUENCE: 41

Leu Ser Gly Phe Leu Asp Ala Gln Lys Asp Val Asp Ala
1               5                   10

<210> SEQ ID NO 42
<211> LENGTH: 17
<212> TYPE: PRT
<213> ORGANISM: Artificial Sequence
<220> FEATURE:
<223> OTHER INFORMATION: amino acids 75 to 85 of human S100A1 fused
      to a hydrophilic motif

<400> SEQUENCE: 42

Asp Lys Asp Asp Pro Pro Tyr Val Val Leu Val Ala Ala Leu Thr Val
1               5                   10                  15

Ala

<210> SEQ ID NO 43
<211> LENGTH: 11
<212> TYPE: PRT
<213> ORGANISM: Artificial Sequence
<220> FEATURE:
<223> OTHER INFORMATION: amino acids 75 to 85 of human S100A1

<400> SEQUENCE: 43

Tyr Val Val Leu Val Ala Ala Leu Thr Val Ala
1               5                   10

<210> SEQ ID NO 44
<211> LENGTH: 12
<212> TYPE: PRT
<213> ORGANISM: Artificial Sequence
<220> FEATURE:
<223> OTHER INFORMATION: amino acids 75 to 80 of human S100A1 fused to
      a hydrophilic motif

<400> SEQUENCE: 44

Asp Lys Asp Asp Pro Pro Tyr Val Val Leu Val Ala
1               5                   10

<210> SEQ ID NO 45
<211> LENGTH: 12
<212> TYPE: PRT

```
<213> ORGANISM: Artificial Sequence
<220> FEATURE:
<223> OTHER INFORMATION: amino acids 80 to 85 of human S100A1 protein
      fused to a hydrophilic motif

<400> SEQUENCE: 45

Asp Lys Asp Asp Pro Pro Ala Ala Leu Thr Val Ala
1               5                   10

<210> SEQ ID NO 46
<211> LENGTH: 17
<212> TYPE: PRT
<213> ORGANISM: Artificial Sequence
<220> FEATURE:
<223> OTHER INFORMATION: amino acids 75 to 85 of S100A4 fused to a
      hydrophilic motif

<400> SEQUENCE: 46

Asp Lys Asp Asp Pro Pro Tyr Cys Val Phe Leu Ser Cys Ile Ala Met
1               5                   10                  15

Met

<210> SEQ ID NO 47
<211> LENGTH: 17
<212> TYPE: PRT
<213> ORGANISM: Artificial Sequence
<220> FEATURE:
<223> OTHER INFORMATION: amino acids 75 to 85 of S100B fused to a
      hydrophilic motif

<400> SEQUENCE: 47

Asp Lys Asp Asp Pro Pro Phe Met Ala Phe Val Ala Met Val Thr Thr
1               5                   10                  15

Ala

<210> SEQ ID NO 48
<211> LENGTH: 6
<212> TYPE: PRT
<213> ORGANISM: Artificial Sequence
<220> FEATURE:
<223> OTHER INFORMATION: hydrophilic motif

<400> SEQUENCE: 48

Glu Lys Asp Asp Pro Pro
1               5

<210> SEQ ID NO 49
<211> LENGTH: 6
<212> TYPE: PRT
<213> ORGANISM: Artificial Sequence
<220> FEATURE:
<223> OTHER INFORMATION: hydrophilic motif

<400> SEQUENCE: 49

Asp Arg Asp Asp Pro Pro
1               5

<210> SEQ ID NO 50
<211> LENGTH: 6
<212> TYPE: PRT
<213> ORGANISM: Artificial Sequence
<220> FEATURE:
<223> OTHER INFORMATION: hydrophilic motif

<400> SEQUENCE: 50

Asp Lys Glu Asp Pro Pro
1               5
```

1               5

<210> SEQ ID NO 51
<211> LENGTH: 6
<212> TYPE: PRT
<213> ORGANISM: Artificial Sequence
<220> FEATURE:
<223> OTHER INFORMATION: hydrophilic motif

<400> SEQUENCE: 51

Asp Lys Asp Glu Pro Pro
1               5

<210> SEQ ID NO 52
<211> LENGTH: 6
<212> TYPE: PRT
<213> ORGANISM: Artificial Sequence
<220> FEATURE:
<223> OTHER INFORMATION: hydrophilic motif

<400> SEQUENCE: 52

Glu Arg Asp Asp Pro Pro
1               5

<210> SEQ ID NO 53
<211> LENGTH: 6
<212> TYPE: PRT
<213> ORGANISM: Artificial Sequence
<220> FEATURE:
<223> OTHER INFORMATION: hydrophilic motif

<400> SEQUENCE: 53

Glu Lys Glu Asp Pro Pro
1               5

<210> SEQ ID NO 54
<211> LENGTH: 6
<212> TYPE: PRT
<213> ORGANISM: Artificial Sequence
<220> FEATURE:
<223> OTHER INFORMATION: hydrophilic motif

<400> SEQUENCE: 54

Glu Lys Asp Glu Pro Pro
1               5

<210> SEQ ID NO 55
<211> LENGTH: 6
<212> TYPE: PRT
<213> ORGANISM: Artificial Sequence
<220> FEATURE:
<223> OTHER INFORMATION: hydrophilic motif

<400> SEQUENCE: 55

Asp Arg Glu Asp Pro Pro
1               5

<210> SEQ ID NO 56
<211> LENGTH: 6
<212> TYPE: PRT
<213> ORGANISM: Artificial Sequence
<220> FEATURE:
<223> OTHER INFORMATION: hydrophilic motif

<400> SEQUENCE: 56

Asp Arg Asp Glu Pro Pro
1               5

<210> SEQ ID NO 57
<211> LENGTH: 6
<212> TYPE: PRT
<213> ORGANISM: Artificial Sequence
<220> FEATURE:
<223> OTHER INFORMATION: hydrophilic motif

<400> SEQUENCE: 57

Asp Lys Glu Glu Pro Pro
1               5

<210> SEQ ID NO 58
<211> LENGTH: 6
<212> TYPE: PRT
<213> ORGANISM: Artificial Sequence
<220> FEATURE:
<223> OTHER INFORMATION: hydrophilic motif

<400> SEQUENCE: 58

Glu Arg Glu Asp Pro Pro
1               5

<210> SEQ ID NO 59
<211> LENGTH: 6
<212> TYPE: PRT
<213> ORGANISM: Artificial Sequence
<220> FEATURE:
<223> OTHER INFORMATION: hydrophilic motif

<400> SEQUENCE: 59

Glu Arg Asp Glu Pro Pro
1               5

<210> SEQ ID NO 60
<211> LENGTH: 6
<212> TYPE: PRT
<213> ORGANISM: Artificial Sequence
<220> FEATURE:
<223> OTHER INFORMATION: hydrophilic motif

<400> SEQUENCE: 60

Asp Arg Glu Glu Pro Pro
1               5

<210> SEQ ID NO 61
<211> LENGTH: 6
<212> TYPE: PRT
<213> ORGANISM: Artificial Sequence
<220> FEATURE:
<223> OTHER INFORMATION: hydrophilic motif

<400> SEQUENCE: 61

Glu Lys Glu Glu Pro Pro
1               5

<210> SEQ ID NO 62
<211> LENGTH: 6
<212> TYPE: PRT
<213> ORGANISM: Artificial Sequence
<220> FEATURE:
<223> OTHER INFORMATION: hydrophilic motif

<400> SEQUENCE: 62

Glu Arg Glu Glu Pro Pro
1               5

```
<210> SEQ ID NO 63
<211> LENGTH: 10
<212> TYPE: PRT
<213> ORGANISM: Artificial Sequence
<220> FEATURE:
<223> OTHER INFORMATION: HIV Tat peptide

<400> SEQUENCE: 63

Gly Arg Lys Lys Arg Arg Gln Arg Arg Arg
1               5                   10

<210> SEQ ID NO 64
<211> LENGTH: 16
<212> TYPE: PRT
<213> ORGANISM: Artificial Sequence
<220> FEATURE:
<223> OTHER INFORMATION: penetratin peptide

<400> SEQUENCE: 64

Arg Gln Ile Lys Ile Trp Phe Gln Asn Arg Arg Met Lys Trp Lys Lys
1               5                   10                  15

<210> SEQ ID NO 65
<211> LENGTH: 17
<212> TYPE: PRT
<213> ORGANISM: Artificial Sequence
<220> FEATURE:
<223> OTHER INFORMATION: penetratin peptide

<400> SEQUENCE: 65

Lys Lys Trp Lys Met Arg Arg Asn Gln Phe Trp Val Lys Val Gln Arg
1               5                   10                  15

Gly

<210> SEQ ID NO 66
<211> LENGTH: 27
<212> TYPE: PRT
<213> ORGANISM: Artificial Sequence
<220> FEATURE:
<223> OTHER INFORMATION: transportan peptide

<400> SEQUENCE: 66

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 67
<211> LENGTH: 27
<212> TYPE: PRT
<213> ORGANISM: Artificial Sequence
<220> FEATURE:
<223> OTHER INFORMATION: MPG/Pep family member peptide

<400> SEQUENCE: 67

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 68
<211> LENGTH: 21
<212> TYPE: PRT
<213> ORGANISM: Artificial Sequence
<220> FEATURE:
```

```
<223> OTHER INFORMATION: MPG/Pep family member peptide

<400> SEQUENCE: 68

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 69
<211> LENGTH: 10
<212> TYPE: PRT
<213> ORGANISM: Artificial Sequence
<220> FEATURE:
<223> OTHER INFORMATION: peptide variant based on amino acids 76 to
      85 of human S100A1

<400> SEQUENCE: 69

Val Val Leu Ile Ala Ala Leu Thr Val Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 70

Val Val Leu Met Ala Ala Leu Thr Val Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 71

Val Val Leu Val Gly Ala Leu Thr Val Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 72

Val Val Leu Val Ser Ala Leu Thr Val Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 73

Val Val Leu Val Ala Val Leu Thr Val Ala
1               5                   10
```

<210> SEQ ID NO 74
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 74

Val Val Leu Val Ala Ala Leu Ala Val Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 75

Val Val Leu Val Ala Ala Leu Thr Ala Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 76

Val Val Leu Val Ala Ala Leu Thr Ile Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 77

Val Val Leu Val Ala Ala Leu Thr Val Met
1               5                   10

<210> SEQ ID NO 78
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 78

Val Val Leu Val Ala Ala Leu Thr Val Val
1               5                   10

<210> SEQ ID NO 79
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 79

Ile Ile Leu Val Ala Ala Leu Thr Val Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 80

Ile Val Met Val Ala Ala Leu Thr Val Ala
1               5                   10

<210> SEQ ID NO 81
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 81

Ile Val Leu Ile Ala Ala Leu Thr Val Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 82

Ile Val Leu Met Ala Ala Leu Thr Val Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 83

Ile Val Leu Val Gly Ala Leu Thr Val Ala
1               5                   10

<210> SEQ ID NO 84
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 84

Ile Val Leu Val Ser Ala Leu Thr Val Ala
1               5                   10

<210> SEQ ID NO 85
<211> LENGTH: 10

```
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 85

Ile Val Leu Val Ala Val Leu Thr Val Ala
1               5                   10

<210> SEQ ID NO 86
<211> LENGTH: 10
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 86

Ile Val Leu Val Ala Ala Leu Ala Val Ala
1               5                   10

<210> SEQ ID NO 87
<211> LENGTH: 10
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 87

Ile Val Leu Val Ala Ala Leu Thr Ala Ala
1               5                   10

<210> SEQ ID NO 88
<211> LENGTH: 10
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 88

Ile Val Leu Val Ala Ala Leu Thr Ile Ala
1               5                   10

<210> SEQ ID NO 89
<211> LENGTH: 10
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 89

Ile Val Leu Val Ala Ala Leu Thr Val Met
1               5                   10

<210> SEQ ID NO 90
<211> LENGTH: 10
<212> TYPE: PRT
<213> ORGANIZM: Artificial Sequence
<220> FEATURE:
<223> OTHER INFORMATION: peptide variant based on amino acids 76 to 85
      of human S100A1

<400> SEQUENCE: 90

Ile Val Leu Val Ala Ala Leu Thr Val Val
```

<210> SEQ ID NO 91
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 91

Val Ile Met Val Ala Ala Leu Thr Val Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 92

Val Ile Leu Ile Ala Ala Leu Thr Val Ala
1               5                   10

<210> SEQ ID NO 93
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 93

Val Ile Leu Met Ala Ala Leu Thr Val Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 94

Val Ile Leu Val Gly Ala Leu Thr Val Ala
1               5                   10

<210> SEQ ID NO 95
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 95

Val Ile Leu Val Ser Ala Leu Thr Val Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: peptide variant based on amino acids 76 to 85 of human S100A1

<400> SEQUENCE: 96

Val Ile Leu Val Ala Val Leu Thr Val Ala
1               5                   10

<210> SEQ ID NO 97
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 97

Val Ile Leu Val Ala Ala Leu Ala Val Ala
1               5                   10

<210> SEQ ID NO 98
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 98

Val Ile Leu Val Ala Ala Leu Thr Ala Ala
1               5                   10

<210> SEQ ID NO 99
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 99

Val Ile Leu Val Ala Ala Leu Thr Ile Ala
1               5                   10

<210> SEQ ID NO 100
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 100

Val Ile Leu Val Ala Ala Leu Thr Val Met
1               5                   10

<210> SEQ ID NO 101
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 101

Val Ile Leu Val Ala Ala Leu Thr Val Val
1               5                   10

<210> SEQ ID NO 102

```
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 102

Val Val Met Ile Ala Ala Leu Thr Val Ala
1               5                   10

<210> SEQ ID NO 103
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 103

Val Val Met Met Ala Ala Leu Thr Val Ala
1               5                   10

<210> SEQ ID NO 104
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 104

Val Val Met Val Gly Ala Leu Thr Val Ala
1               5                   10

<210> SEQ ID NO 105
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 105

Val Val Met Val Ser Ala Leu Thr Val Ala
1               5                   10

<210> SEQ ID NO 106
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 106

Val Val Met Val Ala Val Leu Thr Val Ala
1               5                   10

<210> SEQ ID NO 107
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 107
```

Val Val Met Val Ala Ala Leu Ala Val Ala
1               5                   10

<210> SEQ ID NO 108
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 108

Val Val Met Val Ala Ala Leu Thr Ala Ala
1               5                   10

<210> SEQ ID NO 109
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 109

Val Val Met Val Ala Ala Leu Thr Ile Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 110

Val Val Met Val Ala Ala Leu Thr Val Met
1               5                   10

<210> SEQ ID NO 111
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 111

Val Val Leu Ile Gly Ala Leu Thr Val Ala
1               5                   10

<210> SEQ ID NO 112
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 112

Val Val Leu Ile Ser Ala Leu Thr Val Ala
1               5                   10

<210> SEQ ID NO 113
<211> LENGTH: 10
<212> TYPE: PRT
<213> ORGANISM: Artificial Sequence
<220> FEATURE:

<223> OTHER INFORMATION: peptide variant based on amino acids 76 to 85
     of human S100A1

<400> SEQUENCE: 113

Val Val Leu Ile Ala Val Leu Thr Val Ala
1               5                   10

<210> SEQ ID NO 114
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 114

Val Val Leu Ile Ala Ala Leu Ala Val Ala
1               5                   10

<210> SEQ ID NO 115
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 115

Val Val Leu Ile Ala Ala Leu Thr Ala Ala
1               5                   10

<210> SEQ ID NO 116
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 116

Val Val Leu Ile Ala Ala Leu Thr Ile Ala
1               5                   10

<210> SEQ ID NO 117
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 117

Val Val Leu Ile Ala Ala Leu Thr Val Met
1               5                   10

<210> SEQ ID NO 118
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 118

Val Val Leu Ile Ala Ala Leu Thr Val Val
1               5                   10

```
<210> SEQ ID NO 119
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 119

Val Val Leu Met Gly Ala Leu Thr Val Ala
1               5                   10

<210> SEQ ID NO 120
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 120

Val Val Leu Met Ser Ala Leu Thr Val Ala
1               5                   10

<210> SEQ ID NO 121
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 121

Val Val Leu Met Ala Val Leu Thr Val Ala
1               5                   10

<210> SEQ ID NO 122
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 122

Val Val Leu Met Ala Ala Leu Ala Val Ala
1               5                   10

<210> SEQ ID NO 123
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 123

Val Val Leu Met Ala Ala Leu Thr Ala Ala
1               5                   10

<210> SEQ ID NO 124
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 124
```

Val Val Leu Met Ala Ala Leu Thr Ile Ala
1               5                   10

<210> SEQ ID NO 125
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 125

Val Val Leu Met Ala Ala Leu Thr Val Met
1               5                   10

<210> SEQ ID NO 126
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 126

Val Val Leu Met Ala Ala Leu Thr Val Val
1               5                   10

<210> SEQ ID NO 127
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 127

Val Val Leu Val Gly Val Leu Thr Val Ala
1               5                   10

<210> SEQ ID NO 128
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 128

Val Val Leu Val Gly Ala Leu Ala Val Ala
1               5                   10

<210> SEQ ID NO 129
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 129

Val Val Leu Val Gly Ala Leu Thr Ala Ala
1               5                   10

<210> SEQ ID NO 130
<211> LENGTH: 10
<212> TYPE: PRT
<213> ORGANISM: Artificial Sequence -continued

```
<220> FEATURE:
<223> OTHER INFORMATION: peptide variant based on amino acids 76 to 85
      of human S100A1

<400> SEQUENCE: 130

Val Val Leu Val Gly Ala Leu Thr Ile Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 131

Val Val Leu Val Gly Ala Leu Thr Val Met
1               5                   10

<210> SEQ ID NO 132
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 132

Val Val Leu Val Gly Ala Leu Thr Val Val
1               5                   10

<210> SEQ ID NO 133
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 133

Val Val Leu Val Ser Val Leu Thr Val Ala
1               5                   10

<210> SEQ ID NO 134
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 134

Val Val Leu Val Ser Ala Leu Ala Val Ala
1               5                   10

<210> SEQ ID NO 135
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 135

Val Val Leu Val Ser Ala Leu Thr Ala Ala
1               5                   10
```

<210> SEQ ID NO 136
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 136

Val Val Leu Val Ser Ala Leu Thr Ile Ala
1               5                   10

<210> SEQ ID NO 137
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 137

Val Val Leu Val Ser Ala Leu Thr Val Met
1               5                   10

<210> SEQ ID NO 138
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 138

Val Val Leu Val Ser Ala Leu Thr Val Val
1               5                   10

<210> SEQ ID NO 139
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 139

Val Val Leu Val Ala Val Leu Ala Val Ala
1               5                   10

<210> SEQ ID NO 140
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 140

Val Val Leu Val Ala Val Leu Thr Ala Ala
1               5                   10

<210> SEQ ID NO 141
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 141

Val Val Leu Val Ala Val Leu Thr Ile Ala
1               5                   10

<210> SEQ ID NO 142
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 142

Val Val Leu Val Ala Val Leu Thr Val Met
1               5                   10

<210> SEQ ID NO 143
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 143

Val Val Leu Val Ala Val Leu Thr Val Val
1               5                   10

<210> SEQ ID NO 144
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 144

Val Val Leu Val Ala Ala Leu Ala Ala Ala
1               5                   10

<210> SEQ ID NO 145
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 145

Val Val Leu Val Ala Ala Leu Ala Ile Ala
1               5                   10

<210> SEQ ID NO 146
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 146

Val Val Leu Val Ala Ala Leu Ala Val Met
1               5                   10

<210> SEQ ID NO 147
<211> LENGTH: 10
<212> TYPE: PRT

```
<213> ORGANISM: Artificial Sequence
<220> FEATURE:
<223> OTHER INFORMATION: peptide variant based on amino acids 76 to 85
      of human S100A1

<400> SEQUENCE: 147

Val Val Leu Val Ala Ala Leu Ala Val Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 148

Val Val Leu Val Ala Ala Leu Thr Ala Met
1               5                   10

<210> SEQ ID NO 149
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 149

Val Val Leu Val Ala Ala Leu Thr Ala Val
1               5                   10

<210> SEQ ID NO 150
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 150

Val Val Leu Val Ala Ala Leu Thr Ile Met
1               5                   10

<210> SEQ ID NO 151
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 151

Val Val Leu Val Ala Ala Leu Thr Ile Val
1               5                   10

<210> SEQ ID NO 152
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 152

Ile Ile Met Val Ala Ala Leu Thr Val Ala
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 153

Ile Ile Leu Ile Ala Ala Leu Thr Val Ala
1               5                   10

<210> SEQ ID NO 154
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 154

Ile Ile Leu Met Ala Ala Leu Thr Val Ala
1               5                   10

<210> SEQ ID NO 155
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 155

Ile Ile Leu Val Ser Ala Leu Thr Val Ala
1               5                   10

<210> SEQ ID NO 156
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 156

Ile Ile Leu Val Ala Val Leu Thr Val Ala
1               5                   10

<210> SEQ ID NO 157
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 157

Ile Ile Leu Val Ala Ala Leu Ala Val Ala
1               5                   10

<210> SEQ ID NO 158
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

-continued

<400> SEQUENCE: 158

Ile Ile Leu Val Ala Ala Leu Thr Ala Ala
1               5                   10

<210> SEQ ID NO 159
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 159

Ile Ile Leu Val Ala Ala Leu Thr Ile Ala
1               5                   10

<210> SEQ ID NO 160
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 160

Ile Ile Leu Val Ala Ala Leu Thr Val Met
1               5                   10

<210> SEQ ID NO 161
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 161

Ile Ile Leu Val Ala Ala Leu Thr Val Val
1               5                   10

<210> SEQ ID NO 162
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 162

Ile Val Met Ile Ala Ala Leu Thr Val Ala
1               5                   10

<210> SEQ ID NO 163
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 163

Ile Val Met Met Ala Ala Leu Thr Val Ala
1               5                   10

<210> SEQ ID NO 164
<211> LENGTH: 10

```
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 164

Ile Val Met Val Gly Ala Leu Thr Val Ala
1               5                   10

<210> SEQ ID NO 165
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 165

Ile Val Met Val Ser Ala Leu Thr Val Ala
1               5                   10

<210> SEQ ID NO 166
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 166

Ile Val Met Val Ala Val Leu Thr Val Ala
1               5                   10

<210> SEQ ID NO 167
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 167

Ile Val Met Val Ala Ala Leu Ala Val Ala
1               5                   10

<210> SEQ ID NO 168
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 168

Ile Val Met Val Ala Ala Leu Thr Ala Ala
1               5                   10

<210> SEQ ID NO 169
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 169

Ile Val Met Val Ala Ala Leu Thr Ile Ala
```

```
1               5                   10
```

<210> SEQ ID NO 170
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 170

```
Ile Val Met Val Ala Ala Leu Thr Val Met
1               5                   10
```

<210> SEQ ID NO 171
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 171

```
Ile Val Met Val Ala Ala Leu Thr Val Val
1               5                   10
```

<210> SEQ ID NO 172
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 172

```
Ile Val Leu Ile Gly Ala Leu Thr Val Ala
1               5                   10
```

<210> SEQ ID NO 173
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 173

```
Ile Val Leu Ile Ser Ala Leu Thr Val Ala
1               5                   10
```

<210> SEQ ID NO 174
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 174

```
Ile Val Leu Ile Ala Val Leu Thr Val Ala
1               5                   10
```

<210> SEQ ID NO 175
<211> LENGTH: 10
<212> TYPE: PRT
<213> ORGANISM: Artificial Sequence
<220> FEATURE:
<223> OTHER INFORMATION: peptide variant based on amino acids 76 to 85 of human S100A1

<400> SEQUENCE: 175

Ile Val Leu Ile Ala Ala Leu Ala Val Ala
1               5                   10

<210> SEQ ID NO 176
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 176

Ile Val Leu Ile Ala Ala Leu Thr Ala Ala
1               5                   10

<210> SEQ ID NO 177
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 177

Ile Val Leu Ile Ala Ala Leu Thr Ile Ala
1               5                   10

<210> SEQ ID NO 178
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 178

Ile Val Leu Ile Ala Ala Leu Thr Val Met
1               5                   10

<210> SEQ ID NO 179
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 179

Ile Val Leu Ile Ala Ala Leu Thr Val Val
1               5                   10

<210> SEQ ID NO 180
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 180

Ile Val Leu Met Gly Ala Leu Thr Val Ala
1               5                   10

<210> SEQ ID NO 181

```
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 181

Ile Val Leu Met Ser Ala Leu Thr Val Ala
1               5                   10

<210> SEQ ID NO 182
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 182

Ile Val Leu Met Ala Val Leu Thr Val Ala
1               5                   10

<210> SEQ ID NO 183
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 183

Ile Val Leu Met Ala Ala Leu Ala Val Ala
1               5                   10

<210> SEQ ID NO 184
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 184

Ile Val Leu Met Ala Ala Leu Thr Ala Ala
1               5                   10

<210> SEQ ID NO 185
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 185

Ile Val Leu Met Ala Ala Leu Thr Ile Ala
1               5                   10

<210> SEQ ID NO 186
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 186
```

```
Ile Val Leu Met Ala Ala Leu Thr Val Met
1               5                   10

<210> SEQ ID NO 187
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 187

Ile Val Leu Met Ala Ala Leu Thr Val Val
1               5                   10

<210> SEQ ID NO 188
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 188

Ile Val Leu Val Gly Val Leu Thr Val Ala
1               5                   10

<210> SEQ ID NO 189
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 189

Ile Val Leu Val Gly Ala Leu Ala Val Ala
1               5                   10

<210> SEQ ID NO 190
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 190

Ile Val Leu Val Gly Ala Leu Thr Ala Ala
1               5                   10

<210> SEQ ID NO 191
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 191

Ile Val Leu Val Gly Ala Leu Thr Ile Ala
1               5                   10

<210> SEQ ID NO 192
<211> LENGTH: 10
<212> TYPE: PRT
<213> ORGANISM: Artificial Sequence
<220> FEATURE:
```

```
<223> OTHER INFORMATION: peptide variant based on amino acids 76 to 85
      of human S100A1

<400> SEQUENCE: 192

Ile Val Leu Val Gly Ala Leu Thr Val Met
1               5                   10

<210> SEQ ID NO 193
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 193

Ile Val Leu Val Gly Ala Leu Thr Val Val
1               5                   10

<210> SEQ ID NO 194
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 194

Ile Val Leu Val Ser Val Leu Thr Val Ala
1               5                   10

<210> SEQ ID NO 195
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 195

Ile Val Leu Val Ser Ala Leu Ala Val Ala
1               5                   10

<210> SEQ ID NO 196
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 196

Ile Val Leu Val Ser Ala Leu Thr Ala Ala
1               5                   10

<210> SEQ ID NO 197
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 197

Ile Val Leu Val Ser Ala Leu Thr Ile Ala
1               5                   10
```

```
<210> SEQ ID NO 198
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 198

Ile Val Leu Val Ser Ala Leu Thr Val Met
1               5                   10

<210> SEQ ID NO 199
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 199

Ile Val Leu Val Ser Ala Leu Thr Val Val
1               5                   10

<210> SEQ ID NO 200
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 200

Ile Val Leu Val Ala Val Leu Ala Val Ala
1               5                   10

<210> SEQ ID NO 201
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 201

Ile Val Leu Val Ala Val Leu Thr Ala Ala
1               5                   10

<210> SEQ ID NO 202
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 202

Ile Val Leu Val Ala Val Leu Thr Ile Ala
1               5                   10

<210> SEQ ID NO 203
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 203
```

-continued

Ile Val Leu Val Ala Val Leu Thr Val Met
1               5                   10

<210> SEQ ID NO 204
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 204

Ile Val Leu Val Ala Val Leu Thr Val Val
1               5                   10

<210> SEQ ID NO 205
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 205

Ile Val Leu Val Ala Ala Leu Ala Ala Ala
1               5                   10

<210> SEQ ID NO 206
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 206

Ile Val Leu Val Ala Ala Leu Ala Ile Ala
1               5                   10

<210> SEQ ID NO 207
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 207

Ile Val Leu Val Ala Ala Leu Ala Val Met
1               5                   10

<210> SEQ ID NO 208
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 208

Ile Val Leu Val Ala Ala Leu Ala Val Val
1               5                   10

<210> SEQ ID NO 209
<211> LENGTH: 10
<212> TYPE: PRT
<213> ORGANISM: Artificial Sequence

```
<220> FEATURE:
<223> OTHER INFORMATION: peptide variant based on amino acids 76 to 85
      of human S100A1

<400> SEQUENCE: 209

Ile Val Leu Val Ala Ala Leu Thr Ala Met
1               5                   10

<210> SEQ ID NO 210
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 210

Ile Val Leu Val Ala Ala Leu Thr Ala Val
1               5                   10

<210> SEQ ID NO 211
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 211

Ile Val Leu Val Ala Ala Leu Thr Ile Met
1               5                   10

<210> SEQ ID NO 212
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 212

Ile Val Leu Val Ala Ala Leu Thr Ile Val
1               5                   10

<210> SEQ ID NO 213
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 213

Val Ile Met Ile Ala Ala Leu Thr Val Ala
1               5                   10

<210> SEQ ID NO 214
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 214

Val Ile Met Met Ala Ala Leu Thr Val Ala
1               5                   10
```

```
<210> SEQ ID NO 215
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 215

Val Ile Met Val Gly Ala Leu Thr Val Ala
1               5                   10

<210> SEQ ID NO 216
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 216

Val Ile Met Val Ser Ala Leu Thr Val Ala
1               5                   10

<210> SEQ ID NO 217
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 217

Val Ile Met Val Ala Val Leu Thr Val Ala
1               5                   10

<210> SEQ ID NO 218
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 218

Val Ile Met Val Ala Ala Leu Ala Val Ala
1               5                   10

<210> SEQ ID NO 219
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 219

Val Ile Met Val Ala Ala Leu Thr Ala Ala
1               5                   10

<210> SEQ ID NO 220
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1
```

```
<400> SEQUENCE: 220

Val Ile Met Val Ala Ala Leu Thr Ile Ala
1               5                   10

<210> SEQ ID NO 221
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 221

Val Ile Met Val Ala Ala Leu Thr Val Met
1               5                   10

<210> SEQ ID NO 222
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 222

Val Ile Met Val Ala Ala Leu Thr Val Val
1               5                   10

<210> SEQ ID NO 223
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 223

Val Ile Leu Ile Gly Ala Leu Thr Val Ala
1               5                   10

<210> SEQ ID NO 224
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 224

Val Ile Leu Ile Ser Ala Leu Thr Val Ala
1               5                   10

<210> SEQ ID NO 225
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 225

Val Ile Leu Ile Ala Val Leu Thr Val Ala
1               5                   10

<210> SEQ ID NO 226
<211> LENGTH: 10
<212> TYPE: PRT
```

```
<213> ORGANISM: Artificial Sequence
<220> FEATURE:
<223> OTHER INFORMATION: peptide variant based on amino acids 76 to 85
      of human S100A1

<400> SEQUENCE: 226

Val Ile Leu Ile Ala Ala Leu Ala Val Ala
1               5                   10

<210> SEQ ID NO 227
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 227

Val Ile Leu Ile Ala Ala Leu Thr Ala Ala
1               5                   10

<210> SEQ ID NO 228
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 228

Val Ile Leu Ile Ala Ala Leu Thr Ile Ala
1               5                   10

<210> SEQ ID NO 229
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 229

Val Ile Leu Ile Ala Ala Leu Thr Val Met
1               5                   10

<210> SEQ ID NO 230
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 230

Val Ile Leu Ile Ala Ala Leu Thr Val Val
1               5                   10

<210> SEQ ID NO 231
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 231

Val Ile Leu Met Gly Ala Leu Thr Val Ala
1               5                   10
```

<210> SEQ ID NO 232
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 232

Val Ile Leu Met Ser Ala Leu Thr Val Ala
1               5                   10

<210> SEQ ID NO 233
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 233

Val Ile Leu Met Ala Val Leu Thr Val Ala
1               5                   10

<210> SEQ ID NO 234
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 234

Val Ile Leu Met Ala Ala Leu Ala Val Ala
1               5                   10

<210> SEQ ID NO 235
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 235

Val Ile Leu Met Ala Ala Leu Thr Ala Ala
1               5                   10

<210> SEQ ID NO 236
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 236

Val Ile Leu Met Ala Ala Leu Thr Ile Ala
1               5                   10

<210> SEQ ID NO 237
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

```
<400> SEQUENCE: 237

Val Ile Leu Met Ala Ala Leu Thr Val Met
1               5                   10

<210> SEQ ID NO 238
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 238

Val Ile Leu Met Ala Ala Leu Thr Val Val
1               5                   10

<210> SEQ ID NO 239
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 239

Val Ile Leu Val Gly Val Leu Thr Val Ala
1               5                   10

<210> SEQ ID NO 240
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 240

Val Ile Leu Val Gly Ala Leu Ala Val Ala
1               5                   10

<210> SEQ ID NO 241
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 241

Val Ile Leu Val Gly Ala Leu Thr Ala Ala
1               5                   10

<210> SEQ ID NO 242
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 242

Val Ile Leu Val Gly Ala Leu Thr Ile Ala
1               5                   10

<210> SEQ ID NO 243
<211> LENGTH: 10
```

```
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 243

Val Ile Leu Val Gly Ala Leu Thr Val Met
1               5                   10

<210> SEQ ID NO 244
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 244

Val Ile Leu Val Gly Ala Leu Thr Val Val
1               5                   10

<210> SEQ ID NO 245
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 245

Val Ile Leu Val Ser Ala Leu Ala Val Ala
1               5                   10

<210> SEQ ID NO 246
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 246

Val Ile Leu Val Ser Ala Leu Thr Ala Ala
1               5                   10

<210> SEQ ID NO 247
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 247

Val Ile Leu Val Ser Ala Leu Thr Ile Ala
1               5                   10

<210> SEQ ID NO 248
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 248

Val Ile Leu Val Ser Ala Leu Thr Val Met
```

-continued

```
1               5                   10

<210> SEQ ID NO 249
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 249

Val Ile Leu Val Ser Ala Leu Thr Val Val
1               5                   10

<210> SEQ ID NO 250
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 250

Val Ile Leu Val Ala Val Leu Ala Val Ala
1               5                   10

<210> SEQ ID NO 251
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 251

Val Ile Leu Val Ala Val Leu Thr Ala Ala
1               5                   10

<210> SEQ ID NO 252
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 252

Val Ile Leu Val Ala Val Leu Thr Ile Ala
1               5                   10

<210> SEQ ID NO 253
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 253

Val Ile Leu Val Ala Val Leu Thr Val Met
1               5                   10

<210> SEQ ID NO 254
<211> LENGTH: 10
<212> TYPE: PRT
<213> ORGANISM: Artificial Sequence
<220> FEATURE:
<223> OTHER INFORMATION: peptide variant based on amino acids 76 to 85
``` of human S100A1

<400> SEQUENCE: 254

Val Ile Leu Val Ala Val Leu Thr Val Val
1               5                   10

<210> SEQ ID NO 255
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 255

Val Ile Leu Val Ala Ala Leu Ala Ala Ala
1               5                   10

<210> SEQ ID NO 256
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 256

Val Ile Leu Val Ala Ala Leu Ala Ile Ala
1               5                   10

<210> SEQ ID NO 257
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 257

Val Ile Leu Val Ala Ala Leu Ala Val Met
1               5                   10

<210> SEQ ID NO 258
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 258

Val Ile Leu Val Ala Ala Leu Ala Val Val
1               5                   10

<210> SEQ ID NO 259
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 259

Val Ile Leu Val Ala Ala Leu Thr Ala Met
1               5                   10

<210> SEQ ID NO 260

```
<210> SEQ ID NO 260
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 260

Val Ile Leu Val Ala Ala Leu Thr Ala Val
1               5                   10

<210> SEQ ID NO 261
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 261

Val Ile Leu Val Ala Ala Leu Thr Ile Met
1               5                   10

<210> SEQ ID NO 262
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 262

Val Ile Leu Val Ala Ala Leu Thr Ile Val
1               5                   10

<210> SEQ ID NO 263
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 263

Val Val Met Ile Gly Ala Leu Thr Val Ala
1               5                   10

<210> SEQ ID NO 264
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 264

Val Val Met Ile Ser Ala Leu Thr Val Ala
1               5                   10

<210> SEQ ID NO 265
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 265
```

-continued

Val Val Met Ile Ala Val Leu Thr Val Ala
1               5                   10

<210> SEQ ID NO 266
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 266

Val Val Met Ile Ala Ala Leu Ala Val Ala
1               5                   10

<210> SEQ ID NO 267
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 267

Val Val Met Ile Ala Ala Leu Thr Ala Ala
1               5                   10

<210> SEQ ID NO 268
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 268

Val Val Met Ile Ala Ala Leu Thr Ile Ala
1               5                   10

<210> SEQ ID NO 269
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 269

Val Val Met Ile Ala Ala Leu Thr Val Met
1               5                   10

<210> SEQ ID NO 270
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 270

Val Val Met Ile Ala Ala Leu Thr Val Val
1               5                   10

<210> SEQ ID NO 271
<211> LENGTH: 10
<212> TYPE: PRT
<213> ORGANISM: Artificial Sequence
<220> FEATURE:

<223> OTHER INFORMATION: peptide variant based on amino acids 76 to 85
     of human S100A1

<400> SEQUENCE: 271

Val Val Met Met Gly Ala Leu Thr Val Ala
1               5                   10

<210> SEQ ID NO 272
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 272

Val Val Met Met Ser Ala Leu Thr Val Ala
1               5                   10

<210> SEQ ID NO 273
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 273

Val Val Met Met Ala Val Leu Thr Val Ala
1               5                   10

<210> SEQ ID NO 274
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 274

Val Val Met Met Ala Ala Leu Ala Val Ala
1               5                   10

<210> SEQ ID NO 275
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 275

Val Val Met Met Ala Ala Leu Thr Ala Ala
1               5                   10

<210> SEQ ID NO 276
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 276

Val Val Met Met Ala Ala Leu Thr Ile Ala
1               5                   10

```
<210> SEQ ID NO 277
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 277

Val Val Met Met Ala Ala Leu Thr Val Met
1               5                   10

<210> SEQ ID NO 278
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 278

Val Val Met Met Ala Ala Leu Thr Val Val
1               5                   10

<210> SEQ ID NO 279
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 279

Val Val Met Val Gly Val Leu Thr Val Ala
1               5                   10

<210> SEQ ID NO 280
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 280

Val Val Met Val Gly Ala Leu Ala Val Ala
1               5                   10

<210> SEQ ID NO 281
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 281

Val Val Met Val Gly Ala Leu Thr Ala Ala
1               5                   10

<210> SEQ ID NO 282
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 282
```

```
Val Val Met Val Gly Ala Leu Thr Ile Ala
1               5                   10

<210> SEQ ID NO 283
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 283

Val Val Met Val Gly Ala Leu Thr Val Met
1               5                   10

<210> SEQ ID NO 284
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 284

Val Val Met Val Gly Ala Leu Thr Val Val
1               5                   10

<210> SEQ ID NO 285
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 285

Val Val Met Val Ser Val Leu Thr Val Ala
1               5                   10

<210> SEQ ID NO 286
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 286

Val Val Met Val Ser Ala Leu Ala Val Ala
1               5                   10

<210> SEQ ID NO 287
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 287

Val Val Met Val Ser Ala Leu Thr Ala Ala
1               5                   10

<210> SEQ ID NO 288
<211> LENGTH: 10
<212> TYPE: PRT
<213> ORGANISM: Artificial Sequence
```

```
<220> FEATURE:
<223> OTHER INFORMATION: peptide variant based on amino acids 76 to 85
      of human S100A1

<400> SEQUENCE: 288

Val Val Met Val Ser Ala Leu Thr Ile Ala
1               5                   10

<210> SEQ ID NO 289
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 289

Val Val Met Val Ser Ala Leu Thr Val Met
1               5                   10

<210> SEQ ID NO 290
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 290

Val Val Met Val Ser Ala Leu Thr Val Val
1               5                   10

<210> SEQ ID NO 291
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 291

Val Val Met Val Ala Val Leu Ala Val Ala
1               5                   10

<210> SEQ ID NO 292
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 292

Val Val Met Val Ala Val Leu Thr Ala Ala
1               5                   10

<210> SEQ ID NO 293
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 293

Val Val Met Val Ala Val Leu Thr Ile Ala
1               5                   10
```

```
<210> SEQ ID NO 294
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 294

Val Val Met Val Ala Val Leu Thr Val Met
1               5                   10

<210> SEQ ID NO 295
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 295

Val Val Met Val Ala Val Leu Thr Val Val
1               5                   10

<210> SEQ ID NO 296
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 296

Val Val Met Val Ala Ala Leu Ala Ala Ala
1               5                   10

<210> SEQ ID NO 297
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 297

Val Val Met Val Ala Ala Leu Ala Ile Ala
1               5                   10

<210> SEQ ID NO 298
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 298

Val Val Met Val Ala Ala Leu Ala Val Met
1               5                   10

<210> SEQ ID NO 299
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1
```

```
<400> SEQUENCE: 299

Val Val Met Val Ala Ala Leu Ala Val Val
1               5                   10

<210> SEQ ID NO 300
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 300

Val Val Met Val Ala Ala Leu Thr Ala Met
1               5                   10

<210> SEQ ID NO 301
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 301

Val Val Met Val Ala Ala Leu Thr Ala Val
1               5                   10

<210> SEQ ID NO 302
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 302

Val Val Met Val Ala Ala Leu Thr Ile Met
1               5                   10

<210> SEQ ID NO 303
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 303

Val Val Met Val Ala Ala Leu Thr Ile Val
1               5                   10

<210> SEQ ID NO 304
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 304

Val Val Leu Ile Gly Val Leu Thr Val Ala
1               5                   10

<210> SEQ ID NO 305
<211> LENGTH: 10
<212> TYPE: PRT
```

```
<213> ORGANISM: Artificial Sequence
<220> FEATURE:
<223> OTHER INFORMATION: peptide variant based on amino acids 76 to 85
      of human S100A1

<400> SEQUENCE: 305

Val Val Leu Ile Gly Ala Leu Ala Val Ala
1               5                   10

<210> SEQ ID NO 306
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 306

Val Val Leu Ile Gly Ala Leu Thr Ala Ala
1               5                   10

<210> SEQ ID NO 307
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 307

Val Val Leu Ile Gly Ala Leu Thr Ile Ala
1               5                   10

<210> SEQ ID NO 308
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 308

Val Val Leu Ile Gly Ala Leu Thr Val Met
1               5                   10

<210> SEQ ID NO 309
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 309

Val Val Leu Ile Gly Ala Leu Thr Val Val
1               5                   10

<210> SEQ ID NO 310
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 310

Val Val Leu Ile Ser Val Leu Thr Val Ala
1               5                   10
```

<210> SEQ ID NO 311
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 311

Val Val Leu Ile Ser Ala Leu Ala Val Ala
1               5                   10

<210> SEQ ID NO 312
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 312

Val Val Leu Ile Ser Ala Leu Thr Ala Ala
1               5                   10

<210> SEQ ID NO 313
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 313

Val Val Leu Ile Ser Ala Leu Thr Ile Ala
1               5                   10

<210> SEQ ID NO 314
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 314

Val Val Leu Ile Ser Ala Leu Thr Val Met
1               5                   10

<210> SEQ ID NO 315
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 315

Val Val Leu Ile Ser Ala Leu Thr Val Val
1               5                   10

<210> SEQ ID NO 316
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

-continued

<400> SEQUENCE: 316

Val Val Leu Ile Ala Val Leu Ala Val Ala
1               5                   10

<210> SEQ ID NO 317
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 317

Val Val Leu Ile Ala Val Leu Thr Ala Ala
1               5                   10

<210> SEQ ID NO 318
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 318

Val Val Leu Ile Ala Val Leu Thr Ile Ala
1               5                   10

<210> SEQ ID NO 319
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 319

Val Val Leu Ile Ala Val Leu Thr Val Met
1               5                   10

<210> SEQ ID NO 320
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 320

Val Val Leu Ile Ala Val Leu Thr Val Val
1               5                   10

<210> SEQ ID NO 321
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 321

Val Val Leu Ile Ala Ala Leu Ala Ile Ala
1               5                   10

<210> SEQ ID NO 322
<211> LENGTH: 10

```
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 322

Val Val Leu Ile Ala Ala Leu Ala Val Met
1               5                   10

<210> SEQ ID NO 323
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 323

Val Val Leu Ile Ala Ala Leu Ala Val Val
1               5                   10

<210> SEQ ID NO 324
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 324

Val Val Leu Ile Ala Ala Leu Thr Ala Met
1               5                   10

<210> SEQ ID NO 325
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 325

Val Val Leu Ile Ala Ala Leu Thr Ala Val
1               5                   10

<210> SEQ ID NO 326
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 326

Val Val Leu Ile Ala Ala Leu Thr Ile Met
1               5                   10

<210> SEQ ID NO 327
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 327

Val Val Leu Ile Ala Ala Leu Thr Ile Val
```

-continued

```
1               5                   10

<210> SEQ ID NO 328
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 328

Val Val Leu Met Gly Val Leu Thr Val Ala
1               5                   10

<210> SEQ ID NO 329
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 329

Val Val Leu Met Gly Ala Leu Ala Val Ala
1               5                   10

<210> SEQ ID NO 330
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 330

Val Val Leu Met Gly Ala Leu Thr Ala Ala
1               5                   10

<210> SEQ ID NO 331
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 331

Val Val Leu Met Gly Ala Leu Thr Ile Ala
1               5                   10

<210> SEQ ID NO 332
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 332

Val Val Leu Met Gly Ala Leu Thr Val Met
1               5                   10

<210> SEQ ID NO 333
<211> LENGTH: 10
<212> TYPE: PRT
<213> ORGANISM: Artificial Sequence
<220> FEATURE:
<223> OTHER INFORMATION: peptide variant based on amino acids 76 to 85
``` of human S100A1

<400> SEQUENCE: 333

Val Val Leu Met Gly Ala Leu Thr Val Val
1               5                   10

<210> SEQ ID NO 334
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 334

Val Val Leu Met Ser Val Leu Thr Val Ala
1               5                   10

<210> SEQ ID NO 335
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 335

Val Val Leu Met Ser Ala Leu Ala Val Ala
1               5                   10

<210> SEQ ID NO 336
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 336

Val Val Leu Met Ser Ala Leu Thr Ala Ala
1               5                   10

<210> SEQ ID NO 337
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 337

Val Val Leu Met Ser Ala Leu Thr Ile Ala
1               5                   10

<210> SEQ ID NO 338
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 338

Val Val Leu Met Ser Ala Leu Thr Val Met
1               5                   10

<210> SEQ ID NO 339

```
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 339

Val Val Leu Met Ser Ala Leu Thr Val Val
1               5                   10

<210> SEQ ID NO 340
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 340

Val Val Leu Met Ala Val Leu Ala Val Ala
1               5                   10

<210> SEQ ID NO 341
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 341

Val Val Leu Met Ala Val Leu Thr Ala Ala
1               5                   10

<210> SEQ ID NO 342
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 342

Val Val Leu Met Ala Val Leu Thr Ile Ala
1               5                   10

<210> SEQ ID NO 343
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 343

Val Val Leu Met Ala Val Leu Thr Val Met
1               5                   10

<210> SEQ ID NO 344
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 344
```

```
Val Val Leu Met Ala Val Leu Thr Val Val
1               5                   10

<210> SEQ ID NO 345
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 345

Val Val Leu Met Ala Ala Leu Ala Ala Ala
1               5                   10

<210> SEQ ID NO 346
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 346

Val Val Leu Met Ala Ala Leu Ala Ile Ala
1               5                   10

<210> SEQ ID NO 347
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 347

Val Val Leu Met Ala Ala Leu Ala Val Met
1               5                   10

<210> SEQ ID NO 348
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 348

Val Val Leu Met Ala Ala Leu Ala Val Val
1               5                   10

<210> SEQ ID NO 349
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 349

Val Val Leu Val Gly Val Leu Ala Val Ala
1               5                   10

<210> SEQ ID NO 350
<211> LENGTH: 10
<212> TYPE: PRT
<213> ORGANISM: Artificial Sequence
<220> FEATURE:
```

<223> OTHER INFORMATION: peptide variant based on amino acids 76 to 85
     of human S100A1

<400> SEQUENCE: 350

Val Val Leu Val Gly Val Leu Thr Ala Ala
1               5                   10

<210> SEQ ID NO 351
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 351

Val Val Leu Val Gly Val Leu Thr Ile Ala
1               5                   10

<210> SEQ ID NO 352
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 352

Val Val Leu Val Gly Val Leu Thr Val Met
1               5                   10

<210> SEQ ID NO 353
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 353

Val Val Leu Val Gly Val Leu Thr Val Val
1               5                   10

<210> SEQ ID NO 354
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 354

Val Val Leu Val Gly Ala Leu Ala Ala Ala
1               5                   10

<210> SEQ ID NO 355
<211> LENGTH: 10
<212> TYPE: PRT
<213> ORGANISM: Artificial Sequence
<220> FEATURE:
<223> OTHER INFORMATION: peptide variant based on amino acids 76 to 85
     of human S100A1

<400> SEQUENCE: 355

Val Val Leu Val Gly Ala Leu Ala Ile Ala
1               5                   10

```
<210> SEQ ID NO 356
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 356

Val Val Leu Val Gly Ala Leu Ala Val Met
1               5                   10

<210> SEQ ID NO 357
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 357

Val Val Leu Val Gly Ala Leu Ala Val Val
1               5                   10

<210> SEQ ID NO 358
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 358

Val Val Leu Val Gly Ala Leu Thr Ala Met
1               5                   10

<210> SEQ ID NO 359
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 359

Val Val Leu Val Gly Ala Leu Thr Ala Val
1               5                   10

<210> SEQ ID NO 360
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 360

Val Val Leu Val Gly Ala Leu Thr Ile Met
1               5                   10

<210> SEQ ID NO 361
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 361
```

Val Val Leu Val Gly Ala Leu Thr Ile Val
1               5                   10

<210> SEQ ID NO 362
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 362

Val Val Leu Val Ser Val Leu Ala Val Ala
1               5                   10

<210> SEQ ID NO 363
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 363

Val Val Leu Val Ser Val Leu Thr Ala Ala
1               5                   10

<210> SEQ ID NO 364
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 364

Val Val Leu Val Ser Val Leu Thr Ile Ala
1               5                   10

<210> SEQ ID NO 365
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 365

Val Val Leu Val Ser Val Leu Thr Val Met
1               5                   10

<210> SEQ ID NO 366
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 366

Val Val Leu Val Ser Val Leu Thr Val Val
1               5                   10

<210> SEQ ID NO 367
<211> LENGTH: 10
<212> TYPE: PRT
<213> ORGANISM: Artificial Sequence

```
<220> FEATURE:
<223> OTHER INFORMATION: peptide variant based on amino acids 76 to 85
      of human S100A1

<400> SEQUENCE: 367

Val Val Leu Val Ser Ala Leu Ala Ala Ala
1               5                   10

<210> SEQ ID NO 368
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 368

Val Val Leu Val Ser Ala Leu Ala Ile Ala
1               5                   10

<210> SEQ ID NO 369
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 369

Val Val Leu Val Ser Ala Leu Ala Val Met
1               5                   10

<210> SEQ ID NO 370
<211> LENGTH: 11
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 370

Val Val Leu Val Ser Ala Leu Ala Val Ala Val
1               5                   10

<210> SEQ ID NO 371
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 371

Val Val Leu Val Ser Ala Leu Thr Ala Met
1               5                   10

<210> SEQ ID NO 372
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 372

Val Val Leu Val Ser Ala Leu Thr Ala Val
1               5                   10
```

<210> SEQ ID NO 373
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 373

Val Val Leu Val Ser Ala Leu Thr Ile Met
1               5                   10

<210> SEQ ID NO 374
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 374

Val Val Leu Val Ser Ala Leu Thr Ile Val
1               5                   10

<210> SEQ ID NO 375
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 375

Val Val Leu Val Ala Val Leu Ala Ala Ala
1               5                   10

<210> SEQ ID NO 376
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 376

Val Val Leu Val Ala Val Leu Ala Ile Ala
1               5                   10

<210> SEQ ID NO 377
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 377

Val Val Leu Val Ala Val Leu Ala Val Met
1               5                   10

<210> SEQ ID NO 378
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

-continued

```
<400> SEQUENCE: 378

Val Val Leu Val Ala Val Leu Ala Val Val
1               5                   10

<210> SEQ ID NO 379
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 379

Val Val Leu Val Ala Val Leu Thr Ala Met
1               5                   10

<210> SEQ ID NO 380
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 380

Val Val Leu Val Ala Val Leu Thr Ala Val
1               5                   10

<210> SEQ ID NO 381
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 381

Val Val Leu Val Ala Val Leu Thr Ile Met
1               5                   10

<210> SEQ ID NO 382
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 382

Val Val Leu Val Ala Val Leu Thr Ile Val
1               5                   10

<210> SEQ ID NO 383
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 383

Val Val Leu Val Ala Ala Leu Ala Ala Met
1               5                   10

<210> SEQ ID NO 384
<211> LENGTH: 10
<212> TYPE: PRT
```

```
<213> ORGANISM: Artificial Sequence
<220> FEATURE:
<223> OTHER INFORMATION: peptide variant based on amino acids 76 to 85
      of human S100A1

<400> SEQUENCE: 384

Val Val Leu Val Ala Ala Leu Ala Ala Val
1               5                   10

<210> SEQ ID NO 385
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 385

Val Val Leu Val Ala Ala Leu Ala Ile Met
1               5                   10

<210> SEQ ID NO 386
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 386

Val Val Leu Val Ala Ala Leu Ala Ile Val
1               5                   10

<210> SEQ ID NO 387
<211> LENGTH: 10
<212> TYPE: PRT
<213> ORGANISM: Artificial Sequence
<220> FEATURE:
<223> OTHER INFORMATION: variable peptide based on amino acids 76 to 85
      of human S100A1
<220> FEATURE:
<221> NAME/KEY: Variant
<222> LOCATION: (2)..(2)
<223> OTHER INFORMATION: residue 2 may be valine or isoleucine
<220> FEATURE:
<221> NAME/KEY: Variant
<222> LOCATION: (4)..(4)
<223> OTHER INFORMATION: residue 4 may be valine or isoleucine
<220> FEATURE:
<221> NAME/KEY: Variant
<222> LOCATION: (5)..(5)
<223> OTHER INFORMATION: residue 5 may be alanine or serine
<220> FEATURE:
<221> NAME/KEY: Variant
<222> LOCATION: (6)..(6)
<223> OTHER INFORMATION: residue 6 may be alanine or valine
<220> FEATURE:
<221> NAME/KEY: Variant
<222> LOCATION: (8)..(8)
<223> OTHER INFORMATION: residue 8 may be threonine or alanine
<220> FEATURE:
<221> NAME/KEY: Variant
<222> LOCATION: (9)..(9)
<223> OTHER INFORMATION: residue 9 may be valine or alanine

<400> SEQUENCE: 387

Val Xaa Leu Xaa Xaa Xaa Leu Xaa Xaa Ala
1               5                   10

<210> SEQ ID NO 388
<211> LENGTH: 6
```

```
<212> TYPE: PRT
<213> ORGANISM: Artificial Sequence
<220> FEATURE:
<223> OTHER INFORMATION: amino acids 75 to 80 of human S100A1

<400> SEQUENCE: 388

Tyr Val Val Leu Val Ala
1               5

<210> SEQ ID NO 389
<211> LENGTH: 6
<212> TYPE: PRT
<213> ORGANISM: Artificial Sequence
<220> FEATURE:
<223> OTHER INFORMATION: amino acids 80 to 85 of human S100A1

<400> SEQUENCE: 389

Ala Ala Leu Thr Val Ala
1               5

<210> SEQ ID NO 390
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 390

Val Val Leu Met Ala Ala Leu Thr Ala Met
1               5                   10

<210> SEQ ID NO 391
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 391

Val Val Leu Met Ala Ala Leu Thr Ala Val
1               5                   10

<210> SEQ ID NO 392
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 392

Val Val Leu Met Ala Ala Leu Thr Ile Met
1               5                   10

<210> SEQ ID NO 393
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 393

Val Val Leu Met Ala Ala Leu Thr Ile Val
1               5                   10
```

<210> SEQ ID NO 394
<211> LENGTH: 10
<212> TYPE: PRT
<213> ORGANISM: Artificial Sequence
<220> FEATURE:
<223> OTHER INFORMATION: peptide variant based on amino acids 76 to 85
      of human S100A1

<400> SEQUENCE: 394

Ile Val Leu Val Ala Ala Leu Thr Val Ala
1               5                   10

<210> SEQ ID NO 395
<211> LENGTH: 10
<212> TYPE: PRT
<213> ORGANISM: Artificial sequence
<220> FEATURE:
<223> OTHER INFORMATION: a positive inotropic peptide
<220> FEATURE:
<221> NAME/KEY: variant
<222> LOCATION: (1)..(1)
<223> OTHER INFORMATION: position 1 may be alanine, methionine,
      isoleucine, leucine, or valine
<220> FEATURE:
<221> NAME/KEY: variant
<222> LOCATION: (2)..(2)
<223> OTHER INFORMATION: position 2 may be alanine, methionine,
      isoleucine, leucine, or valine
<220> FEATURE:
<221> NAME/KEY: variant
<222> LOCATION: (3)..(3)
<223> OTHER INFORMATION: position 3 may be alanine, methionine,
      isoleucine, leucine, or valine
<220> FEATURE:
<221> NAME/KEY: variant
<222> LOCATION: (4)..(4)
<223> OTHER INFORMATION: position 4 may be alanine, methionine,
      isoleucine, leucine, or valine
<220> FEATURE:
<221> NAME/KEY: variant
<222> LOCATION: (5)..(5)
<223> OTHER INFORMATION: position 5 may be any amino acid
<220> FEATURE:
<221> NAME/KEY: variant
<222> LOCATION: (6)..(6)
<223> OTHER INFORMATION: position 6 may be alanine, methionine,
      isoleucine, leucine, or valine
<220> FEATURE:
<221> NAME/KEY: variant
<222> LOCATION: (8)..(8)
<223> OTHER INFORMATION: position 1 may be Threonine or Alanine
<220> FEATURE:
<221> NAME/KEY: variant
<222> LOCATION: (8)..(8)
<223> OTHER INFORMATION: position 8 may be Threonine or Alanine
<220> FEATURE:
<221> NAME/KEY: variant
<222> LOCATION: (9)..(9)
<223> OTHER INFORMATION: position 9 may be alanine, methionine,
      isoleucine, leucine, or valine
<220> FEATURE:
<221> NAME/KEY: variant
<222> LOCATION: (10)..(10)
<223> OTHER INFORMATION: position 10 may be alanine, methionine,
      isoleucine, leucine, or valine

<400> SEQUENCE: 395

Xaa Xaa Xaa Xaa Xaa Xaa Leu Xaa Xaa Xaa
1               5                   10

<210> SEQ ID NO 396
<211> LENGTH: 4
<212> TYPE: PRT
<213> ORGANISM: Artificial sequence

```
<220> FEATURE:
<223> OTHER INFORMATION: core motif of an inotropic peptide
<220> FEATURE:
<221> NAME/KEY: variant
<222> LOCATION: (1)..(1)
<223> OTHER INFORMATION: position 1 may be any hydrophobic non-aromatic
      amino acid
<220> FEATURE:
<221> NAME/KEY: variant
<222> LOCATION: (2)..(2)
<223> OTHER INFORMATION: position 2 may be any  amino acid
<220> FEATURE:
<221> NAME/KEY: variant
<222> LOCATION: (3)..(3)
<223> OTHER INFORMATION: position 3 may be any hydrophobic non-aromatic
      amino acid

<400> SEQUENCE: 396

Xaa Xaa Xaa Leu
1

<210> SEQ ID NO 397
<211> LENGTH: 9
<212> TYPE: PRT
<213> ORGANISM: Artificial sequence
<220> FEATURE:
<223> OTHER INFORMATION: a positive inotropic peptide with 9 consecutive
      amino acids
<220> FEATURE:
<221> NAME/KEY: variant
<222> LOCATION: (1)..(1)
<223> OTHER INFORMATION: position 1 may be any hydrophobic non-aromatic
      amino acid
<220> FEATURE:
<221> NAME/KEY: variant
<222> LOCATION: (2)..(2)
<223> OTHER INFORMATION: position 1 may be any hydrophobic non-aromatic
      amino acid
<220> FEATURE:
<221> NAME/KEY: variant
<222> LOCATION: (3)..(3)
<223> OTHER INFORMATION: position 3 may be any hydrophobic non-aromatic
      amino acid
<220> FEATURE:
<221> NAME/KEY: variant
<222> LOCATION: (4)..(4)
<223> OTHER INFORMATION: position 4 may be any hydrophobic non-aromatic
      amino acid
<220> FEATURE:
<221> NAME/KEY: variant
<222> LOCATION: (5)..(5)
<223> OTHER INFORMATION: position 5 may be any amino acid
<220> FEATURE:
<221> NAME/KEY: variant
<222> LOCATION: (6)..(6)
<223> OTHER INFORMATION: position 6 may be any hydrophobic non-aromatic
      amino acid
<220> FEATURE:
<221> NAME/KEY: variant
<222> LOCATION: (8)..(8)
<223> OTHER INFORMATION: position 8 may be Thronine or Alaline
<220> FEATURE:
<221> NAME/KEY: variant
<222> LOCATION: (9)..(9)
<223> OTHER INFORMATION: position 9 may be any hydrophobic non-aromatic
      amino acid

<400> SEQUENCE: 397

Xaa Xaa Xaa Xaa Xaa Xaa Leu Xaa Xaa
1               5

<210> SEQ ID NO 398
<211> LENGTH: 7
<212> TYPE: PRT
<213> ORGANISM: Artificial seqeunce
```

```
<220> FEATURE:
<223> OTHER INFORMATION: S100A1 derived domain consisting of 7
      consecutive amino acids
<220> FEATURE:
<221> NAME/KEY: variant
<222> LOCATION: (1)..(1)
<223> OTHER INFORMATION: Position 1 may be any hydrophobic non-aromatic
      amino acid
<220> FEATURE:
<221> NAME/KEY: variant
<222> LOCATION: (2)..(2)
<223> OTHER INFORMATION: Position 2 may be any hydrophobic non-aromatic
      amino acid
<220> FEATURE:
<221> NAME/KEY: variant
<222> LOCATION: (3)..(3)
<223> OTHER INFORMATION: Position 3 may be any hydrophobic non-aromatic
      amino acid
<220> FEATURE:
<221> NAME/KEY: variant
<222> LOCATION: (4)..(4)
<223> OTHER INFORMATION: Position 4 may be any hydrophobic non-aromatic
      amino acid
<220> FEATURE:
<221> NAME/KEY: variant
<222> LOCATION: (5)..(5)
<223> OTHER INFORMATION: Position 1 may be any  amino acid
<220> FEATURE:
<221> NAME/KEY: variant
<222> LOCATION: (6)..(6)
<223> OTHER INFORMATION: Position 6 may be any hydrophobic non-aromatic
      amino acid

<400> SEQUENCE: 398

Xaa Xaa Xaa Xaa Xaa Xaa Leu
1               5

<210> SEQ ID NO 399
<211> LENGTH: 6
<212> TYPE: PRT
<213> ORGANISM: Artificial sequence
<220> FEATURE:
<223> OTHER INFORMATION: hydrophilic domain within S100A protein
<220> FEATURE:
<221> NAME/KEY: variant
<222> LOCATION: (1)..(4)
<223> OTHER INFORMATION: positions1 to 4 may be any of aspartate,
      glutamate, lysine, or arginine
<220> FEATURE:
<221> NAME/KEY: variant
<222> LOCATION: (5)..(6)
<223> OTHER INFORMATION: positions 5 to 6 may be proline or  glycine

<400> SEQUENCE: 399

Xaa Xaa Xaa Xaa Xaa Xaa
1               5

<210> SEQ ID NO 400
<211> LENGTH: 6
<212> TYPE: PRT
<213> ORGANISM: Artificial sequence
<220> FEATURE:
<223> OTHER INFORMATION: hydrophilic domain of S100A1 protein
<220> FEATURE:
<221> NAME/KEY: variant
<222> LOCATION: (1)..(4)
<223> OTHER INFORMATION: positions 1 to 4 may be aspartate or glutamate
<220> FEATURE:
<221> NAME/KEY: variant
<222> LOCATION: (5)..(6)
<223> OTHER INFORMATION: positions 5 to 6 may be proline or glycine

<400> SEQUENCE: 400

Xaa Xaa Xaa Xaa Xaa Xaa
```

```
1               5
```

<210> SEQ ID NO 401
<211> LENGTH: 6
<212> TYPE: PRT
<213> ORGANISM: Artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: Position 1 may be lysine or arginine
<220> FEATURE:
<221> NAME/KEY: variant
<222> LOCATION: (2)..(4)
<223> OTHER INFORMATION: Position 1 may be aspartate or glutarmate
<220> FEATURE:
<221> NAME/KEY: variant
<222> LOCATION: (5)..(6)
<223> OTHER INFORMATION: Position 1 may be proline or glycine

<400> SEQUENCE: 401

```
Xaa Xaa Xaa Xaa Xaa Xaa
1               5
```

<210> SEQ ID NO 402
<211> LENGTH: 6
<212> TYPE: PRT
<213> ORGANISM: Artificial sequence
<220> FEATURE:
<223> OTHER INFORMATION: hydrophilic petpide of S100A1 protein
<220> FEATURE:
<221> NAME/KEY: variant
<222> LOCATION: (1)..(1)
<223> OTHER INFORMATION: position 1 may be aspartate or glutamate
<220> FEATURE:
<221> NAME/KEY: variant
<222> LOCATION: (2)..(2)
<223> OTHER INFORMATION: position 2 may be lysine or arginine
<220> FEATURE:
<221> NAME/KEY: variant
<222> LOCATION: (3)..(4)
<223> OTHER INFORMATION: positions 3 and 4 may be aspartate or glutamate
<220> FEATURE:
<221> NAME/KEY: variant
<222> LOCATION: (5)..(6)
<223> OTHER INFORMATION: positions 5 and 6 may be proline or glycine

<400> SEQUENCE: 402

```
Xaa Xaa Xaa Xaa Xaa Xaa
1               5
```

<210> SEQ ID NO 403
<211> LENGTH: 6
<212> TYPE: PRT
<213> ORGANISM: Artificial sequence
<220> FEATURE:
<223> OTHER INFORMATION: hydrophilic domain of S100A1 protein
<220> FEATURE:
<221> NAME/KEY: variant
<222> LOCATION: (1)..(2)
<223> OTHER INFORMATION: Positions 1 and 2 may be aspartate or glutamate
<220> FEATURE:
<221> NAME/KEY: variant
<222> LOCATION: (3)..(3)
<223> OTHER INFORMATION: Position 3 may be lysine or arginine
<220> FEATURE:
<221> NAME/KEY: variant
<222> LOCATION: (4)..(4)
<223> OTHER INFORMATION: Position 4 may be aspartate or glutamate
<220> FEATURE:
<221> NAME/KEY: variant
<222> LOCATION: (5)..(6)
<223> OTHER INFORMATION: Positions 5 and 6 may be proline or glycine

```
<400> SEQUENCE: 403

Xaa Xaa Xaa Xaa Xaa Xaa
1               5

<210> SEQ ID NO 404
<211> LENGTH: 6
<212> TYPE: PRT
<213> ORGANISM: Artificial sequence
<220> FEATURE:
<223> OTHER INFORMATION: hydrophilic domain of S100A1
<220> FEATURE:
<221> NAME/KEY: variant
<222> LOCATION: (1)..(3)
<223> OTHER INFORMATION: positions 1-3 may be aspartate or glutamate
<220> FEATURE:
<221> NAME/KEY: variant
<222> LOCATION: (4)..(4)
<223> OTHER INFORMATION: position 4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 404

Xaa Xaa Xaa Xaa Xaa Xaa
1               5

<210> SEQ ID NO 405
<211> LENGTH: 6
<212> TYPE: PRT
<213> ORGANISM: Artificial sequence
<220> FEATURE:
<223> OTHER INFORMATION: hydrophilic domain of S100A1
<220> FEATURE:
<221> NAME/KEY: variant
<222> LOCATION: (1)..(2)
<223> OTHER INFORMATION: positions 1 and 2 may be aspartate or glutamate
<220> FEATURE:
<221> NAME/KEY: variant
<222> LOCATION: (3)..(4)
<223> OTHER INFORMATION: positions 3 and 4 may be lysine or arginine
<220> FEATURE:
<221> NAME/KEY: variant
<222> LOCATION: (5)..(6)
<223> OTHER INFORMATION: positions 5 and 6 may be proline or glycine

<400> SEQUENCE: 405

Xaa Xaa Xaa Xaa Xaa Xaa
1               5

<210> SEQ ID NO 406
<211> LENGTH: 6
<212> TYPE: PRT
<213> ORGANISM: Artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: position 1 may be lysine or arginine
<220> FEATURE:
<221> NAME/KEY: variant
<222> LOCATION: (2)..(2)
<223> OTHER INFORMATION: position 2 may be aspartate or glutamate
<220> FEATURE:
<221> NAME/KEY: variant
<222> LOCATION: (3)..(3)
<223> OTHER INFORMATION: position 3 may be lysine or arginine
<220> FEATURE:
<221> NAME/KEY: variant
<222> LOCATION: (4)..(4)
<223> OTHER INFORMATION: position 4 may be aspartate or glutamate
```

```
<220> FEATURE:
<221> NAME/KEY: variant
<222> LOCATION: (5)..(6)
<223> OTHER INFORMATION: positions 5-6 may be proline or glycine

<400> SEQUENCE: 406

Xaa Xaa Xaa Xaa Xaa Xaa
1               5

<210> SEQ ID NO 407
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: Position 1 may be lysine or arginine
<220> FEATURE:
<221> NAME/KEY: variant
<222> LOCATION: (2)..(3)
<223> OTHER INFORMATION: Positions 2-3 may be aspartate or glutamate
<220> FEATURE:
<221> NAME/KEY: variant
<222> LOCATION: (4)..(4)
<223> OTHER INFORMATION: Position 4 may be lysine or arginine
<220> FEATURE:
<221> NAME/KEY: variant
<222> LOCATION: (5)..(6)
<223> OTHER INFORMATION: Positions 5-6 may be proline or glycine

<400> SEQUENCE: 407

Xaa Xaa Xaa Xaa Xaa Xaa
1               5

<210> SEQ ID NO 408
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: position 1 may be aspartate or glutamate
<220> FEATURE:
<221> NAME/KEY: variant
<222> LOCATION: (2)..(3)
<223> OTHER INFORMATION: positions 2-3 may be lysine or arginine
<220> FEATURE:
<221> NAME/KEY: variant
<222> LOCATION: (4)..(4)
<223> OTHER INFORMATION: position 4 may be aspartate or glutamate
<220> FEATURE:
<221> NAME/KEY: variant
<222> LOCATION: (5)..(6)
<223> OTHER INFORMATION: positions 5-6 may be proline or glycine

<400> SEQUENCE: 408

Xaa Xaa Xaa Xaa Xaa Xaa
1               5

<210> SEQ ID NO 409
<211> LENGTH: 6
<212> TYPE: PRT
<213> ORGANISM: Artificial sequence
<220> FEATURE:
<223> OTHER INFORMATION: hydrophilic domain of S100A1
<220> FEATURE:
<221> NAME/KEY: variant
<222> LOCATION: (1)..(1)
<223> OTHER INFORMATION: position 1 may be aspartate or glutamate
```

```
<220> FEATURE:
<221> NAME/KEY: variant
<222> LOCATION: (2)..(2)
<223> OTHER INFORMATION: position 2 may be lysine or arginine
<220> FEATURE:
<221> NAME/KEY: variant
<222> LOCATION: (3)..(3)
<223> OTHER INFORMATION: position 3 may be aspartate or glutamate
<220> FEATURE:
<221> NAME/KEY: variant
<222> LOCATION: (4)..(4)
<223> OTHER INFORMATION: position 4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 409

Xaa Xaa Xaa Xaa Xaa Xaa
1               5

<210> SEQ ID NO 410
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(2)
<223> OTHER INFORMATION: positions 1 and 2 may be aspartate or glutamate
<220> FEATURE:
<221> NAME/KEY: variant
<222> LOCATION: (3)..(4)
<223> OTHER INFORMATION: positions 3 and 4 may be lysine or arginine
<220> FEATURE:
<221> NAME/KEY: variant
<222> LOCATION: (5)..(6)
<223> OTHER INFORMATION: positions 5 and 6 may be proline or glycine

<400> SEQUENCE: 410

Xaa Xaa Xaa Xaa Xaa Xaa
1               5

<210> SEQ ID NO 411
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(3)
<223> OTHER INFORMATION: positions 1-3 may be lysine or arginine
<220> FEATURE:
<221> NAME/KEY: variant
<222> LOCATION: (4)..(4)
<223> OTHER INFORMATION: position 4 may be aspartate or glutamate
<220> FEATURE:
<221> NAME/KEY: variant
<222> LOCATION: (5)..(6)
<223> OTHER INFORMATION: positions 5-6 may be proline or glycine

<400> SEQUENCE: 411

Xaa Xaa Xaa Xaa Xaa Xaa
1               5

<210> SEQ ID NO 412
<211> LENGTH: 6
<212> TYPE: PRT
<213> ORGANISM: artificial sequence
<220> FEATURE:
<223> OTHER INFORMATION: hydrophilic domain of S100A1 protein
```

```
<220> FEATURE:
<221> NAME/KEY: variant
<222> LOCATION: (1)..(2)
<223> OTHER INFORMATION: positions 1-2 may be lysine or arginine
<220> FEATURE:
<221> NAME/KEY: variant
<222> LOCATION: (3)..(3)
<223> OTHER INFORMATION: position 3 may be aspartate or glutamate
<220> FEATURE:
<221> NAME/KEY: variant
<222> LOCATION: (4)..(4)
<223> OTHER INFORMATION: position 4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 412

Xaa Xaa Xaa Xaa Xaa Xaa
1               5

<210> SEQ ID NO 413
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: position 1 may be lysine or arginine
<220> FEATURE:
<221> NAME/KEY: variant
<222> LOCATION: (2)..(2)
<223> OTHER INFORMATION: position 2 may be aspartate or glutamate
<220> FEATURE:
<221> NAME/KEY: variant
<222> LOCATION: (3)..(4)
<223> OTHER INFORMATION: positions3-4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 413

Xaa Xaa Xaa Xaa Xaa Xaa
1               5

<210> SEQ ID NO 414
<211> LENGTH: 6
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(1)
<223> OTHER INFORMATION: position 1 may be aspartate or glutamate
<220> FEATURE:
<221> NAME/KEY: variant
<222> LOCATION: (2)..(4)
<223> OTHER INFORMATION: positions 2-4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 414

Xaa Xaa Xaa Xaa Xaa Xaa
1               5

<210> SEQ ID NO 415
<211> LENGTH: 6
```

```
<212> TYPE: PRT
<213> ORGANISM: artificial sequence
<220> FEATURE:
<223> OTHER INFORMATION: hydrophilic domain of S100A1 protein
<220> FEATURE:
<221> NAME/KEY: variant
<222> LOCATION: (1)..(4)
<223> OTHER INFORMATION: positions 1-4 may be lysine or arginine
<220> FEATURE:
<221> NAME/KEY: variant
<222> LOCATION: (5)..(6)
<223> OTHER INFORMATION: positions 5-6 may be proline or glycine

<400> SEQUENCE: 415

Xaa Xaa Xaa Xaa Xaa Xaa
1               5

<210> SEQ ID NO 416
<211> LENGTH: 10
<212> TYPE: PRT
<213> ORGANISM: artificial sequence
<220> FEATURE:
<223> OTHER INFORMATION: inotropic peptide
<220> FEATURE:
<221> NAME/KEY: variant
<222> LOCATION: (1)..(2)
<223> OTHER INFORMATION: positions 1-2 may be valine or  isoleucine
<220> FEATURE:
<221> NAME/KEY: variant
<222> LOCATION: (3)..(3)
<223> OTHER INFORMATION: position 3 may be leucine or  methionine
<220> FEATURE:
<221> NAME/KEY: variant
<222> LOCATION: (4)..(4)
<223> OTHER INFORMATION: position 4 may be valine, isoleucine or
      methionine
<220> FEATURE:
<221> NAME/KEY: variant
<222> LOCATION: (5)..(5)
<223> OTHER INFORMATION: position 5 may be alaline, glycine or serine
<220> FEATURE:
<221> NAME/KEY: variant
<222> LOCATION: (6)..(6)
<223> OTHER INFORMATION: position 5 may be alaline or valine
<220> FEATURE:
<221> NAME/KEY: variant
<222> LOCATION: (8)..(8)
<223> OTHER INFORMATION: position 8 may be threonine or alaline
<220> FEATURE:
<221> NAME/KEY: variant
<222> LOCATION: (9)..(9)
<223> OTHER INFORMATION: position 9 may be valine, alanine or isoleucine
<220> FEATURE:
<221> NAME/KEY: variant
<222> LOCATION: (10)..(10)
<223> OTHER INFORMATION: position 10 may be alanine, methionine or
      valine

<400> SEQUENCE: 416

Xaa Xaa Xaa Xaa Xaa Xaa Leu Xaa Xaa Xaa
1               5                   10

<210> SEQ ID NO 417
<211> LENGTH: 15
<212> TYPE: PRT
<213> ORGANISM: artificial sequence
<220> FEATURE:
<223> OTHER INFORMATION: hydrophilic motif linked to teh amino
      terminus of the inotropic peptide
<220> FEATURE:
<221> NAME/KEY: variant
<222> LOCATION: (1)..(4)
<223> OTHER INFORMATION: psitions 1-4 may be aspartate, glutamate,
      lysine and arginine
<220> FEATURE:
```

```
<221> NAME/KEY: variant
<222> LOCATION: (5)..(6)
<223> OTHER INFORMATION: psitions 5-6 may be proline or glycine
<220> FEATURE:
<221> NAME/KEY: variant
<222> LOCATION: (7)..(8)
<223> OTHER INFORMATION: psitions 7-8 may be valine or isoleucine
<220> FEATURE:
<221> NAME/KEY: variant
<222> LOCATION: (9)..(9)
<223> OTHER INFORMATION: psition 9 may be leucine or methionine
<220> FEATURE:
<221> NAME/KEY: variant
<222> LOCATION: (10)..(10)
<223> OTHER INFORMATION: psition 10 may be valine, isoleucine or
      methionine
<220> FEATURE:
<221> NAME/KEY: variant
<222> LOCATION: (11)..(11)
<223> OTHER INFORMATION: psition 11 may be alanine, glycine or serine
<220> FEATURE:
<221> NAME/KEY: variant
<222> LOCATION: (12)..(12)
<223> OTHER INFORMATION: psition 12 may be alanine or valine
<220> FEATURE:
<221> NAME/KEY: variant
<222> LOCATION: (14)..(14)
<223> OTHER INFORMATION: psition 14 may be threonine or alanine
<220> FEATURE:
<221> NAME/KEY: variant
<222> LOCATION: (15)..(15)
<223> OTHER INFORMATION: psition 15 may be valine, alanine or
      isoleucine

<400> SEQUENCE: 417

Xaa Xaa Xaa Xaa Xaa Xaa Xaa Xaa Xaa Xaa Xaa Xaa Leu Xaa Xaa
1               5                   10                  15

<210> SEQ ID NO 418
<211> LENGTH: 8
<212> TYPE: PRT
<213> ORGANISM: artificial sequence
<220> FEATURE:
<223> OTHER INFORMATION: S100A1 protien derived domain
<220> FEATURE:
<221> NAME/KEY: variant
<222> LOCATION: (1)..(4)
<223> OTHER INFORMATION: positions 1-4 may be any hydrophobic non-
      aromatic amino acid
<220> FEATURE:
<221> NAME/KEY: variant
<222> LOCATION: (5)..(5)
<223> OTHER INFORMATION: position 5 may be any  amino acid
<220> FEATURE:
<221> NAME/KEY: variant
<222> LOCATION: (6)..(6)
<223> OTHER INFORMATION: position 6 may be any hydrophobic non-
      aromatic amino acid
<220> FEATURE:
<221> NAME/KEY: variant
<222> LOCATION: (8)..(8)
<223> OTHER INFORMATION: position 8 may be threoinine or alanine

<400> SEQUENCE: 418

Xaa Xaa Xaa Xaa Xaa Xaa Leu Xaa
1               5
```

SHORT PEPTIDES FOR ENHANCING MUSCLE FUNCTION

CROSS-REFERENCE TO RELATED APPLICATIONS

This is a national phase application, filed pursuant to 35 U.S.C. §371, of PCT application No. PCT/EP2011/005293, filed on Oct. 20, 2011, which claims the benefit of U.S. provisional application No. 61/405,155, filed on Oct. 20, 2010. The prior applications are incorporated herein by reference in their entirety.

TECHNICAL FIELD OF INVENTION

The present invention relates to shortened peptides comprising a muscle function enhancing amino acid sequence derived from an S100 protein, which can be used for treating or preventing myopathies, in particular for treating or preventing skeletal muscle or cardiac muscle disorders, a pharmaceutical composition comprising said peptide, and a method for treating or preventing such myopathies.

BACKGROUND OF THE INVENTION

Muscle tissue is subdivided into skeletal muscle, cardiac muscle, and smooth muscle tissue and can be considered the biggest organ of a vertebrate. For example, an average adult human male is made up of 40 to 50% skeletal muscle. Skeletal muscle and cardiac muscle belong to the striated muscle tissue and share many functional aspects. For example, the process of excitation-contraction coupling in skeletal muscle cells and cardiac muscle cells (cardiomyocytes) is very similar. Membrane depolarization of the myocytes causes calcium influx via activated voltage-gated L-type calcium channels into the cytoplasm (sarcoplasm) of the myocyte. The rise of the cytoplasmic calcium concentration leads to calcium release from the sarcoplasmic reticulum (SR) by activation of ryanodine receptors (RyR) through the calcium-induced calcium release (CICR) mechanism, and thus, to a further rapid rise of the cytoplasmic calcium concentration. Calcium molecules diffuse through the cytoplasm and bind to contractile proteins such as troponin C which causes contraction of the myocytes. After contraction, calcium is cleared from the cytoplasm by re-uptake of calcium into the sarcoplasmic reticulum mainly by the action of a sarcoplasmic/endoplasmic reticulum calcium ATPase (SERCA). These events are essentially identical in skeletal muscle cells and cardiac muscle cells with minor differences in the isoforms of the involved proteins. For example, while RyR1 is the predominant sarcoplasmic reticulum calcium release channel in skeletal muscle cells, RyR2 is predominant in cardiomyocyte. Similarly, the skeletal muscle sarcoplasmic/endoplasmic reticulum calcium ATPase is SERCA1a, whereas SERCA2a is cardiomyocyte-specific.

Calcium cycling in myocytes is regulated by a plethora of proteins. For example, S100A1 belonging to the S100 protein family (the largest EF-hand calcium-binding protein subfamily) has been reported to interact with both the RyR calcium release channel and SERCA. S100A1 stabilizes RyR in diastole reducing the frequency of calcium sparks and augments calcium release during systole. Furthermore, S100A1 increases SERCA activity during the relaxation phase and it was found to increase contractile function in cardiac muscle as well as skeletal muscle cells. It has been shown that a carboxy-terminal peptide derived from the S100A1 protein mimics the inotropic effect of the full-length S100A1 protein (Most P. et al., 2007, Am. J. Physiol. Regul. Integr. Comp. Physiol. 293:R568-577; Voelkers M. et al., 2007, Cell Calcium 41:135-143).

Defective calcium cycling in myocytes, for example, reduces calcium release from the sarcoplasmic reticulum during contraction, causes aberrant calcium release events, calcium leakage from the sarcoplasmic reticulum, or slowed calcium clearance from the cytoplasm, resulting in a variety of myopathies, i.e., diseases associ At present, there are no clinical inotropic therapies available for skeletal muscle disorders. Approved therapeutics currently available for the inotropic treatment of cardiomyopathies, such as glycoside derivatives, catecholamines, and phosphodiesterase inhibitors, are afflicted with severe side effects such as increased heart rate and life threatening proarrhythmogenic potential. Besides these approved therapeutics, the S100A1 protein has been suggested as therapeutic in cardiomyopathies, since it was shown that myocardial levels of S100A1 are decreased in heart failure and that S100A1 delivery to cardiomyocytes results in an increase of isometric contraction followed by an increase in the amount of calcium pumped into the sarcoplasmic reticulum. However, the administration of S100A1 to a patient with the purpose of treating myopathies requires the delivery route of gene therapy, for example, using viral delivery, with all its well-known side effects and disadvantages (Most P. et al., 2007, Am. J. Physiol. Regul. Integr. Comp. Physiol. 293:R568-577, WO 2008/054713, and Vinge L. E. et al., 2008, Circ. Res. 102:1458-1470).

Therefore, there is an urgent need for novel therapeutics for the inotropic treatment of myopathies, preferably myopathies associated with dysregulation of calcium cycling in muscle cells, which do not exhibit the severe side effects observed for the approved therapeutics and which do not require the high risk delivery route of gene therapy. Regarding skeletal muscle diseases, there is an urgent need for any inotropic therapeutics having the ability to increase the contractile performance of skeletal muscle cells and/or reducing calcium-induced apoptotic cell death in skeletal muscle cells.

A 20 amino acid peptide derived from the calcium binding protein S100 is known to exhibit inotropic effects (Voelkers M. et al., 2007, Cell Calcium 41:135-143). While peptides are considered very useful therapeutic agents, they generally suffer from some drawbacks such as problematic delivery into cells, i.e. cross-membrane transportation, or immunogenic effects. The present inventors surprisingly found that a significantly shortened peptide S100A1Ct$_{6/10}$ comprising amino acids 76-85 of the S100 protein has inotropic effects similar to said 20-mer peptide. Further fragmentation, however, did not yield functional peptides, suggesting that S100A1ct$_{6/10}$ comprises the shortest functional S100A1 fragment (PCT/EP 2010/002343). Very surprisingly in view of this, the present inventors now found that peptides comprising even shorter S100A1 fragments also exhibit inotropic effects and they identified a 4 amino acid core motif derived from S100A1 (amino acids 79-82 of the S100A1 protein) which is minimally required for functionality. Due to the reduced size of these shortened peptides, delivery into cells is facilitated and immunogenic side effects are minimized. When administered parenterally the shortened peptides are useful for the treatment of myopathies, such as cardiac and skeletal muscle disorders, without exhibiting mentionable side effects and without requiring gene therapy. For example, the peptides according to the present invention enhance and restore inotropy in normal and failing myocardium as well as in normal and diseased skeletal muscle, enhance and restore sarcoplasmic reticulum calcium handling, prevent calcium induced apoptotic cell death in myocytes, protect from proarrhythmogenic sarcoplasmic reticulum calcium leak and tachyarrhythmias, and prevent cardiac death due to protection from pump failure and tachyarrhythmias. The peptides of the present invention are particularly useful for enhancing contractile performance of cardiac and skeletal muscle tissue without major side effects.

SUMMARY OF THE INVENTION

In a first aspect, the present invention provides a positive inotropic peptide comprising or consisting of a hydrophilic domain and/or one or more membrane penetration enhancing domains, and a S100A1 protein derived domain, wherein said S100A1 protein derived domain consists of 4 to 9 consecutive amino acids of the inotropic motif:

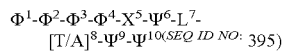
$\Phi^1$-$\Phi^2$-$\Phi^3$-$\Phi^4$-$X^5$-$\Psi^6$-$L^7$-[T/A]$^8$-$\Psi^9$-$\Psi^{10}$(SEQ ID NO: 395)

and comprises at least the core motif $\Phi^4$-$X^5$-$\Psi^6$-$L^7$(SEQ ID NO: 396), wherein $\Phi$ and $\Psi$ are in each instance an independently selected hydrophobic non-aromatic amino acid, and X is any amino acid, and wherein said peptide has a total length of maximally 100 amino acids and the peptide exhibits a positive inotropic action.

In a second aspect, the present invention provides a positive inotropic peptide comprising or consisting of an S100A1 protein derived domain, wherein said S100A1 protein derived domain consists of 7 to 9 consecutive amino acids of the inotropic motif:

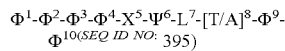
$\Phi^1$-$\Phi^2$-$\Phi^3$-$\Phi^4$-$X^5$-$\Psi^6$-$L^7$-[T/A]$^8$-$\Phi^9$-$\Phi^{10}$(SEQ ID NO: 395)

and comprises at least the core motif $\Phi^4$-$X^5$-$\Psi^6$-$L^7$(SEQ ID NO: 396), wherein $\Phi$ and $\Psi$ are in each instance an independently selected hydrophobic non-aromatic amino acid, and X is any amino acid, under the proviso that the N-terminal amino acid of said S100A protein derived domain consisting of 9 consecutive amino acids is $\Phi^1$, and wherein said peptide has a total length of maximally 100 amino acids.

In a third aspect, the present invention relates to the peptide of the first or the second aspect for medical use.

In a fourth aspect, the present invention provides the peptide of the first or second aspect for therapeutic use in treating or preventing disorders associated with muscular malfunction, wherein preferably the disorder is a cardiac and/or skeletal muscle disorder, wherein preferably the muscular malfunction is associated with defective calcium cycling and/or defective contractile performance in muscle cells. Preferably, the peptide is for enhancing and/or restoring calcium cycling and/or for enhancing and/or restoring contractile performance in muscle cells. The cardiac muscle disorder may be selected from the group consisting of postischemic contractile dysfunction, congestive heart failure, cardiogenic shock, septic shock, myocardial infarction, cardiomyopathy, dysfunction of heart valves, and ventricular disorder, the skeletal muscle disorder may be selected from the group consisting of muscular dystrophy, muscle weakness, muscular atrophy, myositis, central core disease, nemaline rod myopathy, centronuclear myotubular myopathy, ophthalmoplegia of the eye, mitochondrial myopathy.

In a fifth aspect, the present invention provides a pharmaceutical composition comprising the peptide of the first or the second aspect of the present invention and a pharmaceutically acceptable excipient, carrier, and/or diluent. In a preferred embodiment, the pharmaceutical composition is for treating or preventing disorders associated with muscular malfunction.

In a sixth aspect, the present invention provides a method for treating or preventing disorders associated with muscular malfunction comprising administering to an individual in need thereof the peptide or the pharmaceutical composition according to the present invention in an amount sufficient to ameliorate the disease condition of said individual.

In a seventh aspect, the present invention provides a pharmaceutical composition comprising the peptide according to the first or second aspect of the present invention and a medicament selected from the group consisting of catecholamines, β-adrenergic receptor agonists, and β-adrenergic receptor blockers.

BRIEF DESCRIPTION OF THE DRAWINGS

FIG. 1: Characterization of the S100A1 protein C-terminus as the bioactive lead structure. FIG. 1 shows the primary structure of native human S100A1 protein (S100A1, 94 amino acids; SEQ ID NO: 38) in the upper row and the S100A1 C-terminus in the lower row as a 20-mer peptide (S100A1-ct peptide) encompassing amino acids 75-94 (SEQ ID NO: 39) devoid of the C-terminal calcium binding EF-hand.

The S100A1 C-terminal domain encompassing amino acids 75-94 is the most hydrophobic region of the protein. The Kyte-Doolittle Plot was performed by the inventors with the published cDNA sequence of the human s100a1 gene (GenBank accession number: NM006271) employing a hydrophobicity plot accessible at http://www.vivo.colostate.edu/molkit/hydropathy/index.html. A y-axis score>0 depicts increasing hydrophobicity. The S100A1 C-terminus including amino acids 75-94 is marked by a grey bar.

Figure 2:
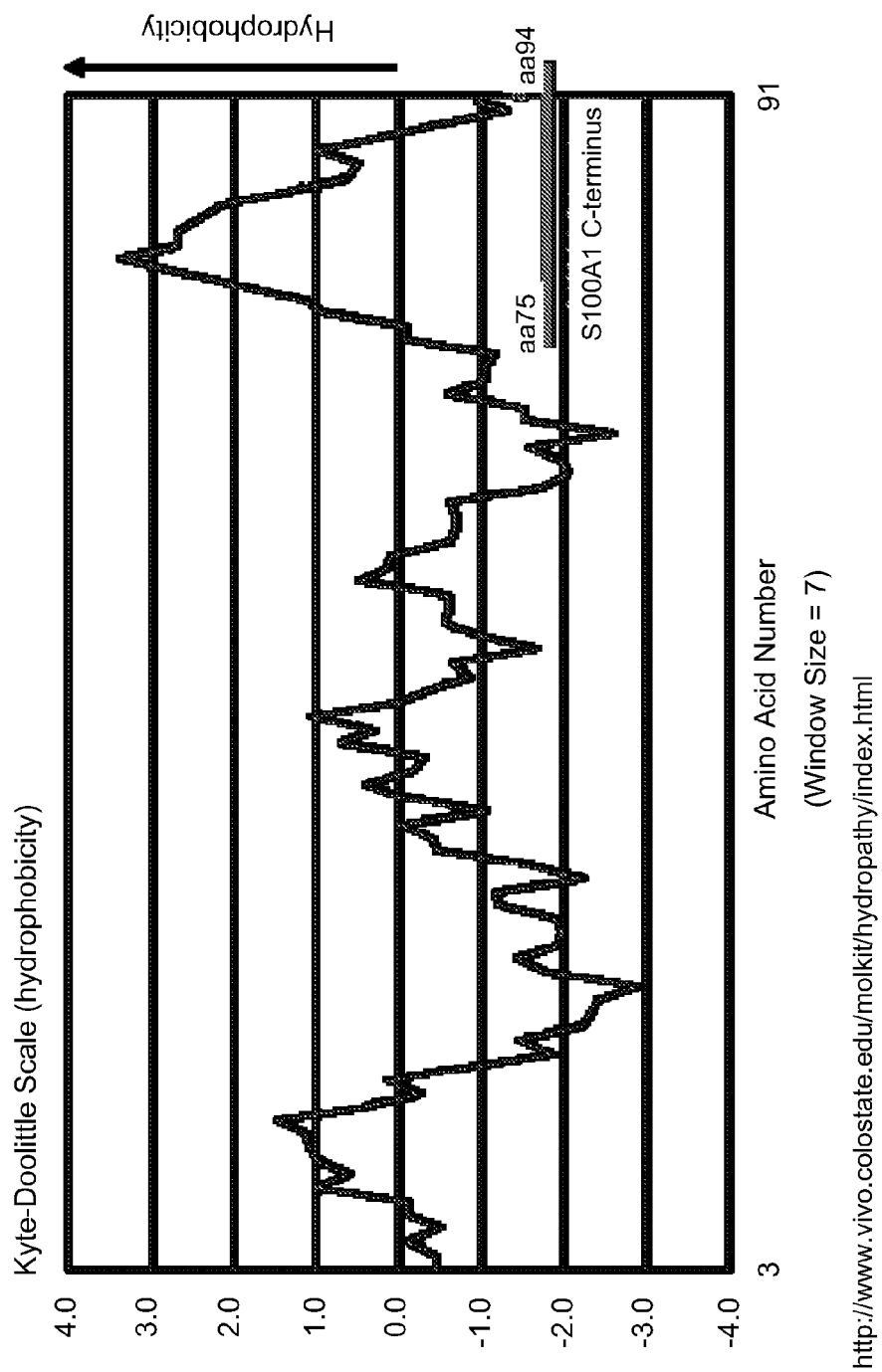
FIG. 2: Hydrophobicity plot of human S100A1.
Figure 3:
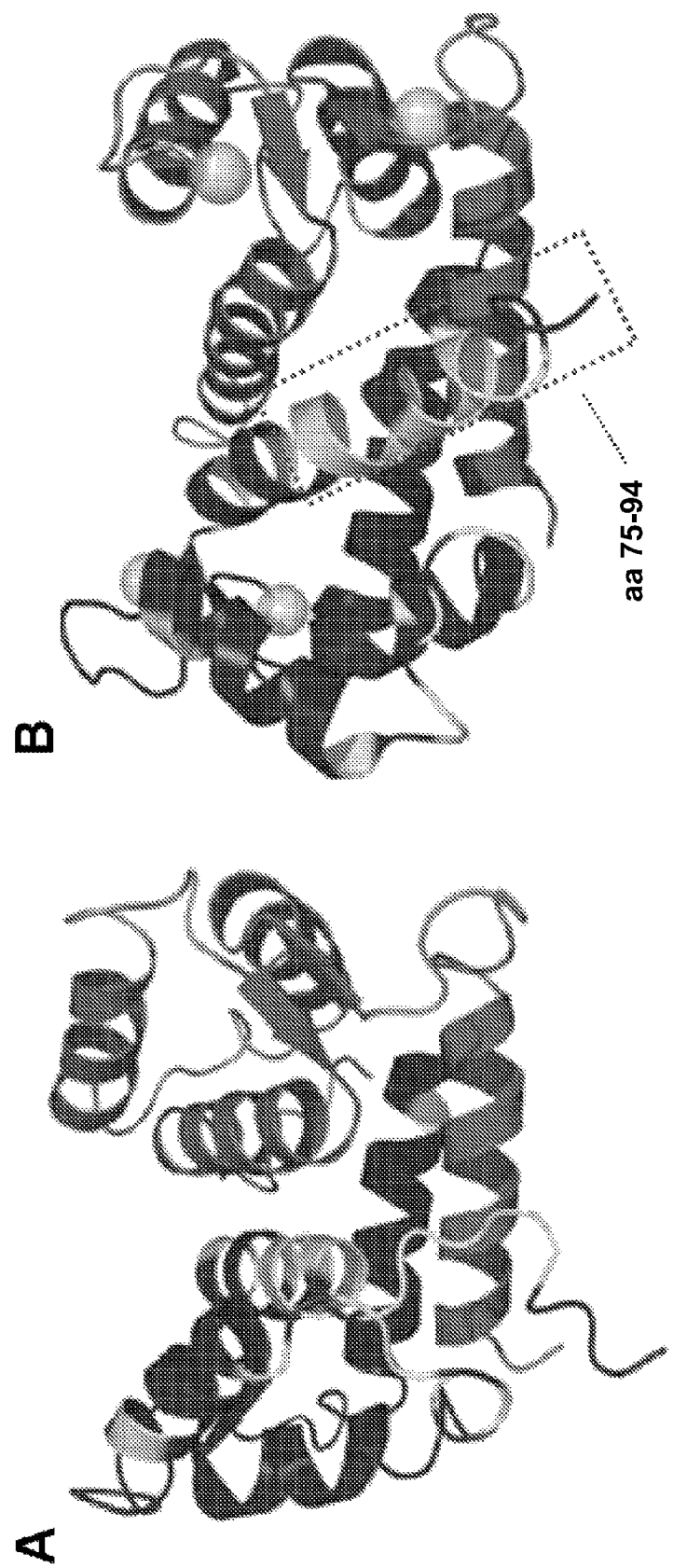

FIG. 3: Tertiary/quaternary structure of human S100A1 protein.

FIG. 3A visualizes the tertiary/quaternary structure of human S100A1 showing that the hydrophobic C-terminus is buried inside the calcium-unbound form and apo-state, respectively, of the homodimeric protein. FIG. 3B shows that calcium binding to both EF-hand motives results in exposure of the S100A1 C-terminus to the molecule surface rendering the hydrophobic domain accessible for protein-protein interactions. It has therefore been suggested that the S100A1 C-terminus including amino acids 75-94 accounts for target protein binding and modulation of target protein function/activity in the calcium-bound and "activated" dimeric S100A1 protein. Calcium binding to S100A1 confers a conformational change rendering the C-terminal domain (amino acids 75-94) (dashed box) accessible for protein-protein interaction.

Figure 4:
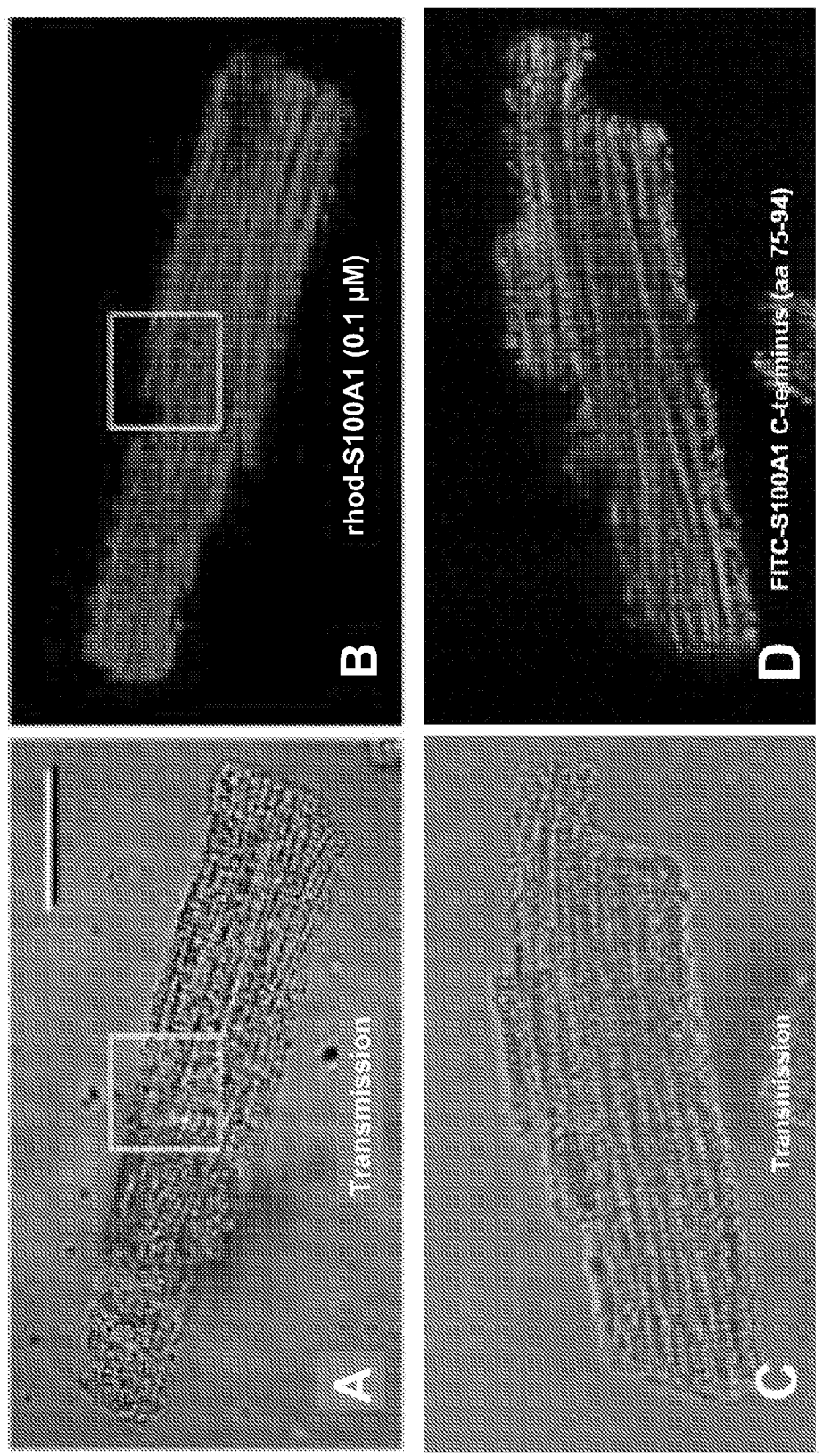

FIG. 4: Human S100A1 protein and the 20-mer C-terminal peptide in chemically permeabilized cardiac and skeletal muscle cell preparations.

Equivalent bioactivity of native human S100A1 protein and the 20-mer C-terminal peptide was shown by the inventors in chemically permeabilized cardiac and skeletal muscle cell preparations enabling intracellular access and regulation of RyR2 and RyR1 function. FIG. 4 depicts a similar intracellular binding pattern for rhodamine-labeled recombinant human S100A1 protein (10415 Mw) (FIG. 4A/B) and the 20-mer FITC-labeled synthetic S100A1 C-terminal peptide (2258 Mw) (FIG. 4C/D). Neither rhod-S100A1 protein nor FITC-S100A1 C-terminus (amino acids 75-94) is able to permeate the cell membrane of adult intact cardiomyocytes.

Figure 5:
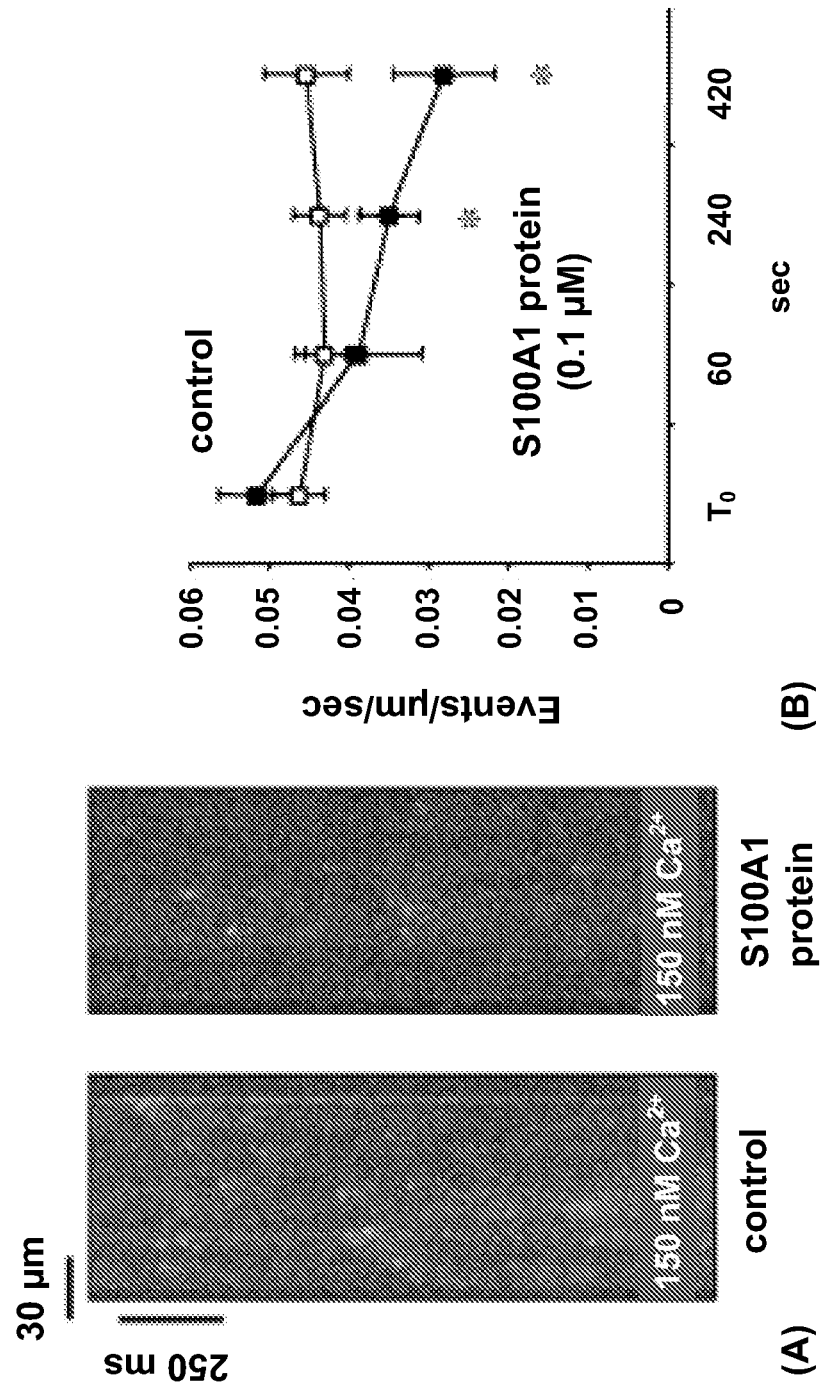

FIG. 5: S100A1 protein decreases diastolic calcium spark frequency and RyR2 activity in permeabilized cardiomyocytes (A) and enhances isometric twitch force in permeabilized skeletal muscle fibers (B). S100A1 protein does not alter calcium homeostasis in adult intact cardiomyocytes or skeletal muscle fibers.

Figure 6:
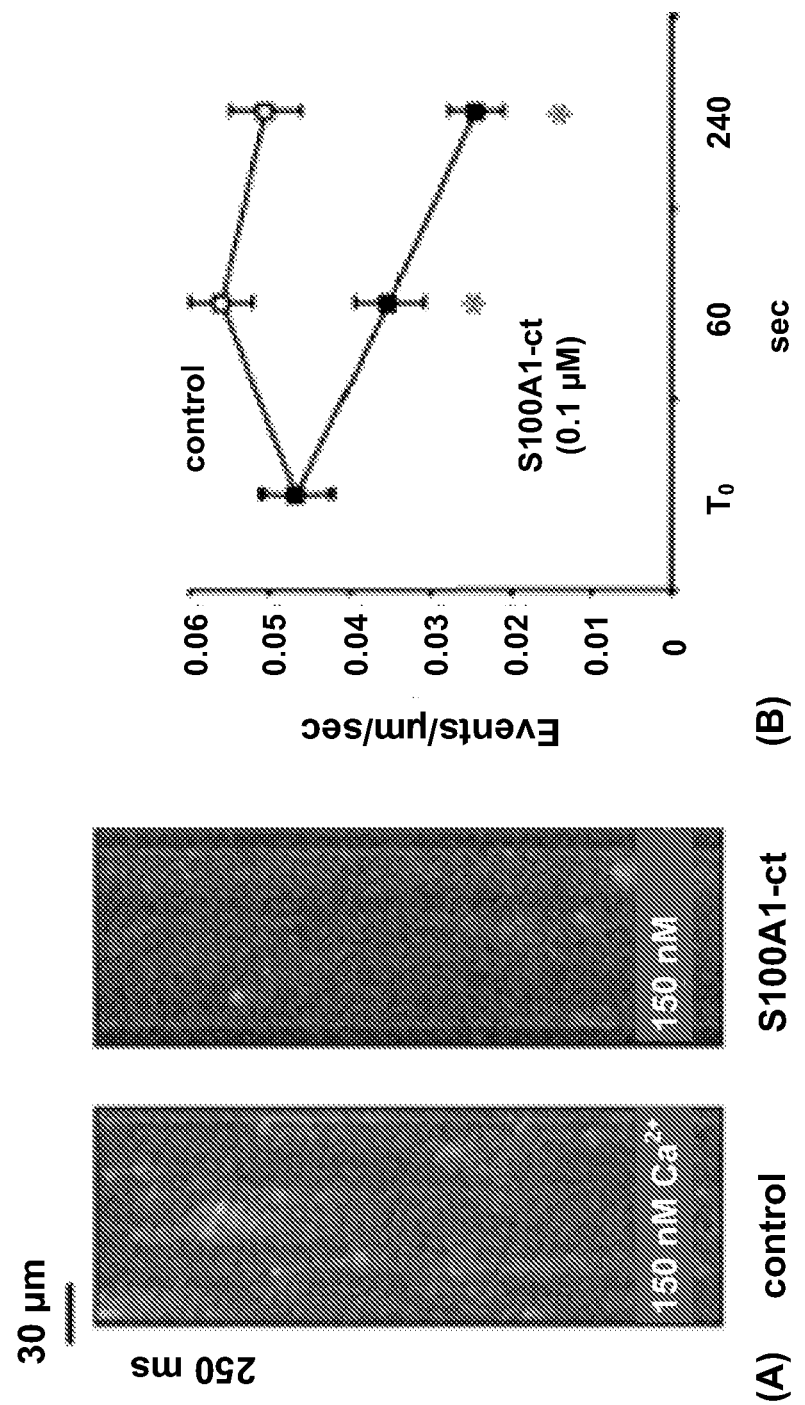

FIG. 6: The 20-mer S100A1 C-terminal peptide (amino acids 75 to 94 of the S100A1 protein) decreases diastolic calcium spark frequency and RyR2 activity in permeabilized cardiomyocytes (A) and enhances isometric twitch force in permeabilized skeletal muscle fibers (B), but does not alter calcium homeostasis in adult intact cardiomyocytes or skeletal muscle fibers.

Figure 7:
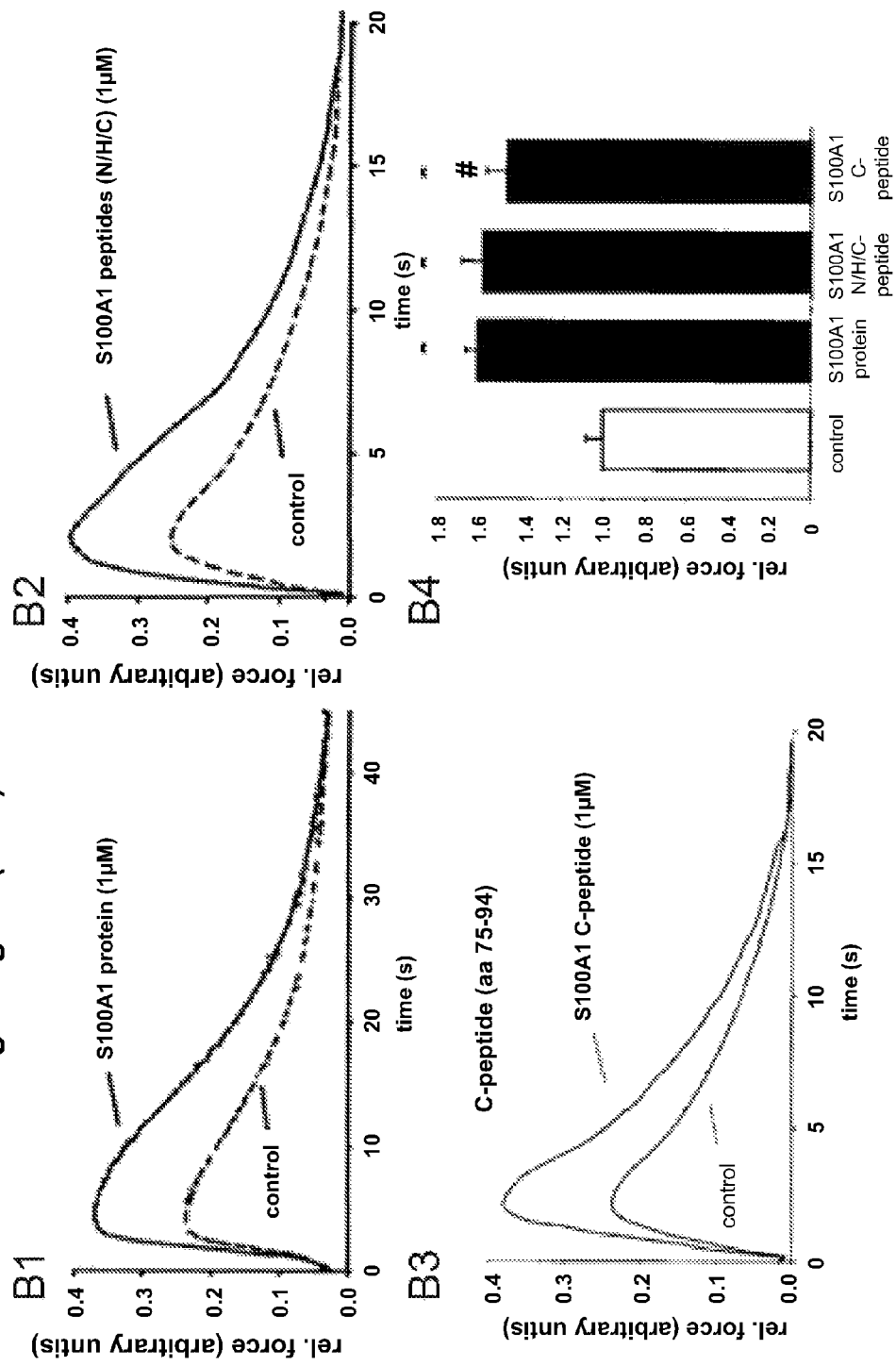

FIG. 7: Both S100A1 protein (B1) and the 20-mer S100A1 C-terminal peptide (B3) have equivalent biological potency to enhance isometric force in permeabilized EDL murine skeletal muscle fibers. B2 and B3 confirm that solely the S100A1 C-terminus mediates the inotropic effect. S100A1 peptides (N/H/C) refer to the N-terminal peptide (N) G-S-E-L-E-T-A-M-E-T-L-I-N-V-F (amino acids 2 to 16 of S100A1, SEQ ID NO: 40), the hinge-region peptide (H) L-S-G-F-L-D-A-Q-K-D-V-D-A (amino acids 42 to 54 of S100A1, SEQ ID NO: 41), and the C-terminal 20-mer (C) (SEQ ID NO: 39).

Figure 8:
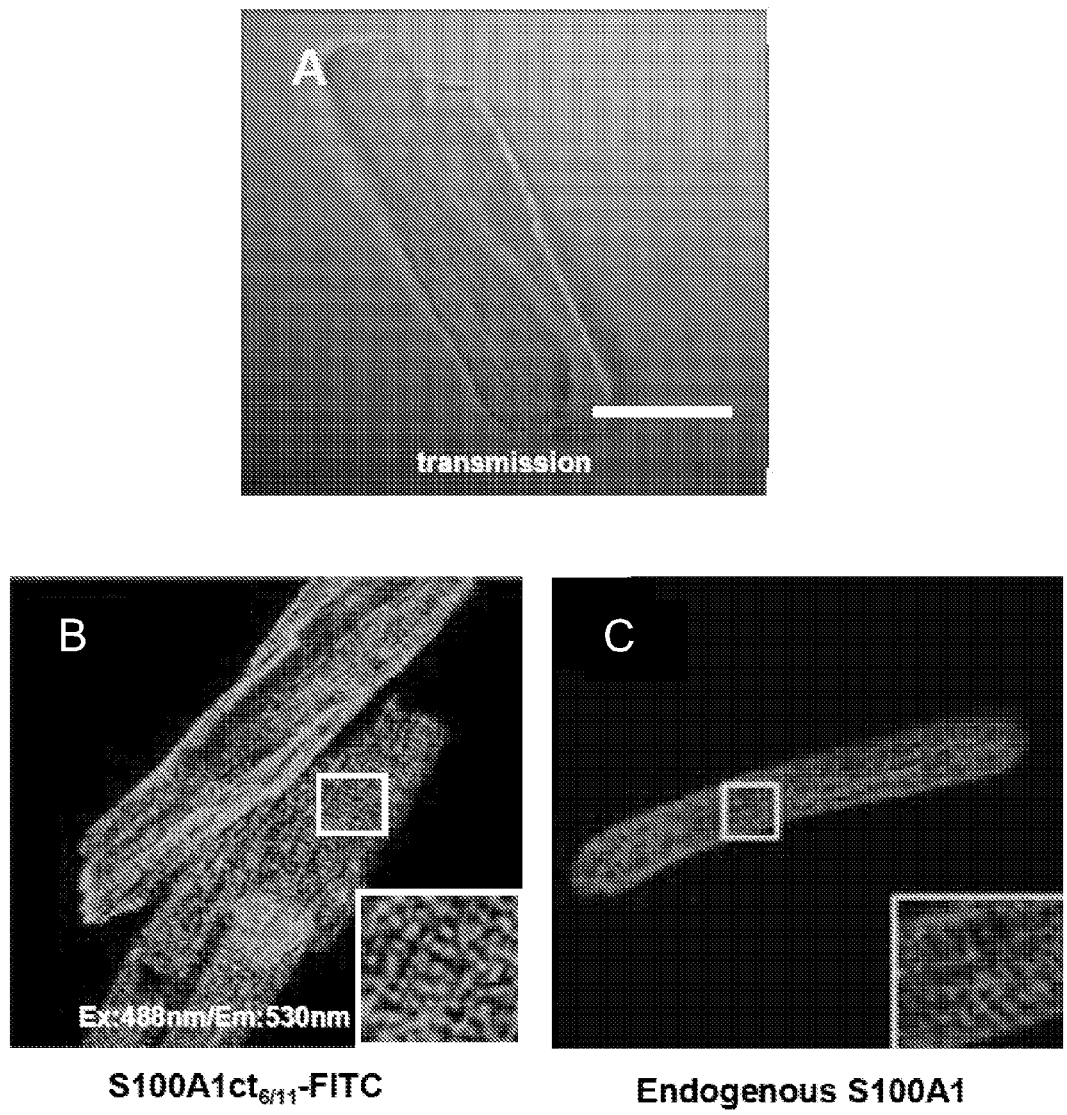

FIG. 8: Cell permeable S100A1ct$_{6/11}$ sequence and intracellular accumulation in normal and diseased cardiomyocytes.

S100A1 ct$_{6/11}$ refers to the peptide D-K-D-D-P-P-Y-V-V-L-V-A-A-L-T-V-A (SEQ ID NO: 42), wherein the sequence D-K-D-D-P-P (SEQ ID NO: 17) is a hydrophilic motif and the sequence Y-V-V-L-V-A-A-L-T-V-A (SEQ ID NO: 43) are amino acids 75 to 85 of the human S100A1 protein. The S100A1ct$_{6/11}$ peptide is cell permeable and accumulates in the intracellular space of cardiomyocytes in contrast to the cell-impermeable 20-mer C-terminal S100A1 peptide. FIG. 8 shows that FITC-coupled S100A1ct$_{6/11}$ enriches in the intracellular space of intact rat ventricular cardiomyocytes resulting in a striated pattern (B, confocal image taken after 15 min of extracellular exposure) similar to endogenous S100A1 protein assessed by anti-S100A1 immunofluorescence staining (C), while the control (A) did not exhibit a specific labeling pattern.

Figure 9:
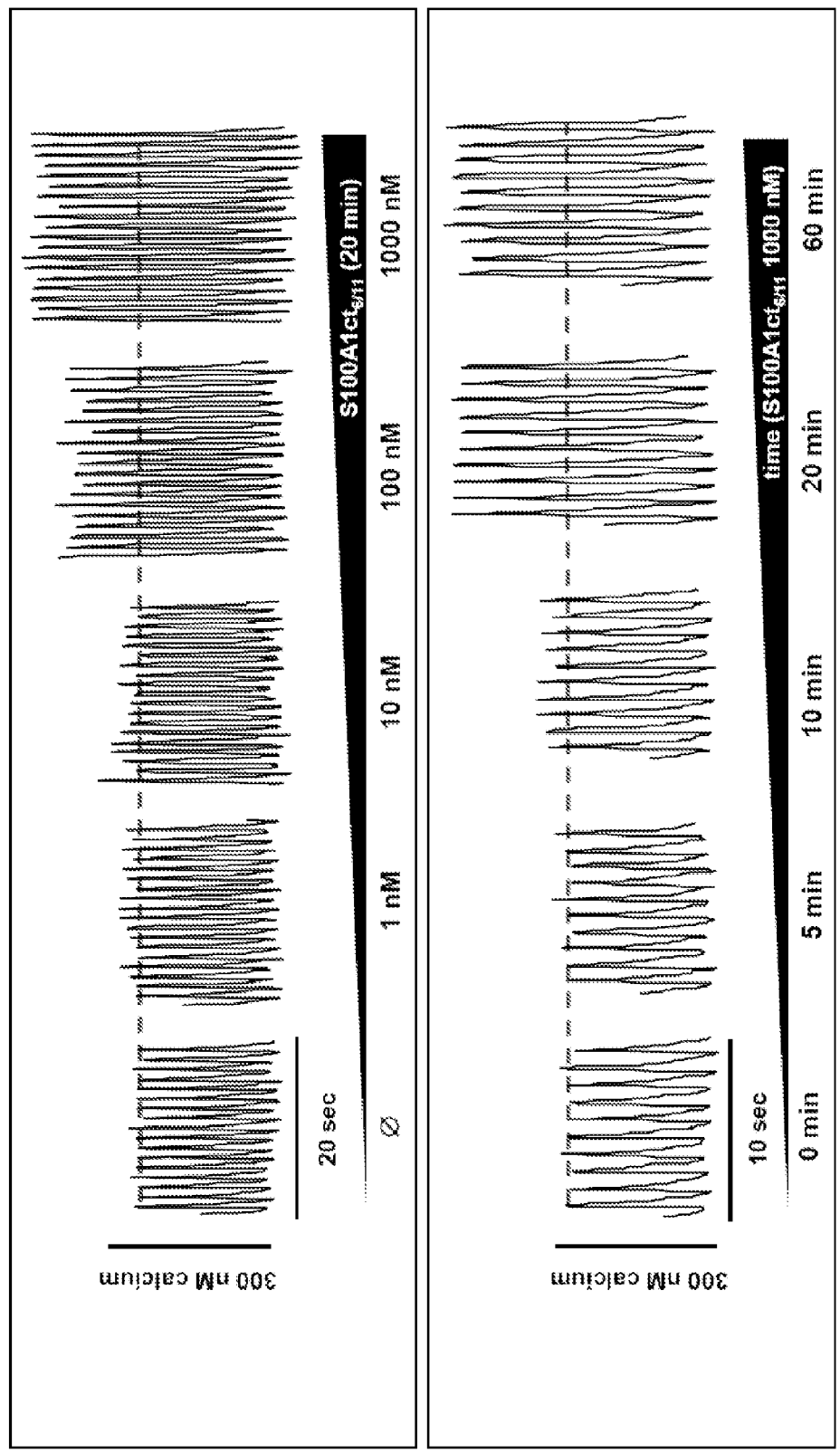

FIG. 9: Time- and dose-dependent positive inotropic effect of S100A1ct$_{6/11}$ in electrical field stimulated isolated ventricular rat cardiomyocytes.

S100A1 ct$_{6/11}$ mimics the inotropic effect both of viral-mediated and cardiac-targeted transgenic S100A1 over-expression in adult ventricular cardiomyocytes in a dose-dependent and time-dependent manner. FIG. 9 shows representative tracings of the dose-dependent (upper panel) and time-dependent (lower panel) positive inotropic effect of S100A1ct$_{6/11}$ in isolated electrical-field stimulated (2 Hz) rat ventricular cardiomyocytes. Note the onset of S100A1ct$_{6/11}$ inotropic actions between 10 and 20 minutes in line with its intracellular accumulation after 15 minutes extracellular exposure (FIG. 8B). Calculated EC50% is 87±6 nM S100A1ct$_{6/11}$. Calcium transients were assessed in FURA2-AM field-stimulated cardiomyocytes employing epifluorescent digitalized microscopy.

Figure 10:
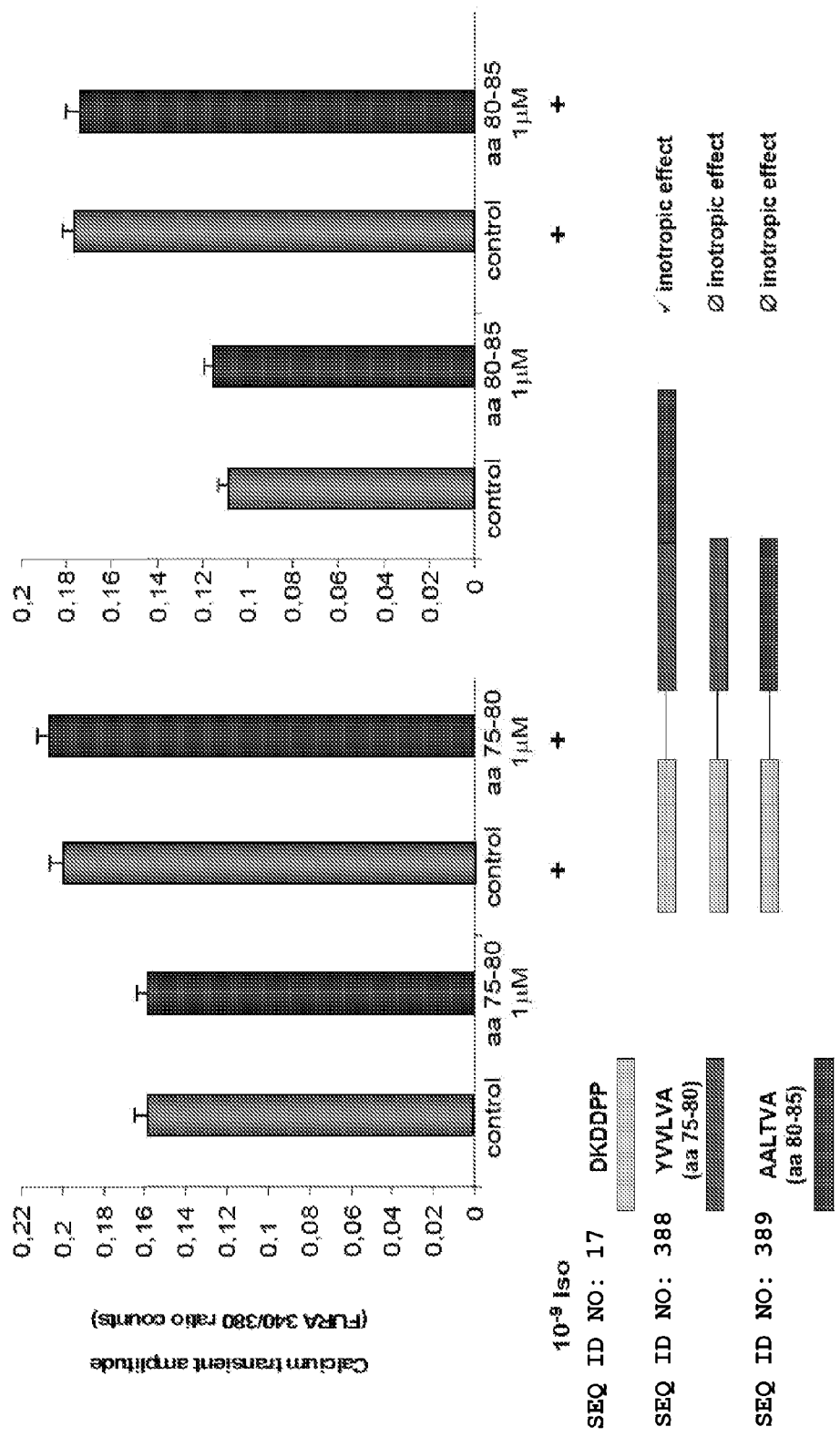

FIG. 10: Neither the synthetic peptide D-K-D-D-P-P-Y-V-V-L-V-A (amino acids 75-80 of human S100A1 fused to a hydrophilic motif, SEQ ID NO: 44) nor the synthetic peptide D-K-D-D-P-P-A-A-L-T-V-A (amino acids 80-85 of human S100A1 fused to a hydrophilic motif, SEQ ID NO: 45) is sufficient to mimic or reproduce inotropic effects of S100A1ct$_{6/11}$. Calcium transients were assessed in FURA2-AM field-stimulated cardiomyocytes employing epifluorescent digitalized microscopy (n=60 in each group).

Figure 11:
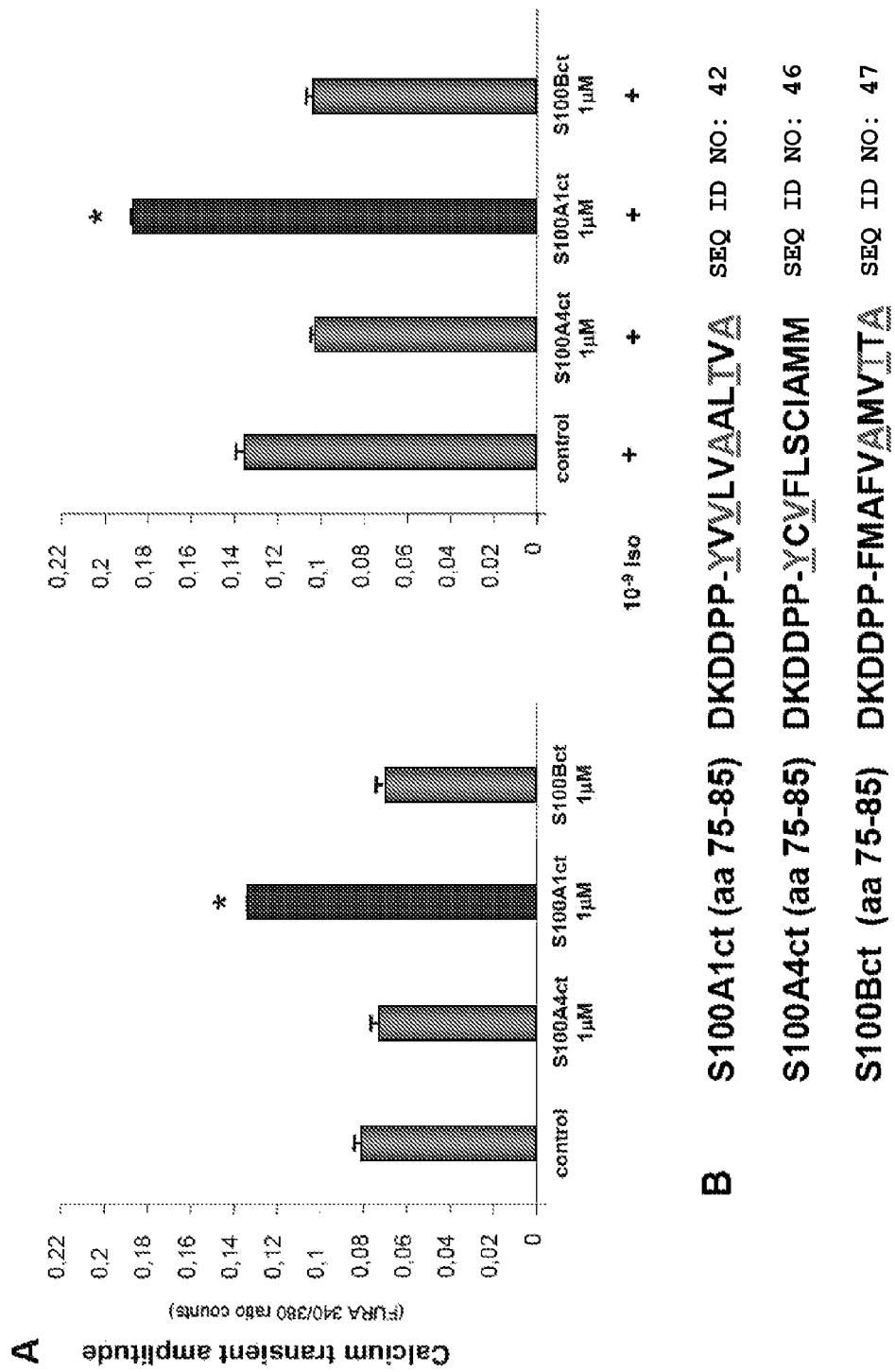

FIG. 11: Peptides encompassing amino acids 75-85 derived from S100 paralogs A4 and B are not sufficient to mimic S100A1ct$_{6/11}$ mediated inotropy.

Both the synthetic peptide D-K-D-D-P-P-Y-C-V-F-L-S-C-I-A-M-M (amino acids 75-85 of S100A4 fused to a hydrophilic motif, SEQ ID NO: 46) and D-K-D-D-P-P-F-M-A-F-V-A-M-V-T-T-A (amino acids 75-85 of S100B fused to a hydrophilic motif, SEQ ID NO: 47) fail to reproduce S100A1ct$_{6/11}$ inotropic actions. (A) shows that neither S100A4ct nor S100Bct mimic S100A1ct$_{6/11}$ inotropic effects under basal (left panel) and β-AR stimulated conditions (right panel). (B) depicts primary sequence alignment of D-K-D-D-P-P (SEQ ID NO: 17) coupled amino acids 75-85 peptides derived from S100A1 (top), S100A4 (middle) and S100B (down). Identical amino acids between S100A1ct and S100A4ct and S100Bct are underlined. (n=60 cells in each group, *P<0.05 vs. control, S100A4ct and S100Bct, 2-way ANOVA). $10^{-9}$ Iso means $10^{-9}$ M Isoproterenol.

Figure 12:
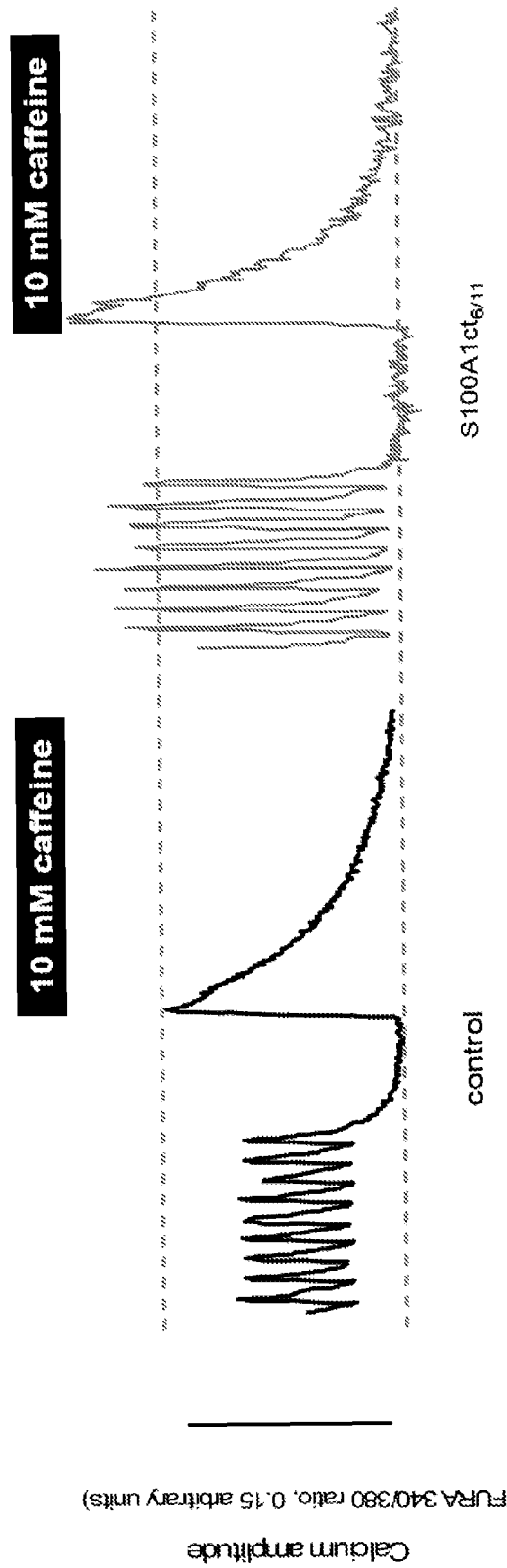

FIG. 12: The inotropic effect of S100A1ct$_{6/11}$ is associated with control and regulation of the sarcoplasmic reticulum (SR) calcium content.

Inotropic effects of S100A1ct$_{6/11}$ are conveyed by enhanced SR calcium load similar to effects of native human S100A1 protein employing viral-mediated and cardiac-targeted transgenic S100A1 over-expression in adult ventricular cardiomyocytes. FIG. 12 depicts representative tracings of a field-stimulated (2 Hz) control (black, left trace) and S100A1ct$_{6/11}$ (1000 nM, light grey, right trace) ventricular cardiomyocyte subjected to 10 mM caffeine in vitro resulting in complete release of SR calcium. The amplitude of the caffeine evoked calcium transient serves as an indirect measure of the SR calcium content being greater in S100A1ct$_{6/11}$ treated cardiomyocytes. These data indicate that S100A1ct$_{6/11}$ inotropic effects are associated with control and enhanced SR calcium storage and content.

FIG. 13: The positive inotropic effect of S100A1ct$_{6/11}$ in cardiomyocytes is additive and independent of β-adrenergic stimulation and signaling, respectively.

(A) shows a representative Western blot employing phospho-specific antibodies revealing that S100A1ct$_{6/11}$ neither recruits nor alters β-adrenergic receptor (βAR) signaling including cAMP-dependent kinase (PKA) activity at sarcoplasmic reticulum (phospholamban, PLB) and sarcomeric (troponin I, TnI) targets under basal conditions and βAR stimulation. In support of this, FIG. 13B shows that S100A1

$ct_{6/11}$ inotropic effects are additive and preserved under βAR stimulation assessed in FURA2-AM field-stimulated cardiomyocytes employing epifluorescent digitalized microscopy. Note that the major inotropic effect of the βAR-PKA axis is conveyed by enhanced PLB-ser16 phosphorylation. $S100A1ct_{6/11}$ neither includes nor alters this mechanism explaining its additive inotropic effect on βAR stimulation. (n=60 cells in each group, *P<0.05 vs. control, 2-way ANOVA). $10^{-9}$ Iso means $10^{-9}$ M Isoproterenol.

Figure 14:
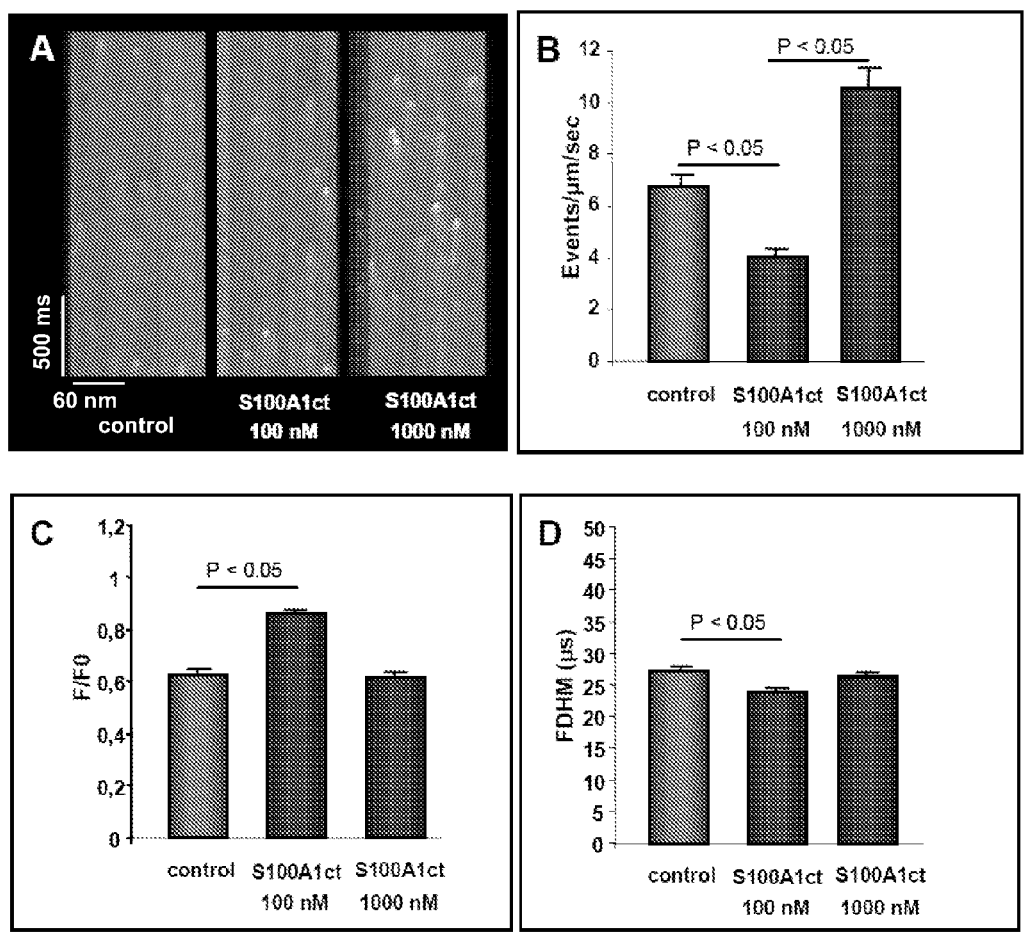

FIG. 14: $S100A1ct_{6/11}$ controls diastolic RyR2 function and modulates physiologic diastolic SR calcium spark frequency in ventricular cardiomyocytes.

$S100A1ct_{6/11}$ modulates diastolic SR calcium spark frequency in intact ventricular cardiomyocytes and mimics the effect of cell-impermeable native S100A1 protein and the 20-mer S100A1 C-terminal domain peptide in permeabilized ventricular cardiomyocytes. FIG. 14A shows representative confocal tracings of calcium sparks in Fluo-3 AM loaded control and $S100A1ct_{6/11}$ treated quiescent ventricular rat cardiomyocytes. FIG. 14B-D depict that $S100A1ct_{6/11}$ differentially controls diastolic SR calcium spark frequency and amplitude. While 100 nM $S100A1ct_{6/11}$ decreases calcium spark frequency under basal conditions, a ten-fold greater $S100A1ct_{6/11}$ concentration (1000 nM) enhances calcium spark frequency (n=60 cells in each group, 2-way ANOVA).

Figure 15:
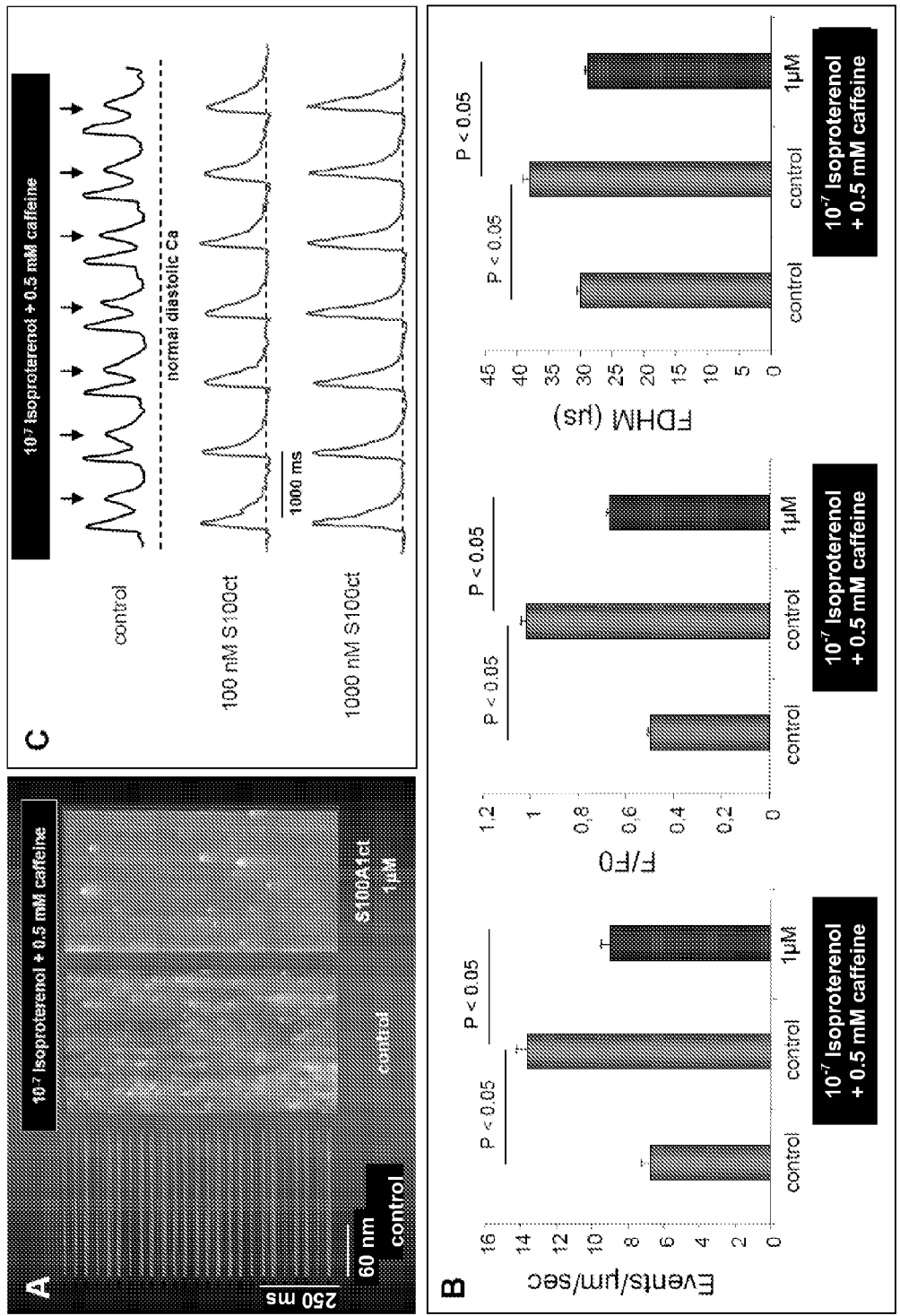

FIG. 15: The molecular mechanism conveying $S100A1ct_{6/11}$ inotropic effects concurrently protects cardiomyocytes from pro-arrhythmic store overload-induced calcium release (SOICR) and calcium waves, respectively.

SOICR, being a critical pathomechanism for arrhythmogenic sudden cardiac death, was evoked in vitro employing a previously published protocol by Isner and co-workers (Venetucci et al., 2007, Circ Res 100:105-111). FIG. 15A shows representative confocal tracings of calcium sparks in a Fluo-3 AM loaded control cardiomyocyte (left) which frequency and spatial characteristics are dramatically increased under conditions (βAR stimulation+0.5 mM caffeine) resulting in SOICR (middle) as described by (Venetucci et al., 2007, Circ Res 100:105-111). Note that treatment with 1000 nM $S100A1ct_{6/11}$ (FIG. 15A, right) effectively antagonizes the SR calcium leak. FIG. 15B reveals statistical analysis of the therapeutic impact of $S100A1ct_{6/11}$ normalizing abnormal calcium spark frequency and spatial characteristics in the presence of isoproterenol/caffeine. FIG. 15C depicts the potent anti-arrhythmic effect of $S100A1ct_{6/11}$ with representative tracings of a control cardiomyocyte exhibiting SOICR triggered calcium waves in the presence of βAR stimulation+0.5 mM caffeine that are completely prevented by 100 nM and 1000 nM $S100A1ct_{6/11}$. Given that SOICR and subsequent calcium waves are molecular substrates for lethal ventricular arrhythmias and sudden cardiac death, these experiments uncover the unique molecular profile of $S100A1ct_{6/11}$ combining inotropy with protection from calcium-induced arrhythmias in cardiomyocytes (n=60 cells in each group, 2-way ANOVA). It is important to note that the protective effect of $S100A1ct_{6/11}$ is effective at concentrations (100 nM and 1000 nM) that exert inotropic actions in cardiomyocytes (FIG. 9) due to enhanced SR calcium load. Thus, despite its own enhancing effect on SR calcium resequestration, $S100A1ct_{6/11}$ effectively antagonizes βAR-triggered SOICR highlighting the unique molecular profile combining inotropic actions with anti-arrhythmic potency. Akin $S100A1ct_{6/11}$, viral-mediated S100A1 over-expression also prevented βAR-triggered pro-arrhythmic SR calcium leak in adult ventricular cardiomyocytes with leaky RyR2s indicating that cell-permeable $S100A1ct_{6/11}$ mimics the anti-arrhythmic effect of over-expressed S100A1 protein.

Figure 16:
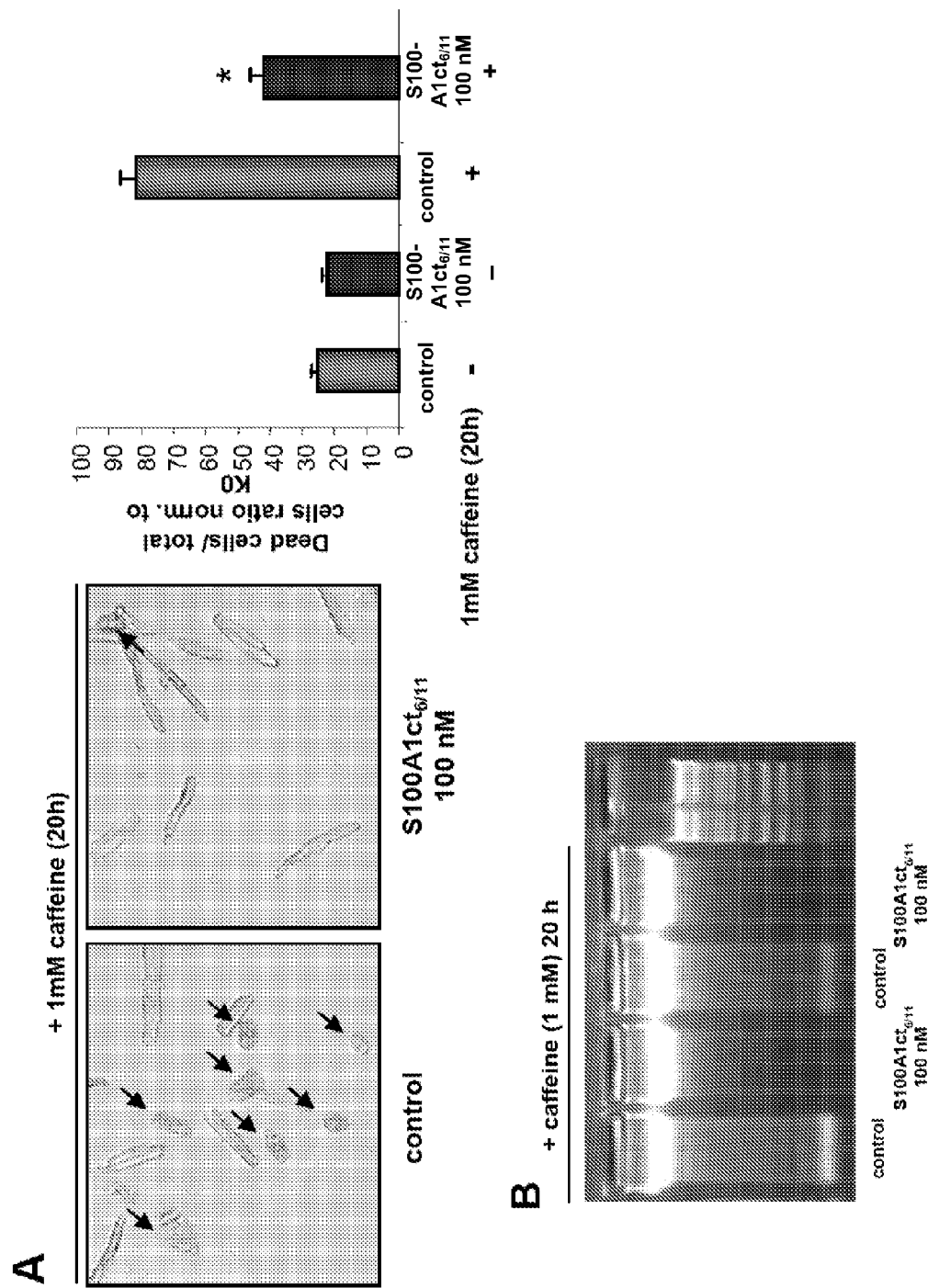

FIG. 16: The molecular mechanism conveying $S100A1ct_{6/11}$ inotropic effects concurrently protects cardiomyocytes from apoptotic cell death due to the prevention of SR calcium leak. $S100A1ct_{6/11}$ protects adult ventricular cardiomyocytes with leaky RyR2s that are sensitized to luminal calcium by long-term caffeine exposure from apoptotic cell death. FIG. 16A shows representative images of control and $S100A1ct_{6/11}$ treated cardiomyocytes exposed to caffeine. Black arrowheads highlight dead cells due to SR calcium leak induced apoptosis facilitated by leaky RyR2. Statistical analysis revealed significantly less apoptotic cardiomyocytes in the $S100A1ct_{6/11}$ treated group. FIG. 16B shows a representative DNA gel of two independent experiments with laddered DNA in control but not $S100A1ct_{6/11}$ treated cardiomyocytes indicative of a prevention of apoptosis.

Figure 17:
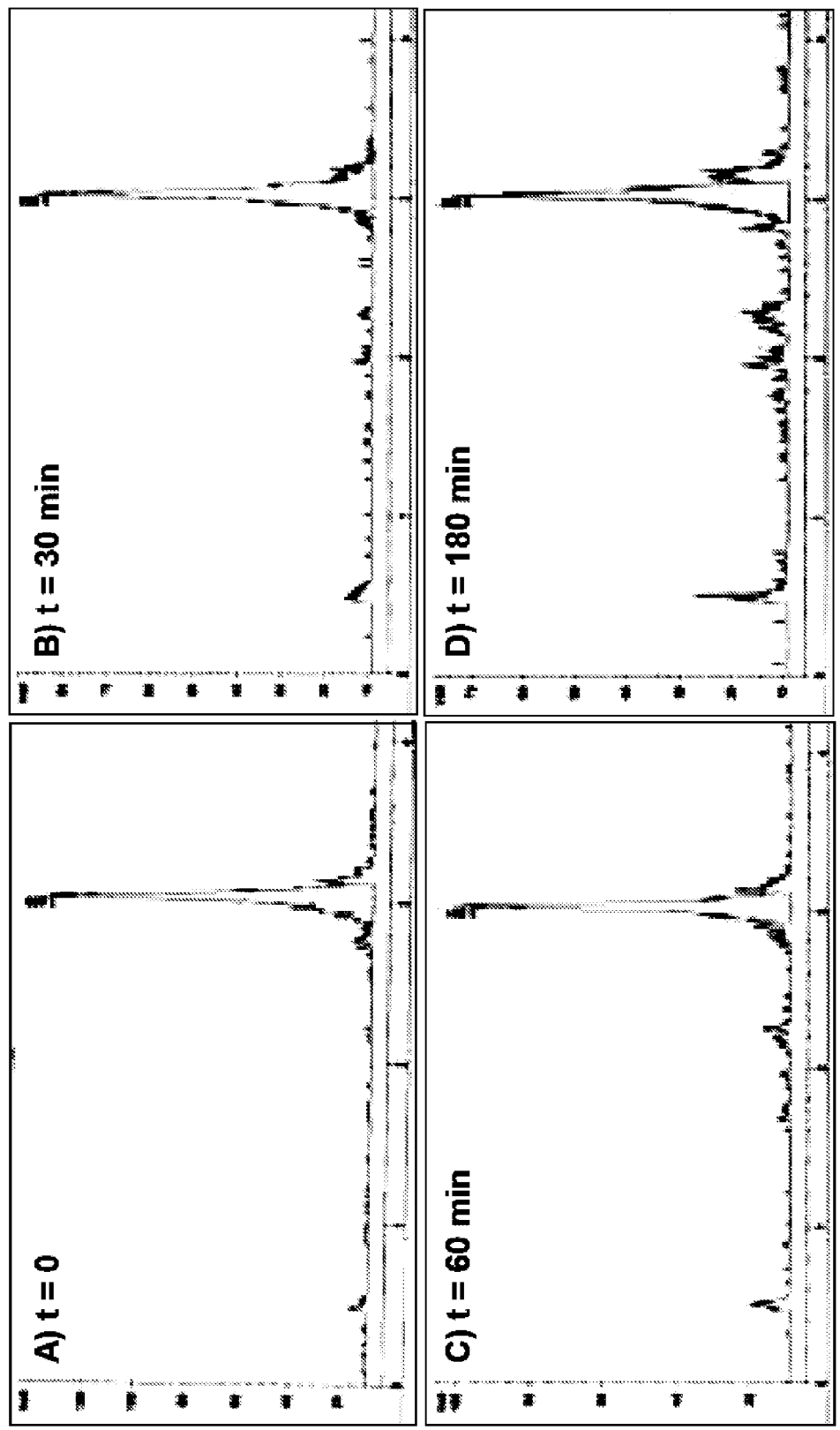

FIG. 17: $S100A1ct_{6/11}$ resists cleavage and degradation in human serum enabling application and long-term biological effectiveness in vivo.

Human serum spiked with $S100A1ct_{6/11}$ in vitro (1 µM) shows uncleaved $S100A1ct_{6/11}$ for up to 3 hours indicating high serum stability as a prerequisite for in vivo administration and biological long-term effectiveness. A-D show representative tracings of MALDI-TOF analyses of human serum samples spiked with 1 µM $S100A1ct_{6/11}$ in vitro at different time points. Note that Figure A throughout D reveals no cleavage and degradation of $S100A1ct_{6/11}$ indicating high stability in a protease rich environment.

Figure 18:
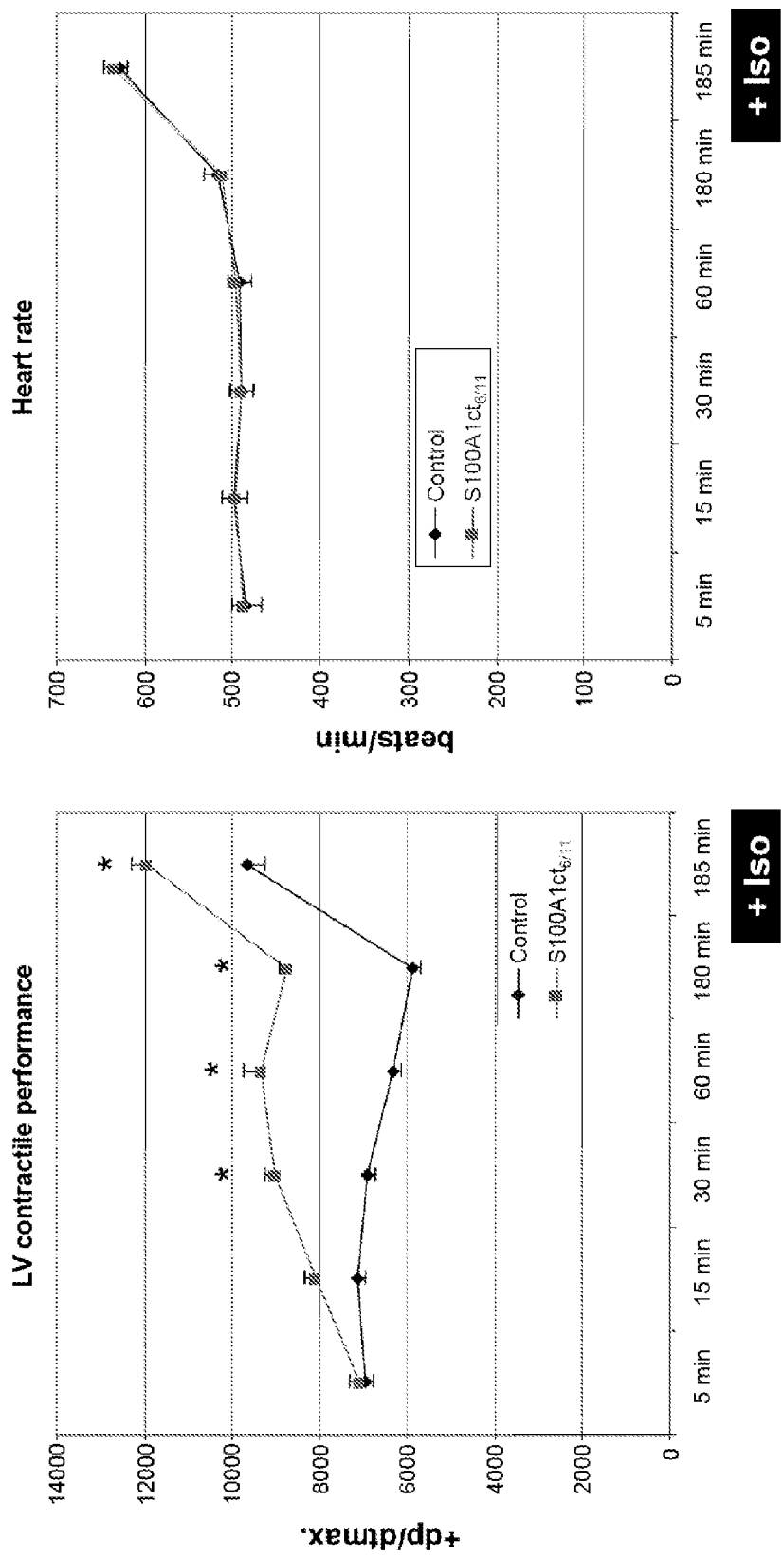

FIG. 18: $S100A1ct_{6/11}$ exerts significant in vivo hemodynamic effects resulting in enhanced contractile performance under basal and βAR-stimulated conditions.

Anesthetized adult C57/B6 male mice (30 g BW) receiving a single intravenous (i.v.) application of 225 ng $S100A1ct_{6/11}$ (squares) exhibited a 3-hour lasting enhancement of left ventricular contractile performance (left panel) that was preserved and additive to i.v. isoproterenol application (250 pg) (compare to solid diamonds of control animals). Note that the in vivo effect reflects in vitro actions of $S100A1ct_{6/11}$ under basal and βAR stimulated conditions. The inotropic effect of $S100A1ct_{6/11}$ in vivo was independent of heart rate and its responsiveness to βAR stimulation (right panel). $S100A1ct_{6/11}$ is also effective with delayed onset after intraperitoneal and subcutaneous use. FIG. 18 shows significantly enhanced basal contractile performance assessed by left ventricular catherization in anesthetized mice after i.v. $S100A1ct_{6/11}$ injection. The gain in function was preserved under βAR stimulation and independent of heart rate (n=7 animals in each group, *P<0.05 vs. corresponding control animal, 2-way ANOVA).

Figure 19:
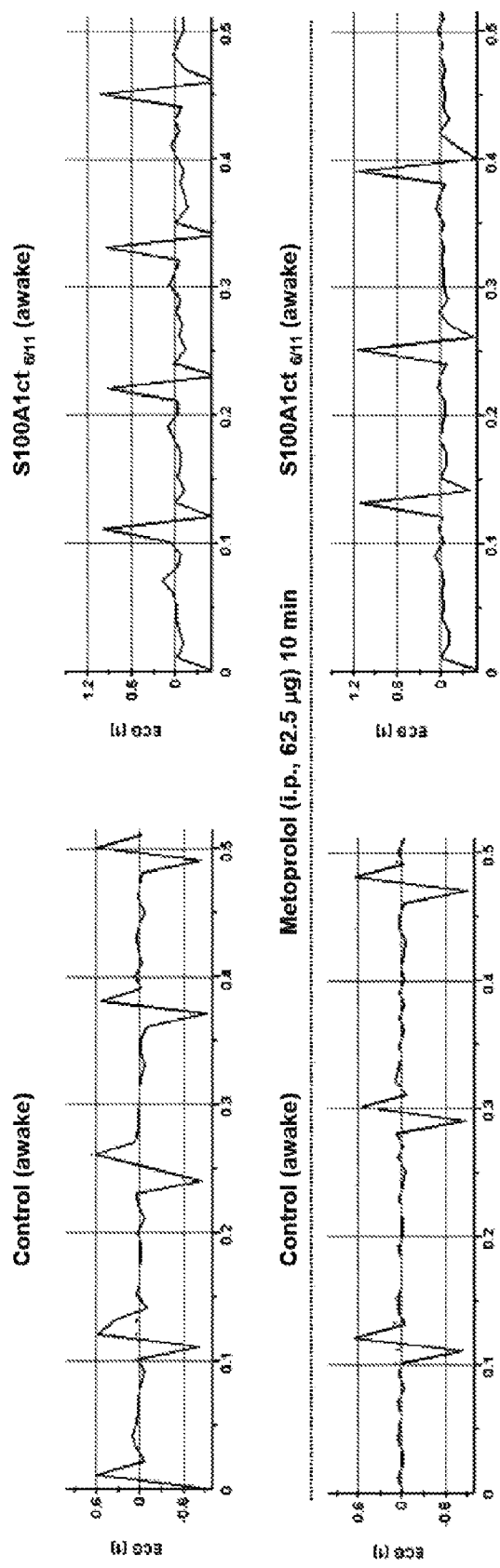

FIG. 19: $S100A1ct_{6/11}$ exerts significant in vivo hemodynamic effects which are effective in response to the β1AR-blocker metoprolol.

Figure 20:
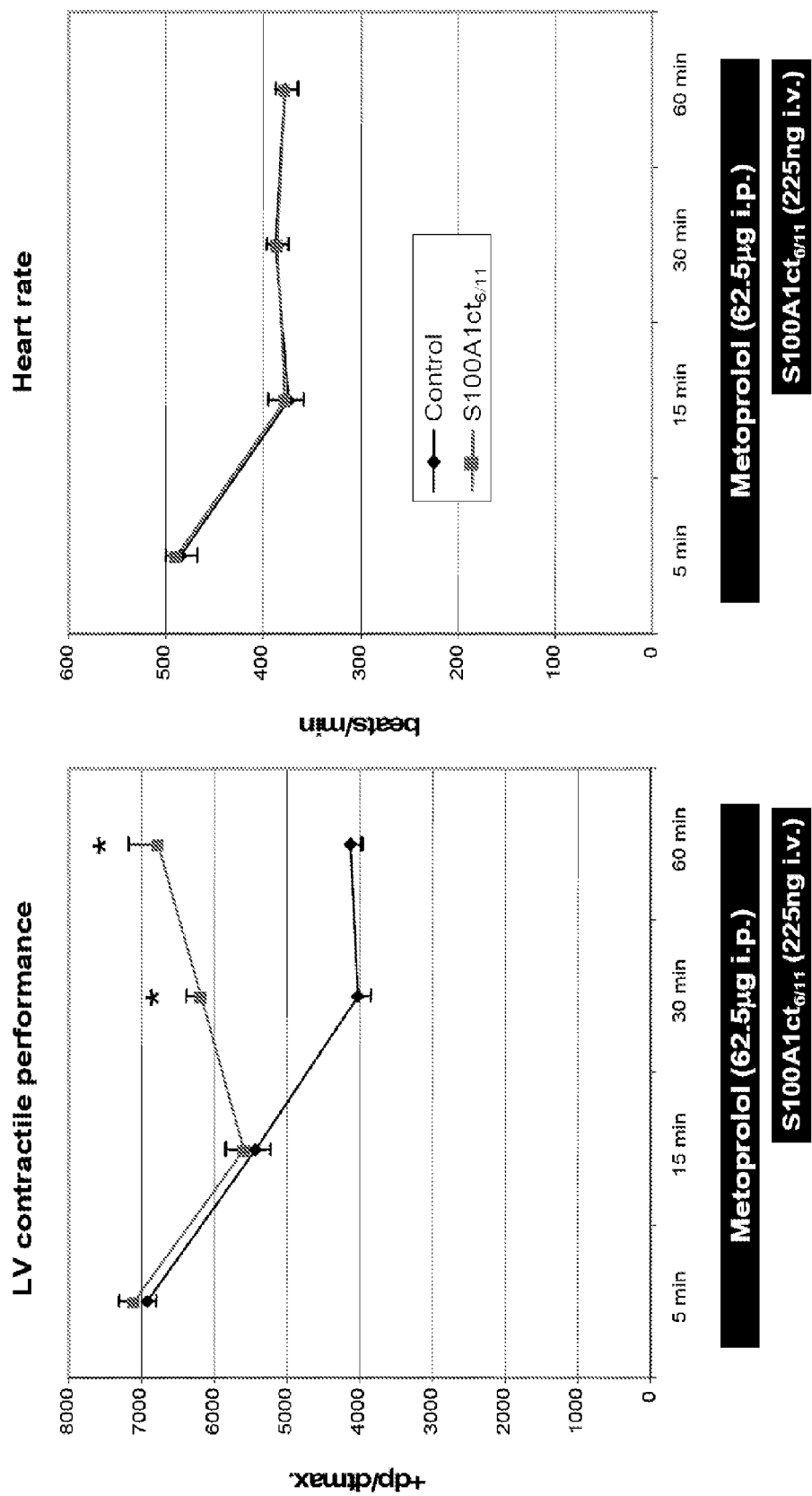

Anesthetized adult C57/B6 male mice (30 g BW) receiving a single intravenous (i.v.) application of 225 ng $S100A1ct_{6/11}$ 15 min after intraperitoneal (i.p.) administration of metoprolol (62.5 µg) showed similar slowing in heart rate (FIG. 19) without ECG abnormalities but preserved $S100A1ct_{6/11}$ mediated gain in function (FIG. 20). FIG. 19 shows representative telemetric ECG recordings (DSI systems, Einthoven lead II) in a control (i.v. vehicle) and i.v. treated $S100A1ct_{6/11}$ mice with similar slowing in heart rate without conduction abnormalities in response to metoprolol.

FIG. 20: shows preserved $S100A1ct_{6/11}$ inotropic effectiveness in presence of the β1AR blocker metoprolol in anesthetized mice (left panel). Note that $S100A1ct_{6/11}$ antagonized the negative inotropic but not the negative chronotropic effect of metoprolol (right panel) highlighting feasibility of combined S100A1ct$_{6/11}$ and metoprolol therapy for cardiac dysfunction (n=7 animals in each group, *P<0.05 vs. corresponding control animal, 2-way ANOVA).

Figure 21:
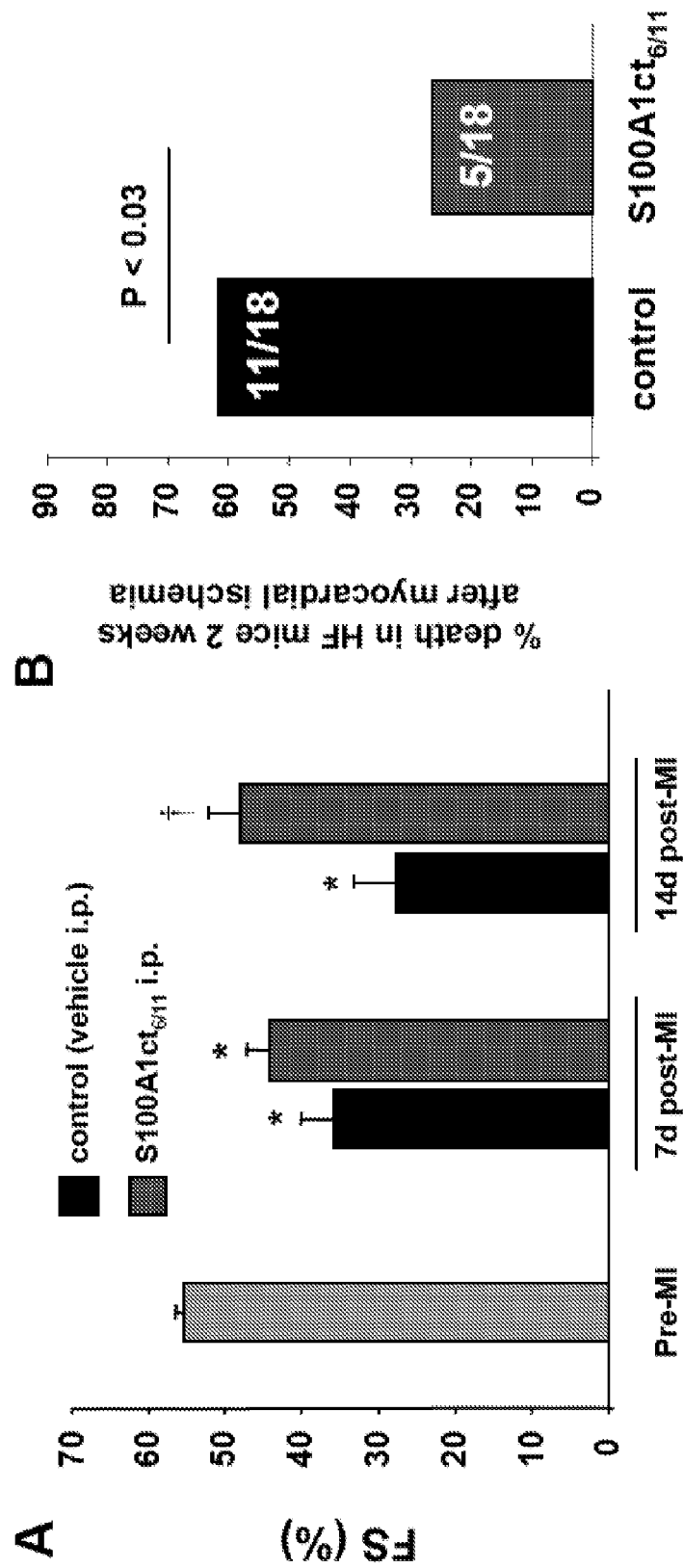

FIG. 21: S100A1ct$_{6/11}$ exerts significant therapeutic effects in vivo restoring hemodynamic function in an experimental mouse heart failure model.

Daily S100A1ct$_{6/11}$ i.p. treatment of adult C57/B6 male/female mice with postischemic contractile dysfunction at 225 ng (30 g BW) for 2 weeks results in significantly improved cardiac performance and survival. FIG. 21A depicts the therapeutic effect of 2-week i.p. S100A1ct$_{6/11}$ heart failure treatment restoring left ventricular performance in mice with contractile dysfunction assessed by serial echocardiography. FIG. 21B depicts that improved contractile performance in S100A1ct$_{6/11}$ treated heart failure mice is translated in significantly improved survival. (A, n=10 animals in each group; B, 18 animals in each group, *P<0.05 vs. pre-MI, †P<0.01 vs. control heart failure animals, 2-way ANOVA).

Figure 22:
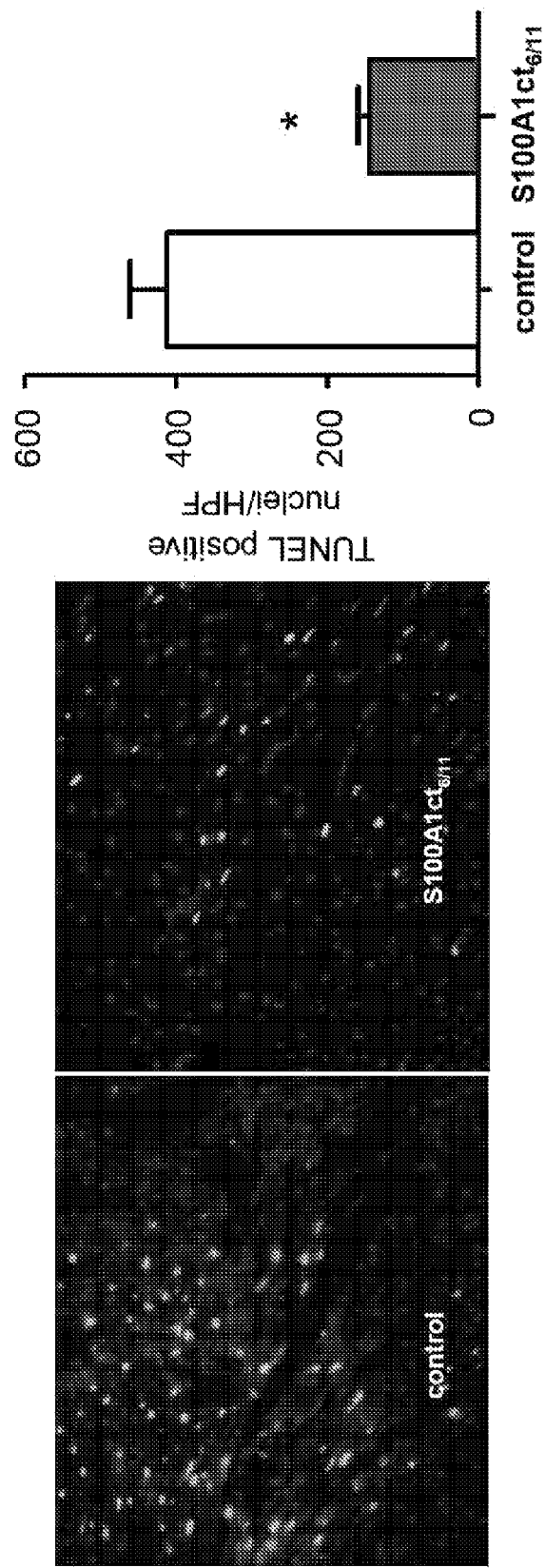

FIG. 22: S100A1ct$_{6/11}$ exerts significant therapeutic effects in vivo preventing apoptotic cell death in failing myocardium in an experimental heart failure animal model.

Daily S100A1ct$_{6/11}$ i.p. treatment of adult C57/B6 male/female mice with postischemic contractile dysfunction at 225 ng (30 g BW) for 2 weeks resulted in significantly diminished apoptosis in failing hearts. Note that the in vivo effect reflects the anti-apoptotic action of S100A1ct$_{6/11}$ in cardiomyocytes in vitro. FIG. 22 shows representative TUNEL stainings of a heart failure (HF) control and an S100A1ct$_{6/11}$ treated failing heart (2-week i.p.) where green nuclei indicate DNA strand breaks labeled by a FITC-coupled probe. Note that the S100A1ct$_{6/11}$ treated failing heart exhibits less apoptotic nuclei (middle panel). Statistical analysis revealed a significant reduction of apoptosis in S100A1ct$_{6/11}$ treated failing hearts contributing to the overall therapeutic effect on survival (n=6 animals in each group, P<0.01 vs. control hearts, 2-way ANOVA).

Figure 23:
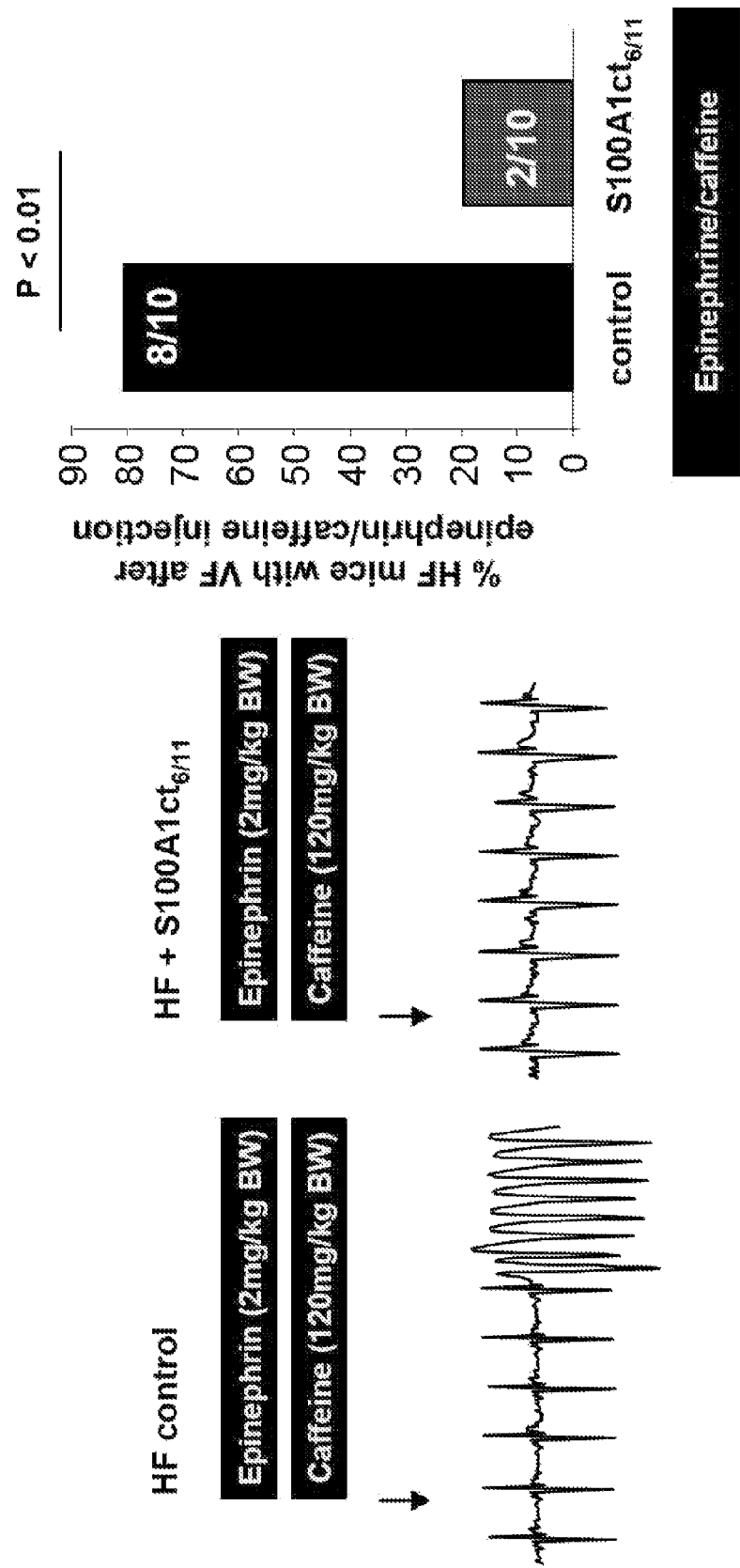

FIG. 23: S100A1ct$_{6/11}$ exerts significant therapeutic effects in vivo protecting heart failure mice from βAR triggered lethal ventricular tachyarrhythmias.

Daily S100A1ct$_{6/11}$ i.p. treatment of adult C57/B6 male/female mice with postischemic contractile dysfunction at 225 ng (30 g BW) for 2 weeks protects from βAR triggered ventricular fibrillations in hearts with calcium sensitized leaky RyR2 channels by caffeine. The pro-arrhythmogenic protocol in heart failure mice was adapted from the previously published protocol by Wayne Chen and co-workers (Xiao et al., 2007, JBC 282:34828-34838). FIG. 23 shows representative ECG tracings in a heart failure control and S100A1ct$_{6/11}$ treated mouse (2-week i.p.) exposed to i.p. epinephrin/caffeine injection resulting in abrupt onset of lethal ventricular fibrillation (left panel). Note that lethal ventricular fibrillation only occurred in 2 out of 10 animals in the S100A1ct$_{6/11}$ treated group whereas control heart failure mice showed 80% mortality (Contingency tested by Fischer's exact test).

Figure 24:
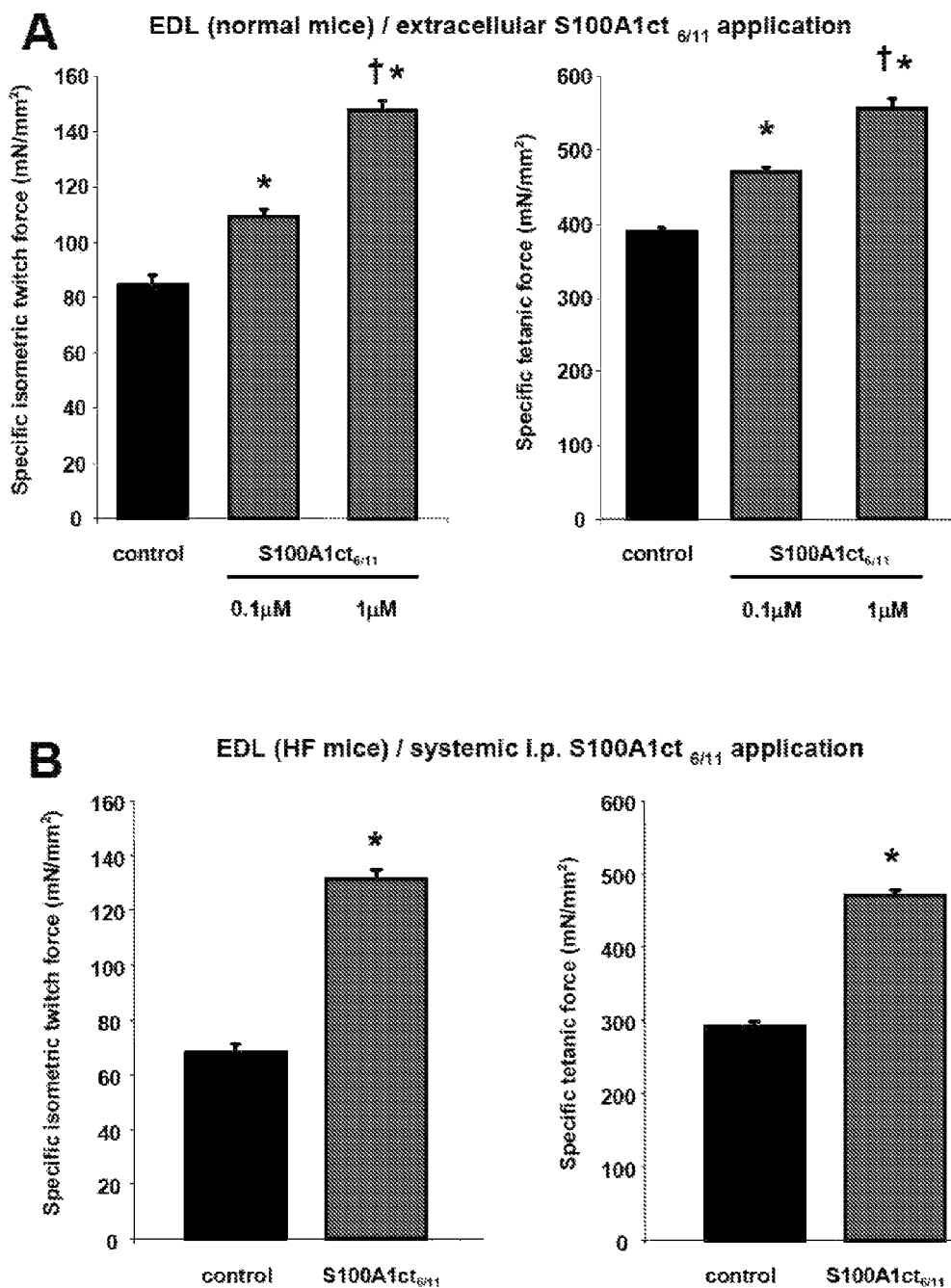

FIG. 24: S100A1ct$_{6/11}$ significantly enhances isometric twitch force in normal and diseased skeletal muscle.

Incubation of intact extensor digitorum longum (EDL) skeletal muscle isolated from 12 weeks old C57/B6 male mice with S100A1ct$_{6/11}$(1 µM) for 45 min resulted in significantly enhanced specific isometric and tetanic twitch force as shown in FIG. 24A applying a method for muscle isolation and isometric tension measurement as previously published by the inventors (Most et al., 2003, J. Biol. Chem. 278:26356-26364). Tetanic train was applied at 125 Hz for 175 ms reaching a stable force plateau. Moreover, post-myocardial infarction heart failure mice generated by the inventors as described previously (Most et al., 2006, Circulation 114:1258-1268) presented with improved skeletal muscle function after a 2-week i.p. S100A1ct$_{6/11}$ (225 ng, daily injections) treatment as shown in FIG. 24B. This is a significant finding as major clinical symptoms such as fatigue and impaired exercise capacity in heart failure patients are caused by impaired skeletal muscle function and are not directly related to cardiac output. FIG. 24A shows that extracellular application of S100A1ct$_{6/11}$ (0.1-1 µM) significantly enhances EDL isometric and tetanic twitch force in a dose-dependent manner. FIG. 23B depicts that systemic (i.p.) S100A1ct$_{6/11}$ administration in heart failure mice attenuates skeletal muscle dysfunction and significantly improves contractile performance (n=5 muscles/animals in each group, *P<0.05 vs. corresponding control, †P<0.01 vs. control, 2-way ANOVA).

Figure 25:
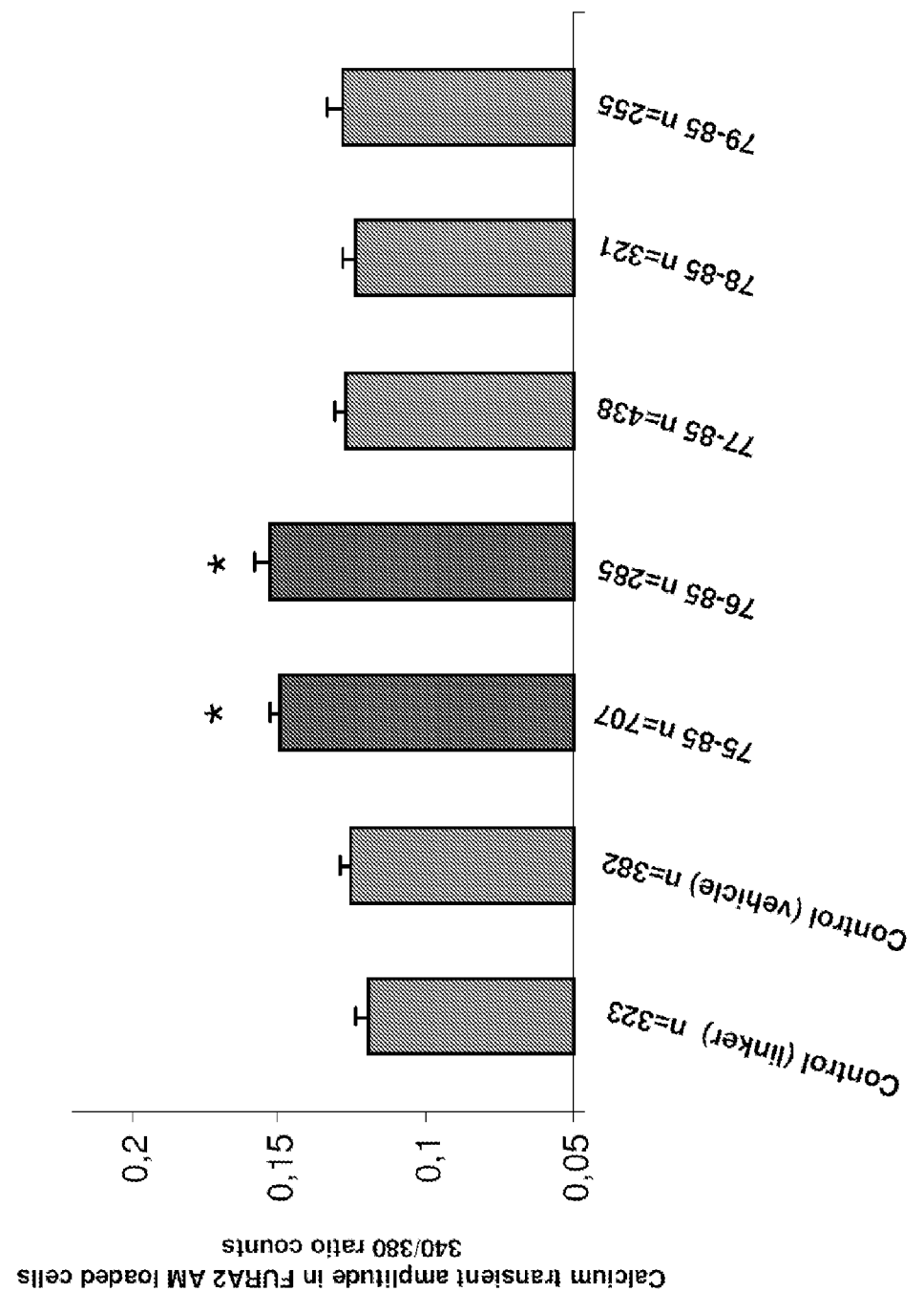

FIG. 25: Effect of S100A1 peptides N-75-85-C (amino acids 75 to 85 of human S100A1 protein set forth in SEQ ID NO: 38), N-76-85-C (amino acids 76 to 85 of human S100A1 protein set forth in SEQ ID NO: 38), N-77-85-C (amino acids 77 to 85 of human S100A1 protein set forth in SEQ ID NO: 38), N-78-85-C (amino acids 78 to 85 of human S100A1 protein set forth in SEQ ID NO: 38), N-79-85-C (amino acids 79 to 85 of human S100A1 protein set forth in SEQ ID NO: 38) on calcium transient amplitudes in field-stimulated (1 Hz) isolated rat ventricular cardiomyocytes. Note that N-75-85-C and N-76-85-C have similar potency in enhancing the calcium transient. Any further deletion of N-terminal amino acids abolishes the inotropic effect of the peptide. n equals the number of tested cells from three different preparations. *P<0.05 vs. hydrophobic element and vehicle, ANOVA.

Figure 26:
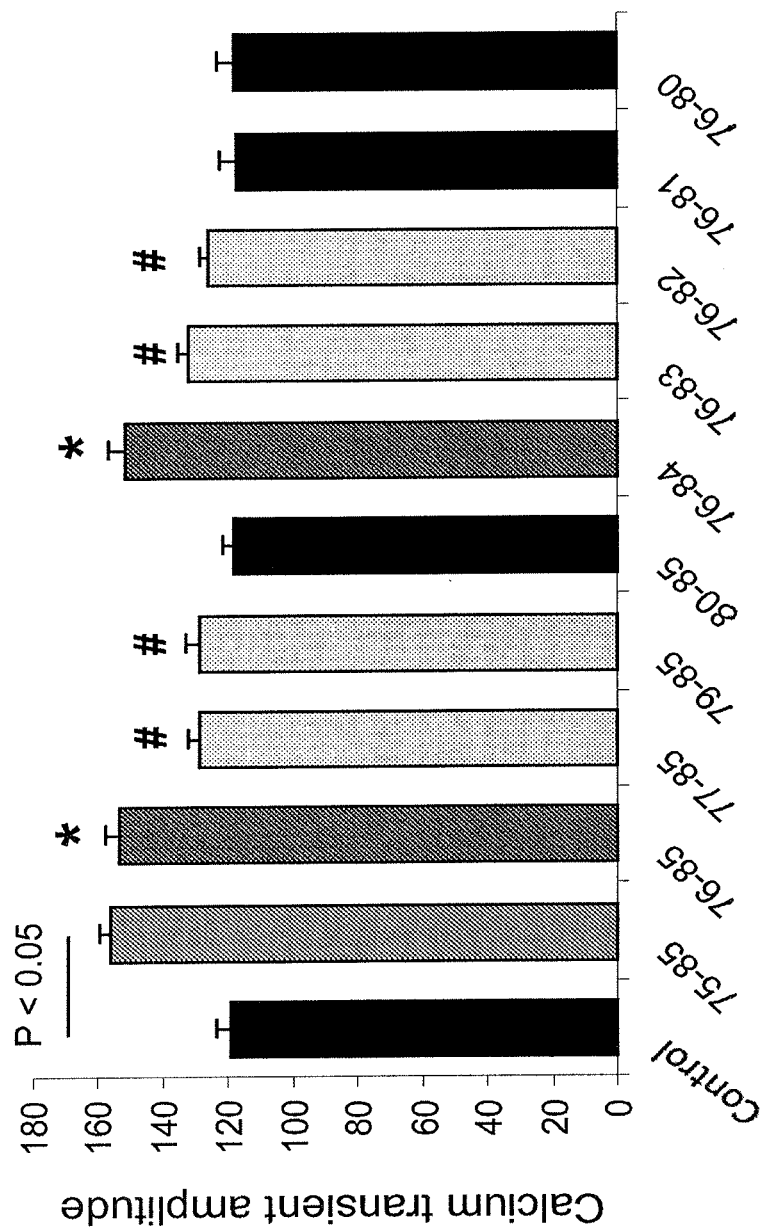

FIG. 26: Inotropic effect of shortened peptides consisting of the sequences D-K-D-D-P-P-V-L-V-A-A-L-T-V-A (SEQ ID NO: 32), D-K-D-D-P-P-L-V-A-A-L-T-V-A (SEQ ID NO: 433), D-K-D-D-P-P-V-A-A-L-T-V-A (SEQ ID NO: 34), D-K-D-D-P-P-V-V-L-V-A-A-L-T-V (SEQ ID NO: 35), D-K-D-D-P-P-V-V-L-V-A-A-L-T (SEQ ID NO: 36), and D-K-D-D-P-P-V-V-L-V-A-A-L (SEQ ID NO: 37). Shown is the statistical analysis of the listed peptides with respect to the increase in the calcium transient amplitude over control cells. Dark grey bars indicate shortened peptides (76-85 and 76-84) with full functional equivalence, light grey bars indicate peptides (77-85, 79-85, 76-83 and 76-82) with partial functional equivalence and black bars indicate peptides with no effect compared to S100A1ct$_{6/11}$ lacking the N-terminal Y (75-85, intermediate grey bar). Cells were from three independent preparations, n=62 cells

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in an embodiment of the peptide according to the present invention the inotropic peptide comprises or consists of an S100A1 protein derived domain, wherein said S100A1 protein derived domain consists of 4 to 9 consecutive amino acids of the inotropic motif [V/I]-[V/I]-[L/M]-[V/I/M]-[A/G/S]-[A/V]-L-[T/A]-[V/A/I]-[A/M/V](SEQ ID NO: 416), and in another embodiment the hydrophilic motif comprises or consists of the hydrophilic amino acid motif $\Lambda_4$-$\Theta_2$, wherein $\Lambda$ and $\Theta$ are as defined herein below and the hydrophilic motif is preferably directly linked to the amino terminus of the amino acid motif comprised by the muscle function enhancing amino acid sequence, a peptide comprising the amino acid sequence $\Lambda_4$-$\Theta_2$-[V/I]-[V/I]-[L/M]-[V/I/M]-[A/G/S]-[A/V]-L-[T/A]-[V/A/I] (SEQ ID NO: 417) is an embodiment of the peptide according to the present invention.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, cell biology, and recombinant DNA techniques are employed which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989). Furthermore, conventional methods of clinical cardiology are employed which are also explained in the literature in the field (cf., e.g., *Practical Methods in Cardiovascular Research*, S. Dhein et al. eds., Springer Verlag Berlin Heidelberg, 2005).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

A "peptide" according to the present invention refers to a chain of amino acid residues which may be naturally occurring or derivatives of naturally occurring amino acid residues and which are preferably linked via peptide bonds, wherein the peptide consists of not more than 100 amino acid residues or amino acid residue derivatives. The term "amino acid" encompasses naturally occurring amino acids as well as amino acid derivatives. A "small amino acid" in the context of the present invention is preferably an amino acid having a molecular weight of less than 125 Dalton. Preferably, a small amino acid in the context of the present invention is selected from the group consisting of the amino acids glycine, alanine, serine, cysteine, threonine, and valine, or derivatives thereof. A hydrophobic non-aromatic amino acid in the context of the present invention, is preferably any amino acid which has a Kyte-Doolittle hydropathy index of higher than 0.5, more preferably of higher than 1.0, even more preferably of higher than 1.5 and is not aromatic. Preferably, a hydrophobic non-aromatic amino acid in the context of the present invention, is selected from the group consisting of the amino acids alanine (Kyte Doolittle hydropathy index 1.8), methionine (Kyte Doolittle hydropathy index 1.9), isoleucine (Kyte Doolittle hydropathy index 4.5), leucine Kyte Doolittle hydropathy index 3.8), and valine (Kyte Doolittle hydropathy index 4.2), or derivatives thereof having a Kyte Doolittle hydropathy index as defined above.

"Muscle" in the context of the present invention means preferably striated muscle tissue or muscle cells derived from striated muscle tissue such as skeletal muscle cells/tissue and cardiac muscle cells (cardiomyocytes) and cardiac muscle tissue.

According to the present invention, the term "muscle function enhancing amino acid sequence" refers to an amino acid sequence that is capable of enhancing and/or restoring any muscle-specific function, for example, enhancing the contractile performance of muscle cells and muscle tissue, preferably of striated muscle tissue, most preferably of cardiac and skeletal muscle cells and tissues. Since it is assumed that proper muscle function is tightly dependent on a functioning calcium handling within the muscle cell, the term "muscle function enhancing amino acid sequence" also refers to an amino acid sequence that is capable of enhancing and/or restoring the calcium handling/cycling, preferably the sarcoplasmic reticulum calcium handling/cycling in muscle cells, preferably skeletal muscle cells and/or cardiomyocytes. Contractile performance in myocytes can be directly measured, for example, by assessing single cardiomyocyte electrical field stimulated contractility using the video-edge-detection (VED) technique (Most et al., 2004, J. Clin. Invest. 114:1550-1563, page 1561). Calcium handling can be determined by assessing calcium transients using fluorescent calcium indicators (Most et al., 2004, J. Clin. Invest. 114: 1550-1563, page 1561).

The term "enhancing" in the context of the present invention, e.g., enhancing muscle function, contractile performance, and/or calcium handling, means that the particular function is increased/enhanced independently of whether the function is normal or defective, i.e., the muscle cell is healthy or diseased. Preferably, "enhancing" means that the particular function is enhanced by at least 15%, preferably by at least 25%, preferably by at least 35%, more preferably by at least 45%, and most preferably by at least 50% compared to a control setting. Preferably the control setting is the muscle function, contractile performance, and/or calcium handling of a healthy patient or the average of a group of healthy patients.

The term "restoring" in the context of the present invention, e.g., restoring muscle function, contractile performance, and/or calcium handling, preferably means that a defective function is brought back to at least 50% of the normal function, preferably to at least 60% of the normal function, preferably to at least 70% of the normal function, more preferably to at least 80% of the normal function, more preferably to at least 85% of normal function, even more preferably to at least 90% of the normal function, even more preferably to at least 95% of the normal function, and most preferably to at least 100% of the normal function, wherein "normal function" means an average value of the function exhibited by muscle cells derived from an individual who does not suffer from any muscle diseases. For example, in left ventricular catheterization, force development is assessed by the first derivative of pressure rise in the left ventricle, +dp/dt [mmHg/sec], in echocardiography, contractile performance is assessed by fractional shortening (FS %) in M-Mode or the calculated ejection fraction (EF %) (Most et al., 2004, J. Clin. Invest. 114: 1550-1563; Most et al., 2006, Circulation 114, 1258-1268, Material and Methods in on-line supplement), in VED, contractility is assessed by fractional shortening (FS %) and velocity of contraction (µm/sec). Calcium cycling can only be assessed in single cells—if calibrated—it is measured in nM free calcium concentrations. Roughly "normal" +dp/dt in anesthetized mice can range from 5000-8000 mmHg/sec, "normal" Echo EF % 60-80%/FS % 40-70%, "normal" cellular FS % can range from 5-12% and calibrated calcium transients might range from 200 to 400 nM.

The term "inotropic action" with respect to an agent means that said agent affects the force of muscle contraction irrespective of the muscle type. "Positive inotropic action" means that the force of muscle contraction is increased, wherein "negative inotropic action" means that the force of muscle contraction is decreased. A positive inotropic peptide of the present invention exhibits a positive inotropic action, preferably in vitro as well as in vivo. The inotropic effect of an agent, e.g., of the peptide of the present invention, can be readily determined in vitro, for example, by determining calcium transients in stimulated myocytes with and without the agent/peptide to be tested. For example, calcium transients can be assessed in FURA2-AM field-stimulated cardiomyocytes employing epifluorescence digitalized microscopy (Most et al., 2004, J. Clin. Invest. 114: 1550-1563, page 1561). Any fluorescent calcium indicator can be used instead of FURA-2AM such as a member of the Fluo calcium indicator family or Rhod-2AM. The underlying principal remains the same. Alternatively, calcium transient measurements in patch-clamped isolated cardiomyocytes (Kettlewell/Most et al., 2005, J. Mol. Cell. Cardiol., 200: 900-910, page 901) may also be used. The positive inotropic effect of a peptide can also be tested in vivo, for example, by determining the contractile performance by left ventricular catherization in anesthetized mice with and without administration of the peptide. Usually, in this experiment, contractility is described as the first derivative of maximal left ventricular pressure rise (+dp/dt max) (Most et al., 2004, J. Clin. Invest. 114: 1550-1563; Most et al., 2006, Circulation 114;1258-1268) Alternatively, echocardiography (Most et al., 2006, Circulation 114;1258-1268) can be used.

The term "enhancing and/or restoring calcium cycling" in the context of the present invention means that either calcium cycling in myocytes, preferably sarcoplasmic reticulum calcium cycling, is improved under normal/non-pathological conditions or restored to normal function as specified above under pathological conditions, i.e., if calcium cycling is defective. Defective calcium cycling may be a result of reduced calcium content in the sarcoplasmic reticulum, reduced release of calcium from the sarcoplasmic reticulum during excitation-contraction coupling, calcium leakage from the sarcoplasmic reticulum in quiescent muscle cells, for example, due to leaky RyR sarcoplasmic reticulum calcium release channels, increased calcium spark frequency, or reduced/slowed re-uptake of calcium into the sarcoplasmic reticulum and/or the mitochondria after contraction, for example, due to a malfunctioning or non-functioning sarcoplasmic/endoplasmic reticulum calcium ATPase (SERCA). Therefore, according to the present invention the calcium cycling can preferably be enhanced or restored by improving said parameters, e.g., increasing sarcoplasmic reticulum calcium content, increasing release of calcium from the sarcoplasmic reticulum during excitation-contraction coupling, reducing calcium leakage from the sarcoplasmic reticulum in quiescent muscle cells, reducing calcium spark frequency, and/or improving calcium re-uptake into the sarcoplasmic reticulum or the mitochondria. Without being bound to this theory, it is assumed that defective calcium cycling is one of the major reasons for defective contractile performance, e.g., contractile dysfunction, of muscle cells. Thus, it is assumed that enhancing or restoring calcium cycling also enhances and/or restores contractile performance In the context of the present invention, the term "contractile performance" encompasses any function that is associated with muscle contraction, for example, the force of muscle contraction or the timing of muscle contraction. In case of skeletal muscle tetanic contractions fall also within the term "contractile performance". "Defective contractile performance" refers to contractile dysfunction when compared to average values for normal/healthy muscle cells or tissue. For example, the contractile performance of a muscle cell or tissue is considered defective if, for example, the force of contraction of a given muscle cell or tissue deviates from the average value for normal/healthy muscle cells or tissue by at least 10%, preferably at least 20%, preferably at least 30%, more preferably at least 40%, and most preferably at least 50%, wherein the term "deviate" can refer to values less than the normal average value or to values higher than the normal average value, preferably it refers to values less than the normal average value. For example, for conscious humans an echocardiographic cardiac EF % below 50% is considered as beginning heart failure. Normal human cardiac conscious EF % is around 65-70%. Preferably, the term "enhancing and/or restoring contractile performance" means the increase of contractile force of muscle cells or tissue, preferably skeletal muscle cells or tissue or cardiac muscle cells or tissue, as well as the correction of defective timing of muscle cell contractions. In this context, the term "defective timing" refers to inappropriately timed muscle contraction events such as arrhythmias in the heart muscle or tremor or twitching of skeletal muscle tissue.

"Anti-arrhythmic potential" in the context of the peptide according to the present invention means that the peptide is capable of reducing inappropriately timed muscle contractions, i.e., arrhythmic events in myocytes, preferably in cardiomyocytes and cardiac tissue. The peptide of the present invention preferably protects cardiomyocytes from pro-arrhythmic store overload-induced calcium release (SOICR) which is a critical pathomechanism underlying arrhythmogenic sudden cardiac death, e.g., by lethal ventricular arrhythmias. In a preferred embodiment, the peptide according to the present invention combines the inotropic action with protection from arrhythmias, preferably calcium-induced arrhythmias in cardiomyocytes. The skilled person can readily determine whether a peptide exhibits anti-arrhythmic potency, for example, by assessing whether the peptide to be tested is capable of protecting cardiomyocytes, preferably ventricular cardiomyocytes, with leaky RyR2s sensitized to luminal calcium from βAR-triggered proarrhythmogenic SOICR and calcium waves. For example, normal ventricular cardiomyocytes may be treated with $10^{-7}$ M Isoproterenol and 0.5 mM caffeine with and without the peptide potentially exhibiting anti-arrhythmic potency and monitor the diastolic calcium concentration. In failing cardiomyocytes treatment with $10^{-7}$ M Isoproterenol or an equi-effective catecholamine (e.g., dobutamine, noradrenaline, adrenaline) alone can be used to unmask pro-arrhythmic molecular alterations with respect to calcium handling. In addition, other agents enhancing the β-adrenergic receptor downstream second messenger cyclic adenosine monophosphate (cAMP) such as phosphodiesterase inhibitors (rolipram, enoximon) at appropriate equi-effective dosages can be used with or without caffeine. SOICR can be identified by confocal microscopic calcium wave and spark measurements in fluorescent calcium indicator loaded quiescent cardiomyocytes (Voelkers et al., 2007, Cell Calcium 41:135-143, page 136) or as diastolic calcium waves/release in fluorescent calcium indicator loaded electrical field stimulated (Most et al., 2004, J. Clin. Invest. 114:1550-1563) and patch clamped (Kettlewell et al., 2005, J. Mol. Cell. Cardiol. 39:900-910, page 901) cardiomyocytes by epifluorescent microscopy. Alternatively, SOICR and calcium wave equivalents such as delayed or early after-contractions can be assessed by diastolic contractions in electrical field stimulated cardiomyocytes by VED (Most et al., 2004, J. Clin. Invest. 114:1550-1563).

In the context of the present invention, the term "carboxyterminal amino acids of an S100 protein" preferably refers to the carboxy-terminal 20 amino acids of an S100 protein, e.g., to amino acids 75 to 94 of the amino acid sequence set forth in SEQ ID NO: 38, i.e., the amino acid sequence Y-V-V-L-V-A-A-L-T-V-A-C-N-N-F-F-W-E-N-S (SEQ ID NO: 39), more preferably to the carboxy-terminal 25 amino acids of an S100 protein, and most preferably to the carboxy-terminal 30 amino acids of an S100 protein.

The term "capable of penetrating cell membranes" in the context of the peptide according to the present invention means that the peptide is able to traverse cell membranes of intact cells, wherein preferably the cell is a vertebrate cell, more preferably a mammalian cell, such as a mouse, rat, goat, sheep, dog, cat, pig, cow, or horse cell etc., most preferably a human cell, Preferably, a cell in the context of the present invention is a muscle cell, preferably a skeletal muscle cell or a cardiomyocyte. Thus, most preferably the cell in the context of the present invention is a mammalian muscle cell. The skilled person can readily assess whether a peptide is capable of penetrating cell membranes, e.g., by labeling said peptide, for example, with a radioactive or fluorescent marker, and incubating the labeled peptide with intact cells, preferably mammalian muscle cells, for example, rat ventricular cardiomyocytes, and assessing whether the labeled peptide can be detected inside the cells, for example, in the cytoplasm of the intact cells, e.g., by fluorescence microscopy (Most et al., 2005, J. Cell Sci. 118:421-431, page 422; Voelkers et al., 2007, Cell Calcium 41:135-143, page 136).

An S100 calcium binding protein in the context of the present invention is preferably selected from the group consisting of S100 calcium binding protein A1, S100 calcium binding protein Z, S100 calcium binding protein T, S100 calcium binding protein S, and the S100 protein α-chain. Most preferably the S100 calcium binding protein in the context of the present invention is S100 A1. The S100 calcium binding protein in the context of the present invention may be of any species, for example, human or other primate, mouse, or rat S100 protein etc, and is preferably of human origin. Preferred examples of S100 calcium binding proteins are those accessible by the following GenBank or Ref Seq accession numbers: XP_001494920.1, XP_001365057.1, XP_001140144, XP_513820.2, XP_001111052.1, CAI19674.1, XP_537265.1, NP_001092512.1, NP_006262.1, NP_001127319.1, AAB20539.2, NP_001007637.1, NP_035439.1, XP_002196029.1, XP_001332692.1, NP_001082820.1, XP_001504000.2, NP_570128.2, XP_526887.2, XP_226710.1, XP_607154.2, XP_853219.1, NP_001074628.1, NP_001013513.1, AAN63527.1, ACI68060.1, and XP_001344575.2.

In the context of the present invention the term "treating" a disease or disorder means that a disease condition is ameliorated independently whether the cause of the disease is eliminated, i.e., the individual having the disease is cured, or only the symptoms are diminished. Thus, even though it is assumed that the peptide according to the present invention exerts its therapeutic effects by stabilizing and/or restoring the calcium cycling/handling in muscle cells, and thereby, improving contractile performance of said cells, the peptide may also be used for the treatment of muscle diseases which are not caused by defective calcium cycling. For example, the symptoms of a skeletal muscle disorder, such as muscle weakness, which are not caused by or are not associated with defective calcium cycling in the muscle cells, are also diminished by the peptide according to the present invention.

The term "individual" in the context of the present invention preferably refers to an animal patient, preferably suffering from a cardiac muscle disorder or a skeletal muscle disorder or suffering from both. An animal patient is preferably a vertebrate patient, more preferably a mammalian patient, such as a domesticated animal, e.g., a mouse, rat, cat, guinea pig, rabbit, dog, pig, cow, or horse. Most preferably an animal patient is a human patient and the term "individual" refers to a human patient suffering from a muscle disorder, preferably from a cardiac muscle disorder and/or a skeletal muscle disorder. In the context of assessing functional features of the peptide according to the present invention, the term "individual" preferably refers to an experimental animal, such as a mouse, rat, rabbit, or primate, most preferably said term in this context refers to a heart failure animal model such as the post-myocardial infarction mouse or rat model (mouse: Most et al., 2006, Circulation 114:1258-1268, supplement; rat: Most et al., 2004, J. Clin. Invest. 114:1550-1563).

In a first aspect, the present invention provides a positive inotropic peptide comprising or consisting of a hydrophilic domain and/or one or more membrane penetration enhancing domains, and an S100A1 protein derived domain, wherein said S100A1 protein derived domain consists of 4 to 9 consecutive amino acids of the inotropic motif:

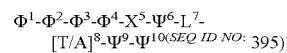

In a second aspect, the invention provides a positive inotropic peptide comprising or consisting of an S100A1 protein derived domain, wherein said S100A1 protein derived domain consists of 7 to 9 consecutive amino acids of the inotropic motif:

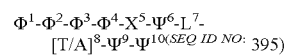

and comprises at least the core motif $\Phi^4\text{-}X^5\text{-}\Psi^6\text{-}L^7$ (SEQ ID NO: 396), wherein Φ and Ψ are in each instance an independently selected hydrophobic non-aromatic amino acid, and X is any amino acid, under the proviso that the N-terminal amino acid of said S100A protein derived domain consisting of 9 consecutive amino acids is $\Phi^1$, and wherein said peptide has a total length of maximally 100, preferably of maximally 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, or 95 amino acids. The positive inotropic peptide of the second aspect preferably exhibits a positive inotropic action. Furthermore, in the embodiment, wherein the S100A1 protein derived domain consists of 9 consecutive amino acids the amino acids are the following

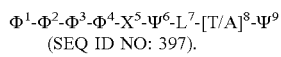
(SEQ ID NO: 397).

In a further preferred embodiments of the second aspect it is preferred that the N-terminal amino acid of said S100A protein derived domain consisting of 7 or 8 consecutive amino acids is $\Phi^1$, i.e. the S100A1 protein derived domain consists of
ti $\Phi^1$-$\Phi^2$-$\Phi^3$-$\Phi^4$-$X^5$-$\Psi^6$-$L^7$-$[T/A]^8$(SEQ ID NO:418)
or

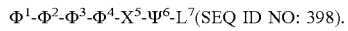

Thus, it is preferred that the proviso applies to S100A1 protein derived domain consisting of 7 to 9 consecutive amino acids.

In a preferred embodiment, the peptide of the first aspect has a length of between 10 and 80 amino acids, more preferably of between 10 and 70 amino acids, more preferably of between 10 and 60 amino acids, more preferably between 10 and 50 amino acids, even more preferably between 10 and 40 amino acids, even more preferably between 10 and 30 amino acids, most preferably the peptide has a length of between 10 and 15 amino acids. In a preferred embodiment, the peptide is 13, 14 or 15 amino acids long.

In a preferred embodiment, the peptide of the second aspect has a length of between 7 and 80 amino acids, more preferably of between 7 and 70 amino acids, more preferably of between 7 and 60 amino acids, more preferably between 7 and 50 amino acids, even more preferably between 7 and 40 amino acids, even more preferably between 7 and 30 amino acids, most preferably the peptide has a length of between 7 and 15 amino acids. In a preferred embodiment, the peptide is 7 to 9 or 7, 8, or 9 amino acids long.

Preferably, the peptide of the first or second aspect with the exception of the S100A1 protein derived domain as specified in the first or second aspect significantly differs from the carboxy-terminal amino acids of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the carboxy-terminus of any S100 calcium binding protein. More preferably, the peptide of the first or second aspect with the exception S100A1 protein derived domain significantly differs from the amino acid sequence of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the amino acid sequence of any S100 calcium binding protein. The term "significantly differs" means that the amino acid sequences are at least 80% different, more preferably at least 85%, more preferably at least 90%, even more preferably at least 95%, and most preferably 100% different. The difference in the sequences may be assessed by aligning the polypeptide sequences. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS::needle, Matrix: Blosum62, Gap Open 10.0, Gap Extend 0.5. Residues in two or more polypeptide sequences are said to differ from each other if the residues which are aligned in the best sequence alignment differ from each other. The "best sequence alignment" between two polypeptides is defined as the alignment that produces the largest number of aligned identical residues.

In a preferred embodiment of the peptide of the first aspect the peptide further comprises one or more of the elements selected from the group consisting of one or more epitope-tag(s), and a peptide targeting domain. It is also preferred that the peptide of the first aspect further comprises a hydrophilic domain, if it already comprised a membrane penetration enhancing domain or further comprises a membrane penetration enhancing domain, if it already comprised a hydrophilic domain. These further elements may be linked directly or indirectly to N- or C-terminally to the other elements of the peptide, preferably to the N-terminus of the hydrophilic domain or one or more membrane penetration enhancing domain.

In a preferred embodiment of the peptide of the second aspect the peptide further comprises one or more of the elements selected from the group consisting of a hydrophilic domain, a membrane penetration enhancing domain, one or more epitope-tag(s), and a peptide targeting domain, preferably a hydrophilic domain, a membrane penetration enhancing domain or a hydrophilic domain and a membrane penetration enhancing domain. These elements may be linked directly or indirectly to the N- or C-terminus of S100A1 protein derived domain. Preferably, to the N-terminus as described in more detail below.

For the purpose of the present invention two elements comprised in the positive inotropic peptides of the invention are "directly linked" if there is a peptide bond between an amino acid at the N-terminus of one element and an amino acid at the C-terminus of the other element. The term "indirectly linked" implies that there are one or more additional elements, preferably one or more amino acids between the respective N- and C-terminus of two elements. Such one, two, three, four or more amino acids are preferably linker. The term linker is used in the art to refer to a stretch of amino acids conferring flexibility. The skilled person is aware of a large number of linkers, which may be used in this context. Preferably the length of the linker does not exceed 1, 2, 3, 4, or 5 amino acids to keep the overall length of the positive inotropic peptide of the invention at a minimum.

Said hydrophilic domain preferably comprises acidic, basic, and/or otherwise negatively or positively charged amino acids. In a particular preferred embodiment of the peptide according to the present invention, the hydrophilic domain comprises or consists of the amino acid motif $\Lambda_4$-$\Theta_2$, wherein $\Lambda$ is in each instance independently selected from aspartate, glutamate, lysine, and arginine and $\Theta$ is an α-helix interrupter, preferably proline or glycine. Preferably, the hydrophilic domain comprises or consists of an amino acid sequence selected from the group consisting of [D/E]-[D/E]-[D/E]-[D/E]-[P/G]-[P/G] (SEQ ID NO:400), [K/R]-

[D/E]-[D/E]-[D/E]-[P/G]-[P/G] (SEQ ID NO:401), [D/E]-[K/R]-[D/E]-[D/E]-[P/G]-[P/G] (SEQ ID NO:402), [D/E]-[D/E]-[K/R]-[D/E]-[P/G]-[P/G] (SEQ ID NO:403), [D/E]-[D/E]-[D/E]-[K/R]-[P/G]-[P/G] (SEQ ID NO:404), [K/R]-[K/R]-[D/E]-[D/E]-[P/G]-[P/G] (SEQ ID NO:405), [K/R]-[D/E]-[K/R]-[D/E]-[P/G]-[P/G] (SEQ ID NO:406), [K/R]-[D/E]-[D/E]-[K/R]-[P/G]-[P/G] (SEQ ID NO:407), [D/E]-[K/R]-[K/R]-[D/E]-[P/G]-[P/G] (SEQ ID NO:408), [D/E]-[K/R]-[D/E]-[K/R]-[P/G]-[P/G] (SEQ ID NO:409), [D/E]-[D/E]-[K/R]-[K/R]-[P/G]-[P/G] (SEQ ID NO:410), [K/R]-[K/R]-[K/R]-[D/E]-[P/G]-[P/G] (SEQ ID NO:411), [K/R]-[K/R]-[D/E]- [K/R]-[P/G]-[P/G] (SEQ ID NO:412), [K/R]-[D/E]-[K/R]-[K/R]-[P/G]-[P/G] (SEQ ID NO:413), [D/E]-[K/R]-[K/R]-[K/R]-[P/G]-[P/G] (SEQ ID NO:414), and [K/R]-[K/R]-[K/R]-[K/R]-[P/G]-[P/G] (SEQ ID NO:415). Preferably, the hydrophilic domain comprises or consists of the amino acid sequence [D/E]-[K/R]-[D/E]-[D/E]-[P/G]-[P/G] (SEQ ID NO: 3). More preferably, the hydrophilic domain comprises or consists of an amino acid sequence selected from the group consisting of D-K-D-D-P-P (SEQ ID NO: 17), E-K-D-D-P-P (SEQ ID NO: 48), D-R-D-D-P-P (SEQ ID NO: 49), D-K-E-D-P-P (SEQ ID NO: 50), D-K-D-E-P-P (SEQ ID NO: 51), E-R-D-D-P-P (SEQ ID NO: 52), E-K-E-D-P-P (SEQ ID NO: 53), E-K-D-E-P-P (SEQ ID NO: 54), D-R-E-D-P-P (SEQ ID NO: 55), D-R-D-E-P-P (SEQ ID NO: 56), D-K-E-E-P-P (SEQ ID NO: 57), E-R-E-D-P-P (SEQ ID NO: 58), E-R-D-E-P-P (SEQ ID NO: 59), D-R-E-E-P-P (SEQ ID NO: 60), E-K-E-E-P-P (SEQ ID NO: 61), and E-R-E-E-P-P (SEQ ID NO: 62), wherein P-P in said sequences may be exchanged for G-G. Most preferably, the hydrophilic domain comprises or consists of the amino acid sequence D-K-D-D-P-P (SEQ ID NO: 17), wherein P-P in said sequences may also be G-G. Preferably, the hydrophilic domain is located within a peptide according to the present invention amino-terminally to the muscle function enhancing amino acid sequence, but could also be located carboxy-terminally to the muscle function enhancing amino acid sequence. In a particularly preferred embodiment, the C-terminus of said hydrophilic domain is directly or indirectly linked to the N-terminus of said inotropic domain and preferably the amino acid linked to said N-terminus is no hydrophobic non-aromatic amino acid.

Said membrane penetration enhancing domain may be any amino acid sequence that is capable of penetrating membranes as specified above, e.g., a cell-penetrating peptide (CCP). Such a domain may enable other macromolecules, such as peptides, proteins or nucleic acids, which normally do not possess the ability to traverse cell membranes, to penetrate intact cell membranes when said membrane penetration enhancing domain is attached to said macromolecule. Such membrane penetration enhancing domains may be derived from protein transduction domains, may be amphipathic peptides, or may be any other penetrating peptide. For example, the membrane penetration enhancing domain may be derived from the HIV Tat peptide, e.g. G-R-K-K-R-R-Q-R-R-R (SEQ ID NO: 63), the penetratin peptide, e.g. R-Q-I-K-I-W-F-Q-N-R-R-M-K-W-K-K (SEQ ID NO: 64) or K-K-W-K-M-R-R-N-Q-F-W-V-K-V-Q-R-G (SEQ ID NO: 65), the transportan peptide, e.g. G-W-T-L-N-S-A-G-Y-L-L-G-K-I-N-L-K-A-L-A-A-L-A-K-K-I-L (SEQ ID NO: 66), an MPG/Pep family member peptide, e.g. G-A-L-F-L-G-F-L-G-A-A-G-S-T-M-G-A-W-S-QP-K-K-K-R-K-V (SEQ ID NO: 67) or K-E-T-W-W-E-T-W-W-T-E-W-S-Q-P-K-K-K-R-K-V (SEQ ID NO: 68), or arginine rich peptides etc. (Deshayes et al., 2005, Cell. Mol. Life Sci. 62:1839-1849). Such a membrane penetration enhancing domain may be located amino-terminally or carboxy-terminally to the muscle function enhancing amino acid sequence within a peptide according to the present invention. Furthermore, a peptide according to the present invention may comprise more than one membrane penetration enhancing domain, for example, a peptide according to the present invention may contain 2, 3, 4, or 5 such domains.

In one embodiment, the peptide of the first aspect further comprises epitope-tag(s), and/or a peptide targeting domain. In another embodiment, the peptide of the first or second aspect further comprises one or more, e.g. one, two, three, or four of the elements selected from the group consisting of a hydrophilic domain, a membrane penetration enhancing domain, one or more epitope-tag(s), and a peptide targeting domain.

An epitope is a portion of a molecule to which an antibody binds. In the context of the present invention, an epitope is preferably a peptide-tag, for example, hemagglutinin-(HA-), FLAG-, myc-, or a poly-His-tag. Such an epitope tag may be used to locate the peptide of the present invention within a cell, for example, for determining whether the peptide penetrates, i.e., traverses, cell membranes and can be found inside an intact cell incubated with said peptide.

A peptide targeting domain in the context of the present invention may be any moiety that is suitable for targeting a peptide in vivo to a specific organ or specific cells. For example, a peptide targeting domain may be a peptide that specifically binds to a particular receptor which is specific for certain cells or a certain organ. Preferably, the presence of a peptide targeting domain within the peptide according to the present invention allows for specific targeting of cells or organs in a patient to which the peptide was administered systemically.

In a preferred embodiment, the core motif of the peptide of the first or second aspect is [V/I/M]-[A/G/S]-[A/V]-L (SEQ ID NO: 1). Preferably, said core motif is selected from the group consisting of the amino acid sequences V-G-A-L (SEQ ID NO: 4), I-A-A-L (SEQ ID NO: 5), V-S-V-L (SEQ ID NO: 6), M-G-A-L (SEQ ID NO: 7), V-A-A-L (SEQ ID NO: 8), and preferably is V-A-A-L (SEQ ID NO: 8).

In another preferred embodiment, the inotropic motif of the peptide of the first or second aspect is [V/I]-[V/I]-[L/M]-[V/I/M]-[A/G/S]-[A/V]-L-[T/A]-[V/A/I]-[A/M/V] (SEQ ID NO: 2). Preferably, said inotropic motif is selected from the group consisting of the amino acid sequences V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-V-L-I-A-A-L-A-A-A (SEQ ID NO: 13), V-I-L-V-S-V-L-T-V-A (SEQ ID NO: 14), I-I-L-M-G-A-L-T-V-A (SEQ ID NO: 15), and V-V-M-V-A-A-L-T-V-V (SEQ ID NO: 16). Most preferably, said inotropic motif is V-V-L-V-A-A-L-T-V-A (SEQ ID NO: 9).

Ψ of the inotropic motif of the peptide of the first or second aspect is preferably in each instance independently selected from the group consisting of alanine, methionine, isoleucine, leucine, and valine, preferably alanine, methionine, isoleucine, and valine. Φ of the inotropic motif of the peptide of the first or second aspect is preferably in each instance independently selected from the group consisting of alanine, methionine, isoleucine, leucine, and valine, preferably methionine, isoleucine, leucine, and valine. In a particularly preferred embodiment of the peptide of the first or second aspect, Φ is in each instance independently selected from methionine, isoleucine, leucine, and valine, and Ψ is in each instance independently selected from alanine, methionine, isoleucine, and valine.

In another preferred embodiment of the peptide of the first or second aspect, X is a small amino acid, wherein the small amino acid is preferably not proline. Preferably, X is selected from the group of amino acids consisting of glycine, alanine, serine, cysteine, threonine, and valine, more preferably X is selected from the group consisting of glycine, alanine, and serine. In a particularly preferred embodiment of the peptide of the first or second aspect, Φ is in each instance independently selected from methionine, isoleucine, leucine, and valine, Ψ is in each instance independently selected from alanine, methionine, isoleucine, and valine, and X is selected from glycine, alanine, serine, cysteine, threonine, and valine, preferably from glycine, alanine, and serine.

In a preferred embodiment, the inotropic motif of the peptide of the first or second aspect comprises or consists of an amino acid sequence selected from the group consisting of V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-I-L-V-S-V-L-T-V-A (SEQ ID NO: 14), V-V-M-V-A-A-L-T-V-V (SEQ ID NO: 16), V-V-L-I-A-A-L-T-V-A (SEQ ID NO: 69), V-V-L-M-A-A-L-T-V-A (SEQ ID NO: 70), V-V-L-V-G-A-L-T-V-A (SEQ ID NO: 71), V-V-L-V-S-A-L-T-V-A (SEQ ID NO: 72), V-V-L-V-A-V-L-T-V-A (SEQ ID NO: 73), V-V-L-V-A-A-L-A-V-A (SEQ ID NO: 74), V-V-L-V-A-A-L-T-A-A (SEQ ID NO: 75), V-V-L-V-A-A-L-T-I-A (SEQ ID NO: 76), V-V-L-V-A-A-L-T-V-M (SEQ ID NO: 77), V-V-L-V-A-A-L-T-V-V (SEQ ID NO: 78), I-I-L-V-A-A-L-T-V-A (SEQ ID NO: 79), I-V-M-V-A-A-L-T-V-A (SEQ ID NO: 80), I-V-L-I-A-A-L-T-V-A (SEQ ID NO: 81), I-V-L-M-A-A-L-T-V-A (SEQ ID NO: 82), I-V-L-V-G-A-L-T-V-A (SEQ ID NO: 83), I-V-L-V-S-A-L-T-V-A (SEQ ID NO: 84), I-V-L-V-A-V-L-T-V-A (SEQ ID NO: 85), I-V-L-V-A-A-L-A-V-A (SEQ ID NO: 86), I-V-L-V-A-A-L-T-A-A (SEQ ID NO: 87), I-V-L-V-A-A-L-T-I-A (SEQ ID NO: 88), I-V-L-V-A-A-L-T-V-M (SEQ ID NO: 89), I-V-L-V-A-A-L-T-V-V (SEQ ID NO: 90), V-I-M-V-A-A-L-T-V-A (SEQ ID NO: 91), V-I-L-I-A-A-L-T-V-A (SEQ ID NO: 92), V-I-L-M-A-A-L-T-V-A (SEQ ID NO: 93), V-I-L-V-G-A-L-T-V-A (SEQ ID NO: 94), V-I-L-V-S-A-L-T-V-A (SEQ ID NO: 95), V-I-L-V-A-V-L-T-V-A (SEQ ID NO: 96), V-I-L-V-A-A-L-A-V-A (SEQ ID NO: 97), V-I-L-V-A-A-L-T-A-A (SEQ ID NO: 98), V-I-L-V-A-A-L-T-I-A (SEQ ID NO: 99), V-I-L-V-A-A-L-T-V-M (SEQ ID NO: 100), V-I-L-V-A-A-L-T-V-V (SEQ ID NO: 101), V-V-M-I-A-A-L-T-V-A (SEQ ID NO: 102), V-V-M-M-A-A-L-T-V-A (SEQ ID NO: 103), V-V-M-V-G-A-L-T-V-A (SEQ ID NO: 104), V-V-M-V-S-A-L-T-V-A (SEQ ID NO: 105), V-V-M-V-A-V-L-T-V-A (SEQ ID NO: 106), V-V-M-V-A-A-L-A-V-A (SEQ ID NO: 107), V-V-M-V-A-A-L-T-A-A (SEQ ID NO: 108), V-V-M-V-A-A-L-T-I-A (SEQ ID NO: 109), V-V-M-V-A-A-L-T-V-M (SEQ ID NO: 110), V-V-L-I-G-A-L-T-V-A (SEQ ID NO: 111), V-V-L-I-S-A-L-T-V-A (SEQ ID NO: 112), V-V-L-I-A-V-L-T-V-A (SEQ ID NO: 113), V-V-L-I-A-A-L-A-V-A (SEQ ID NO: 114), V-V-L-I-A-A-L-T-A-A (SEQ ID NO: 115), V-V-L-I-A-A-L-T-I-A (SEQ ID NO: 116), V-V-L-I-A-A-L-T-V-M (SEQ ID NO: 117), V-V-L-I-A-A-L-T-V-V (SEQ ID NO: 118), V-V-L-M-G-A-L-T-V-A (SEQ ID NO: 119), V-V-L-M-S-A-L-T-V-A (SEQ ID NO: 120), V-V-L-M-A-V-L-T-V-A (SEQ ID NO: 121), V-V-L-M-A-A-L-A-V-A (SEQ ID NO: 122), V-V-L-M-A-A-L-T-A-A (SEQ ID NO: 123), V-V-L-M-A-A-L-T-I-A (SEQ ID NO: 124), V-V-L-M-A-A-L-T-V-M (SEQ ID NO: 125), V-V-L-M-A-A-L-T-V-V (SEQ ID NO: 126), V-V-L-V-G-V-L-T-V-A (SEQ ID NO: 127), V-V-L-V-G-A-V-V-A (SEQ ID NO: 128), V-V-L-V-G-A-L-T-A-A (SEQ ID NO: 129), V-V-L-V-G-A-L-T-I-A (SEQ ID NO: 130), V-V-L-V-G-A-L-T-V-M (SEQ ID NO: 131), V-V-L-V-G-A-L-T-V-V (SEQ ID NO: 132), V-V-L-V-S-V-L-T-V-A (SEQ ID NO: 133), V-V-L-V-S-A-L-A-V-A (SEQ ID NO: 134), V-V-L-V-S-A-L-T-A-A (SEQ ID NO: 135), V-V-L-V-S-A-L-T-I-A (SEQ ID NO: 136), V-V-L-V-S-A-L-T-V-M (SEQ ID NO: 137), V-V-L-V-S-A-L-T-V-V (SEQ ID NO: 138), V-V-L-V-A-V-L-A-V-A (SEQ ID NO: 139), V-V-L-V-A-V-L-T-A-A (SEQ ID NO: 140), V-V-L-V-A-V-L-T-I-A (SEQ ID NO: 141), V-V-L-V-A-V-L-T-V-M (SEQ ID NO: 142), V-V-L-V-A-V-L-T-V-V (SEQ ID NO: 143), V-V-L-V-A-A-L-A-A-A (SEQ ID NO: 144), V-V-L-V-A-A-L-A-I-A (SEQ ID NO: 145), V-V-L-V-A-A-L-A-V-M (SEQ ID NO: 146), V-V-L-V-A-A-L-A-V-V (SEQ ID NO: 147), V-V-L-V-A-A-L-T-A-M (SEQ ID NO: 148), V-V-L-V-A-A-L-T-A-V (SEQ ID NO: 149), V-V-L-V-A-A-L-T-I-M (SEQ ID NO: 150), V-V-L-V-A-A-L-T-I-V (SEQ ID NO: 151), I-I-M-V-A-A-L-T-V-A (SEQ ID NO: 152), I-I-L-I-A-A-L-T-V-A (SEQ ID NO: 153), I-I-L-M-A-A-L-T-V-A (SEQ ID NO: 154), I-I-L-V-S-A-L-T-V-A (SEQ ID NO: 155), I-I-L-V-A-V-L-T-V-A (SEQ ID NO: 156), I-I-L-V-A-A-L-A-V-A (SEQ ID NO: 157), I-I-L-V-A-A-L-T-A-A (SEQ ID NO: 158), I-I-L-V-A-A-L-T-I-A (SEQ ID NO: 159), I-I-L-V-A-A-L-T-V-M (SEQ ID NO: 160), I-I-L-V-A-A-L-T-V-V (SEQ ID NO: 161), I-V-M-I-A-A-L-T-V-A (SEQ ID NO: 162), I-V-M-M-A-A-L-T-V-A (SEQ ID NO: 163), I-V-M-V-G-A-L-T-V-A (SEQ ID NO: 164), I-V-M-V-S-A-L-T-V-A (SEQ ID NO: 165), I-V-M-V-A-V-L-T-V-A (SEQ ID NO: 166), I-V-M-V-A-A-L-A-V-A (SEQ ID NO: 167), I-V-M-V-A-A-L-T-A-A (SEQ ID NO: 168), I-V-M-V-A-A-L-T-I-A (SEQ ID NO: 169), I-V-M-V-A-A-L-T-V-M (SEQ ID NO: 170), I-V-M-V-A-A-L-T-V-V (SEQ ID NO: 171), I-V-L-I-G-A-L-T-V-A (SEQ ID NO: 172), I-V-L-I-S-A-L-T-V-A (SEQ ID NO: 173), I-V-L-I-A-V-L-T-V-A (SEQ ID NO: 174), I-V-L-I-A-A-L-A-V-A (SEQ ID NO: 175), I-V-L-I-A-A-L-T-A-A (SEQ ID NO: 176), I-V-L-I-A-A-L-T-I-A (SEQ ID NO: 177), I-V-L-I-A-A-L-T-V-M (SEQ ID NO: 178), I-V-L-I-A-A-L-T-V-V (SEQ ID NO: 179), I-V-L-M-G-A-L-T-V-A (SEQ ID NO: 180), I-V-L-M-S-A-L-T-V-A (SEQ ID NO: 181), I-V-L-M-A-V-L-T-V-A (SEQ ID NO: 182), I-V-L-M-A-A-L-A-V-A (SEQ ID NO: 183), I-V-L-M-A-A-L-T-A-A (SEQ ID NO: 184), I-V-L-M-A-A-L-T-I-A (SEQ ID NO: 185), I-V-L-M-A-A-L-T-V-M (SEQ ID NO: 186), I-V-L-M-A-A-L-T-V-V (SEQ ID NO: 187), I-V-L-V-G-V-L-T-V-A (SEQ ID NO: 188), I-V-L-V-G-A-L-A-V-A (SEQ ID NO: 189), I-V-L-V-G-A-L-T-A-A (SEQ ID NO: 190), I-V-L-V-G-A-L-T-I-A (SEQ ID NO: 191), I-V-L-V-G-A-L-T-V-M (SEQ ID NO: 192), I-V-L-V-G-A-L-T-V-V (SEQ ID NO: 193), I-V-L-V-S-V-L-T-V-A (SEQ ID NO: 194), I-V-L-V-S-A-L-A-V-A (SEQ ID NO: 195), I-V-L-V-S-A-L-T-A-A (SEQ ID NO: 196), I-V-L-V-S-A-L-T-I-A (SEQ ID NO: 197), I-V-L-V-S-A-L-T-V-M (SEQ ID NO: 198), I-V-L-V-S-A-L-T-V-V (SEQ ID NO: 199), I-V-L-V-A-V-L-A-V-A (SEQ ID NO: 200), I-V-L-V-A-V-L-T-A-A (SEQ ID NO: 201), I-V-L-V-A-V-L-T-I-A (SEQ ID NO: 202), I-V-L-V-A-V-L-T-V-M (SEQ ID NO: 203), I-V-L-V-A-V-L-T-V-V (SEQ ID NO: 204), I-V-L-V-A-A-L-A-A-A (SEQ ID NO: 205), I-V-L-V-A-A-L-A-I-A (SEQ ID NO: 206), I-V-L-V-A-A-L-A-V-M (SEQ ID NO: 207), I-V-L-V-A-A-L-A-V-V (SEQ ID NO: 208), I-V-L-V-A-A-L-T-A-M (SEQ ID NO: 209), I-V-L-V-A-A-L-T-A-V (SEQ ID NO: 210), I-V-L-V-A-A-L-T-I-M (SEQ ID NO: 211), I-V-L-V-A-A-L-T-I-V (SEQ ID NO: 212), V-I-M-I-A-A-L-T-V-A (SEQ ID NO: 213), V-I-M-M-A-A-L-T-V-A (SEQ ID NO: 214), V-I-M-V-G-A-L-T-V-A (SEQ ID NO: 215), V-I-M-V-S-A-L-T-V-A (SEQ ID NO: 216), V-I-M-V-A-V-L-T-V-A (SEQ ID NO: 217), V-I-M-V-A-A-L-A-V-A (SEQ ID NO: 218), V-I-M-V-A-A-L-T-A-A (SEQ ID NO: 219), V-I-

M-V-A-A-L-T-I-A (SEQ ID NO: 220), V-I-M-V-A-A-L-T-V-M (SEQ ID NO: 221), V-I-M-V-A-A-L-T-V-V (SEQ ID NO: 222), V-I-L-I-G-A-L-T-V-A (SEQ ID NO: 223), V-I-L-I-S-A-L-T-V-A (SEQ ID NO: 224), V-I-L-I-A-V-L-T-V-A (SEQ ID NO: 225), V-I-L-I-A-A-L-A-V-A (SEQ ID NO: 226), V-I-L-I-A-A-L-T-A-A (SEQ ID NO: 227), V-I-L-I-A-A-L-T-I-A (SEQ ID NO: 228), V-I-L-I-A-A-L-T-V-M (SEQ ID NO: 229), V-I-L-I-A-A-L-T-V-V (SEQ ID NO: 230), V-I-L-M-G-A-L-T-V-A (SEQ ID NO: 231), V-I-L-M-S-A-L-T-V-A (SEQ ID NO: 232), V-I-L-M-A-V-L-T-V-A (SEQ ID NO: 233), V-I-L-M-A-A-L-A-V-A (SEQ ID NO: 234), V-I-L-M-A-A-L-T-A-A (SEQ ID NO: 235), V-I-L-M-A-A-L-T-I-A ((SEQ ID NO: 236), V-I-L-M-A-A-L-T-V-M (SEQ ID NO: 237), V-I-L-M-A-A-L-T-V-V ((SEQ ID NO: 238), V-I-L-V-G-V-L-T-V-A (SEQ ID NO: 239), V-I-L-V-G-A-L-A-V-A ((SEQ ID NO: 240), V-I-L-V-G-A-L-T-A-A (SEQ ID NO: 241), V-I-L-V-G-A-L-T-I-A ((SEQ ID NO: 242), V-I-L-V-G-A-L-T-V-M (SEQ ID NO: 243 ), V-I-L-V-G-A-L-T-V-V ((SEQ ID NO: 244), V-I-L-V-S-A-L-A-V-A ((SEQ ID NO: 245), V-I-L-V-S-A-L-T-A-A ((SEQ ID NO: 246), V-I-L-V-S-A-L-T-I-A ((SEQ ID NO: 247), V-I-L-V-S-A-L-T-V-M ((SEQ ID NO: 248), V-I-L-V-S-A-L-T-V-V ((SEQ ID NO: 249), V-I-L-V-A-V-L-A-V-A ((SEQ ID NO: 250), V-I-L-V-A-V-L-T-A-A ((SEQ ID NO: 251), V-I-L-V-A-V-L-T-I-A (SEQ ID NO: 252), V-I-L-V-A-V-L-T-V-M ((SEQ ID NO: 253), V-I-L-V-A-V-L-T-V-V (SEQ ID NO: 254), V-I-L-V-A-A-L-A-A-A ((SEQ ID NO: 255), V-I-L-V-A-A-L-A-I-A (SEQ ID NO: 256), V-I-L-V-A-A-L-A-V-M ((SEQ ID NO: 257), V-I-L-V-A-A-L-A-V-V (SEQ ID NO: 258), V-I-L-V-A-A-L-T-A-M (SEQ ID NO: 259), V-I-L-V-A-A-L-T-A-V (SEQ ID NO: 260), V-I-L-V-A-A-L-T-I-M (SEQ ID NO: 261), V-I-L-V-A-A-L-T-I-V (SEQ ID NO: 262), V-V-M-I-G-A-L-T-V-A (SEQ ID NO: 263), V-V-M-I-S-A-L-T-V-A (SEQ ID NO: 264), V-V-M-I-A-V-L-T-V-A (SEQ ID NO: 265), V-V-M-I-A-A-L-A-V-A (SEQ ID NO: 266), V-V-M-I-A-A-L-T-A-A (SEQ ID NO: 267), V-V-M-I-A-A-L-T-I-A (SEQ ID NO: 268), V-V-M-I-A-A-L-T-V-M (SEQ ID NO: 269), V-V-M-I-A-A-L-T-V-V (SEQ ID NO: 270), V-V-M-M-G-A-L-T-V-A (SEQ ID NO: 271), V-V-M-M-S-A-L-T-V-A (SEQ ID NO: 272), V-V-M-M-A-V-L-T-A (SEQ ID NO: 273), V-V-M-M-A-A-L-A-V-A (SEQ ID NO: 274 ), V-V-M-M-A-A-L-T-A-A (SEQ ID NO: 275), V-V-M-M-A-A-L-T-I-A (SEQ ID NO: 276), V-V-M-M-A-A-L-T-V-M (SEQ ID NO: 277), V-V-M-M-A-A-L-T-V-V (SEQ ID NO: 278), V-V-M-V-G-V-L-T-V-A (SEQ ID NO: 279), V-V-M-V-G-A-L-A-V-A (SEQ ID NO: 280), V-V-M-V-G-A-L-T-A-A (SEQ ID NO: 281), V-V-M-V-G-A-L-T-I-A (SEQ ID NO: 282), V-V-M-V-G-A-L-T-V-M (SEQ ID NO: 283), V-V-M-V-G-A-L-T-V-V (SEQ ID NO: 284), V-V-M-V-S-V-L-T-V-A (SEQ ID NO: 285), V-V-M-V-S-A-L-A-V-A (SEQ ID NO: 286), V-V-M-V-S-A-L-T-A-A (SEQ ID NO: 287 ), V-V-M-V-S-A-L-T-I-A (SEQ ID NO: 288), V-V-M-V-S-A-L-T-V-M (SEQ ID NO: 289), V-V-M-V-S-A-L-T-V-V (SEQ ID NO: 290), V-V-M-V-A-V-L-A-V-A (SEQ ID NO: 291), V-V-M-V-A-V-L-T-A-A (SEQ ID NO: 292), V-V-M-V-A-V-L-T-I-A (SEQ ID NO: 293), V-V-M-V-A-V-L-T-V-M (SEQ ID NO: 294), V-V-M-V-A-V-L-T-V-V (SEQ ID NO: 295), V-V-M-V-A-A-L-A-A-A (SEQ ID NO: 296), V-V-M-V-A-A-L-A-I-A (SEQ ID NO: 297), V-V-M-V-A-A-L-A-V-M (SEQ ID NO: 298), V-V-M-V-A-A-L-A-V-V (SEQ ID NO: 299), V-V-M-V-A-A-L-T-A-M (SEQ ID NO: 300), V-V-M-V-A-A-L-T-A-V (SEQ ID NO: 301), V-V-M-V-A-A-L-T-I-M (SEQ ID NO: 302), V-V-M-V-A-A-L-T-I-V (SEQ ID NO: 303), V-V-L-I-G-V-L-T-V-A (SEQ ID NO: 304), V-V-L-I-G-A-L-A-V-A (SEQ ID NO: 305), V-V-L-I-G-A-L-T-A-A (SEQ ID NO: 306), V-V-L-I-G-A-L-T-I-A (SEQ ID NO: 307), V-V-L-I-G-A-L-T-V-M (SEQ ID NO: 308), V-V-L-I-G-A-L-T-V-V (SEQ ID NO: 309), V-V-L-I-S-V-L-T-V-A (SEQ ID NO: 310), V-V-L-I-S-A-L-A-V-A (SEQ ID NO: 311), V-V-L-I-S-A-L-T-A-A (SEQ ID NO: 312), V-V-L-I-S-A-L-T-I-A (SEQ ID NO: 313), V-V-L-I-S-A-L-T-V-M (SEQ ID NO: 314), V-V-L-I-S-A-L-T-V-V (SEQ ID NO: 315), V-V-L-I-A-V-L-A-V-A (SEQ ID NO: 316), V-V-L-I-A-V-L-T-A-A (SEQ ID NO: 317), V-V-L-I-A-V-L-T-I-A (SEQ ID NO: 318), V-V-L-I-A-V-L-T-V-M (SEQ ID NO: 319), V-V-L-I-A-V-L-T-V-V (SEQ ID NO: 320), V-V-L-I-A-A-L-A-A-A (SEQ ID NO: 13), V-V-L-I-A-A-L-A-I-A (SEQ ID NO: 321), V-V-L-I-A-A-L-A-V-M (SEQ ID NO: 322), V-V-L-I-A-A-L-A-V-V (SEQ ID NO: 323), V-V-L-I-A-A-L-T-A-M (SEQ ID NO: 324), V-V-L-I-A-A-L-T-A-V (SEQ ID NO: 325), V-V-L-I-A-A-L-T-I-M (SEQ ID NO: 326), V-V-L-I-A-A-L-T-I-V (SEQ ID NO: 327), V-V-L-M-G-V-L-T-V-A (SEQ ID NO: 328), V-V-L-M-G-A-L-A-V-A (SEQ ID NO: 329), V-V-L-M-G-A-L-T-A-A (SEQ ID NO: 330), V-V-L-M-G-A-L-T-I-A (SEQ ID NO: 331), V-V-L-M-G-A-L-T-V-M (SEQ ID NO: 332), V-V-L-M-G-A-L-T-V-V (SEQ ID NO: 333), V-V-L-M-S-V-L-T-V-A (SEQ ID NO: 334), V-V-L-M-S-A-L-A-V-A (SEQ ID NO: 335), V-V-L-M-S-A-L-T-A-A (SEQ ID NO: 336), V-V-L-M-S-A-L-T-I-A (SEQ ID NO: 337), V-V-L-M-S-A-L-T-V-M (SEQ ID NO: 338), V-V-L-M-S-A-L-T-V-V (SEQ ID NO: 339), V-V-L-M-A-V-L-A-V-A (SEQ ID NO: 340), V-V-L-M-A-V-L-T-A-A (SEQ ID NO: 341), V-V-L-M-A-V-L-T-I-A (SEQ ID NO: 342), V-V-L-M-A-V-L-T-V-M (SEQ ID NO: 343), V-V-L-M-A-V-L-T-V-V (SEQ ID NO: 344), V-V-L-M-A-A-L-A-A-A (SEQ ID NO: 345), V-V-L-M-A-A-L-A-I-A (SEQ ID NO: 346), V-V-L-M-A-A-L-A-V-M (SEQ ID NO: 347), V-V-L-M-A-A-L-A-V-V (SEQ ID NO: 348), V-V-L-V-G-V-L-A-V-A (SEQ ID NO: 349), V-V-L-V-G-V-L-T-A-A (SEQ ID NO: 350), V-V-L-V-G-V-L-T-I-A (SEQ ID NO: 351), V-V-L-V-G-V-L-T-V-M (SEQ ID NO: 352), V-V-L-V-G-V-L-T-V-V (SEQ ID NO: 353), V-V-L-V-G-A-L-A-A-A (SEQ ID NO: 354), V-V-L-V-G-A-L-A-I-A (SEQ ID NO: 355), V-V-L-V-G-A-L-A-V-M (SEQ ID NO: 356), V-V-L-V-G-A-L-A-V-V (SEQ ID NO: 357), V-V-L-V-G-A-L-T-A-M (SEQ ID NO: 358), V-V-L-V-G-A-L-T-A-V (SEQ ID NO: 359), V-V-L-V-G-A-L-T-I-M (SEQ ID NO: 360), V-V-L-V-G-A-L-T-I-V (SEQ ID NO: 361), V-V-L-V-S-V-L-A-V-A (SEQ ID NO: 362), V-V-L-V-S-V-L-T-A-A (SEQ ID NO: 363), V-V-L-V-S-V-L-T-I-A (SEQ ID NO: 364), V-V-L-V-S-V-L-T-V-M (SEQ ID NO: 365), V-V-L-V-S-V-L-T-V-V (SEQ ID NO: 366), V-V-L-V-S-A-L-A-A-A (SEQ ID NO: 367), V-V-L-V-S-A-L-A-I-A (SEQ ID NO: 368), V-V-L-V-S-A-L-A-V-M (SEQ ID NO: 369), V-V-L-V-S-A-L-A-V-A-V (SEQ ID NO: 370), V-V-L-V-S-A-L-T-A-M (SEQ ID NO: 371), V-V-L-V-S-A-L-T-A-V (SEQ ID NO: 372), V-V-L-V-S-A-L-T-I-M (SEQ ID NO: 373), V-V-L-V-S-A-L-T-I-V (SEQ ID NO: 374), V-V-L-V-A-V-L-A-A-A (SEQ ID NO: 375), V-V-L-V-A-V-L-A-I-A (SEQ ID NO: 376), V-V-L-V-A-V-L-A-V-M (SEQ ID NO: 377), V-V-L-V-A-V-L-A-V-V (SEQ ID NO: 378), V-V-L-V-A-V-L-T-A-M (SEQ ID NO: 379), V-V-L-V-A-V-L-T-A-V (SEQ ID NO: 380), V-V-L-V-A-V-L-T-I-M (SEQ ID NO: 381), V-V-L-V-A-V-L-T-I-V (SEQ ID NO: 382), V-V-L-V-A-A-L-A-A-M (SEQ ID NO: 383), V-V-L-V-A-A-L-A-A-V (SEQ ID NO: 384), V-V-L-V-A-A-L-A-I-M (SEQ ID NO: 385), V-V-L-V-A-A-L-A-I-V (SEQ ID NO: 386), V-V-L-M-A-A-L-T-A-M (SEQ ID NO: 390), V-V-L-M-A-A-L-T-A-V (SEQ ID NO: 391), V-V-L-M-A-A-L-T-I-M (SEQ ID NO: 392), V-V-L-M-A-A-L-T-I-V (SEQ ID NO: 393), and I-V-L-V-A-A-L-T-V-A (SEQ ID NO: 394). These amino acid sequences are preferred specific embodiments of the inotropic motif comprised in a peptide according to the present invention.

In another preferred embodiment, the inotropic motif comprises or consists of the amino acid sequence V-[V/I]-L-[V/I]-[A/S]-[A/V]-[T/A]-[V/A]-A (SEQ ID NO: 387), wherein the preferred sequence is V-V-L-V-A-A-L-T-V-A (SEQ ID NO: 9), wherein preferably maximally 4, more preferably maximally 3, even more preferably maximally 2, and most preferably maximally 1 amino acid is replaced as specified above. Thus, in a particularly preferred embodiment, the inotropic motif consists of the amino acid sequence V-[V/I]-L-[V/I]-[A/S]-[A/V]-L-[T/A]-[V/A]-A (SEQ ID NO: 387), wherein the preferred sequence is V-V-L-V-A-A-L-T-V-A (SEQ ID NO: 9), wherein preferably maximally 4, more preferably maximally 3, even more preferably maximally 2, and most preferably maximally 1 amino acid is replaced with another amino acid as specified above.

In a preferred embodiment, the inotropic motif comprises or consists of an amino acid sequence selected from the group consisting of the amino acid sequences V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-V-L-I-A-A-L-A-A-A (SEQ ID NO: 13), V-I-L-V-S-V-L-T-V-A (SEQ ID NO: 14), I-I-L-M-G-A-L-T-V-A (SEQ ID NO: 15), and V-V-M-V-A-A-L-T-V-V (SEQ ID NO: 16). These amino acid sequences are particularly preferred specific embodiments of the inotropic motif comprised in a peptide according to the present invention.

The S100A1 protein derived domain of the peptide of the first aspect is preferably selected from the group consisting of the amino acid sequences V-V-L-V-A-A-L-T-V (SEQ ID NO: 18), V-V-L-V-A-A-L-T (SEQ ID NO: 19), V-V-L-V-A-A-L (SEQ ID NO: 20), V-L-V-A-A-L-T-V-A (SEQ ID NO: 21), V-L-V-A-A-L-T-V (SEQ ID NO: 22), V-L-V-A-A-L-T (SEQ ID NO: 23), V-L-V-A-A-L (SEQ ID NO: 24), L-V-A-A-L-T-V-A (SEQ ID NO: 25), and L-V-A-A-L-T-V (SEQ ID NO: 26), L-V-A-A-L-T (SEQ ID NO: 27), L-V-A-A-L (SEQ ID NO: 28), V-A-A-L-T-V-A (SEQ ID NO: 29), V-A-A-L-T-V (SEQ ID NO: 30), V-A-A-L-T (SEQ ID NO: 31), and V-A-A-L (SEQ ID NO: 8).

In a most preferred embodiment, the peptide of the first aspect comprises or consists of an amino acid sequence selected from the group consisting of the amino acid sequences D-K-D-D-P-P-V-L-V-A-A-L-T-V-A (SEQ ID NO: 32), D-K-D-D-P-P-L-V-A-A-L-T-V-A (SEQ ID NO: 33), D-K-D-D-P-P-V-A-A-L-T-V-A (SEQ ID NO: 34), D-K-D-D-P-P-V-V-L-V-A-A-L-T-V (SEQ ID NO: 35), D-K-D-D-P-P-V-V-L-V-A-A-L-T (SEQ ID NO: 36), and D-K-D-D-P-P-V-V-L-V-A-A-L (SEQ ID NO: 37).

In another embodiment, the S100A1 protein derived domain of the peptide of the second aspect comprises or consists of an amino acid sequence selected from the group consisting of the amino acid sequences V-V-L-V-A-A-L-T-V (SEQ ID NO: 18), V-V-L-V-A-A-L-T (SEQ ID NO: 19), and V-V-L-V-A-A-L (SEQ ID NO: 20). Preferably, the peptide of the second aspect comprises or consists of an amino acid sequence selected from the group consisting of the amino acid sequences V-V-L-V-A-A-L-T-V (SEQ ID NO: 18), V-V-L-V-A-A-L-T (SEQ ID NO: 19), and V-V-L-V-A-A-L (SEQ ID NO: 20). Each of these peptides comprising or consisting of an amino acid sequence according to SEQ ID NOs 18 to 20 may further comprise the hydrophilic domain D-K-D-D-P-P linked to the N-terminal of said amino acid sequence.

The S100A1 protein derived domain of the peptides of the first or second aspect preferably is located at the C-terminus of the peptide of the first or second aspect. More preferably, said peptide do not contain more than 9 continuous amino acids comprised in the 20 amino acid C-terminus region of an S100A1 protein.

In another embodiment, the peptide of the first or second aspect further comprises a marker moiety. A marker moiety in the context of the present invention may be any moiety that allows for a straightforward detection of the peptide, such as a fluorescent label, e.g., fluorescein (for example, fluorescein isothiocyanate FITC), rhodamine (for example, tetramethylrhodamine TAMRA or its isothiocyanate derivative TRITC, sulforhodamine 101 and its sulfonylchloride form Texas Red™, and Rhodamine Red), or Alexa Fluor® dyes, a radioactive label, e.g., a radioactively labeled amino acid, or biotin. In one embodiment, the peptide of the present invention comprises a hydrophilic motif, preferably D-K-D-D-P-P (SEQ ID NO: 17), and a marker moiety, preferably FITC or rhodamine, wherein preferably the muscle function enhancing amino acid sequence is V-V-L-V-A-A-L-T-V-A (SEQ ID NO: 9), and preferably the hydrophilic motif is directly linked to the amino-terminus of the muscle function enhancing amino acid sequence.

In a preferred embodiment, the amino acid sequence of the peptides according to the present invention forms an α-helical structure.

In a particularly preferred embodiment, the peptides of the present invention are capable of penetrating cell membranes, preferably vertebrate cell membranes, even more preferably mammalian cell membranes, even more preferably mammalian muscle cell membranes, and most preferably mammalian skeletal muscle cell membranes and membranes of mammalian cardiomyocytes. Preferably, the peptides of the present invention are capable of penetrating cell membranes as defined above in a physiological environment such as in culture medium, for example, for mammalian tissue culture, and/or in body fluids such as in blood. Thus, most preferably, the peptides of the present invention are capable of penetrating cell membranes in vivo when it is administered by a parenteral administration route such as by intravenous injection.

In a preferred embodiment of the first aspect of the invention the S100A1 protein derived domain does not contain more than 9, 8, 7, 6, 5 or 4 continuous amino acids of the carboxy-terminal amino acids of an S100 calcium binding protein selected from the group consisting of S100 calcium binding protein A1, S100 calcium binding protein Z, S100 calcium binding protein T, S100 calcium binding protein S, and S100 protein α-chain, wherein the S100 calcium binding protein is preferably of human origin, most preferably of any species. Thus, preferably the S100A1 protein derived domain according to the present invention preferably do not contain more than 9, 8, 7, 6, 5 or 4 continuous amino acids of the carboxy-terminal amino acids of an S100 calcium binding protein A1, do not contain more than 9, 8, 7, 6, 5 or 4 continuous amino acids of the carboxy-terminal amino acids of an S100 calcium binding protein Z, do not contain more than 9, 8, 7, 6, 5 or 4 continuous amino acids of the carboxy-terminal amino acids of an S100 calcium binding protein T, do not contain more than 9, 8, 7, 6, 5 or 4 continuous amino acids of the carboxy-terminal amino acids of an S100 calcium binding protein S, and do not contain more than 9, 8, 7, 6, 5 or 4 continuous amino acids of the carboxy-terminal amino acids of an S100 protein alpha chain, wherein the S100 calcium binding protein is preferably of human origin, most preferably of any species. In a most preferred embodiment, the S100A1 protein derived domain of the present do not contain more than 9, 8, 7, 6, 5 or 4 continuous amino acids of the carboxy-terminal amino acids of any S100 calcium binding protein preferably of human origin, more preferably of any species.

In a preferred embodiment of the second aspect of the invention the S100A1 protein derived domain does not contain more than 9, 8, or 7 continuous amino acids of the carboxy-terminal amino acids of an S100 calcium binding protein selected from the group consisting of S100 calcium binding protein A1, S100 calcium binding protein Z, S100 calcium binding protein T, S100 calcium binding protein S, and S100 protein α-chain, wherein the S100 calcium binding protein is preferably of human origin, most preferably of any species. Thus, preferably the S100A1 protein derived domain according to the present invention preferably does not contain more than 9, 8, or 7 continuous amino acids of the carboxy-terminal amino acids of an S100 calcium binding protein A1, does not contain more than 9, 8, or 7 continuous amino acids of the carboxy-terminal amino acids of an S100 calcium binding protein Z, does not contain more than 9, 8, or 7 continuous amino acids of the carboxy-terminal amino acids of an S100 calcium binding protein T, does not contain more than 9, 8, or 7 continuous amino acids of the carboxy-terminal amino acids of an S100 calcium binding protein S, and does not contain more than 9, 8, or 7 continuous amino acids of the carboxy-terminal amino acids of an S100 protein alpha chain, wherein the S100 calcium binding protein is preferably of human origin, most preferably of any species. In a most preferred embodiment, the S100A1 protein derived domain of the present does not contain more than 9, 8, or 7 continuous amino acids of the carboxy-terminal amino acids of any S100 calcium binding protein preferably of human origin, more preferably of any species. As outlined above, it is preferred in this aspect that one, two of three of the most C-terminal amino acid of the respective S100 calcium binding protein are not included in the S100A1 protein derived domain.

In a particularly preferred embodiment, the peptides of the present invention exhibit the ability to enhance contractile performance and/or calcium cycling in myocytes, preferably in skeletal muscle cells or cardiomyocytes.

In a particularly preferred embodiment, the peptides of the present invention exhibit anti-arrhythmic potential on myocytes, preferably on cardiomyocytes, and thus, are preferably capable of protecting myocytes and heart tissue from arrhythmias, preferably from catecholamine triggered arrhythmias, preferably from ventricular arrhythmias which frequently are the cause of sudden cardiac death. Preferably, the peptides of the present invention exhibit the anti-arrhythmic potential in vitro as well as in vivo. Preferably, the peptides of the present invention exhibit the ability of protecting an individual from lethal ventricular tachyarrhythmias, preferably from β-adrenergic receptor (βAR) triggered lethal ventricular tachyarrhythmias, preferably from catecholamine triggered lethal ventricular tachyarrhythmias. Preferably, the in vivo anti-arrhythmic potential is observed when the peptides are administered via a parenteral administration route. The anti-arrhythmic potential of a peptide can be assessed in vitro, for example, by examining whether the peptide protects cardiomyocytes from SOICR as described above. The anti-arrhythmic potential of a peptide can be assessed in vivo, for example, by examining the effect of a treatment with the peptide on mortality caused by βAR triggered tachyarrhythmias in a heart failure animal model, for example, in a post myocardial infarction mouse model (Most et al., 2006, Circulation 114:1258-1268, supplement). For example, the peptide may be administered to mice with postischemic contractile dysfunction, preferably parenterally, such as intraperitoneally, intravenously, or subcutaneously, daily or every second day for several days, such as 6, 7, 8, or 9 days, up to a few weeks, such as 2, 3, or 4 weeks, preferably 2 weeks. The lethal ventricular tachyarrhythmias may be triggered in the animals after a certain period of treatment with the peptide, for example after 7, 8, 9, 10 days or after 2 weeks, by administration of epinephrine, e.g., at a concentration in the range of 1.5 to 2.5 mg/kg, preferably at a concentration of 2 mg/kg, in combination of caffeine, e.g., at a concentration in the range of 100 to 140 mg/kg, preferably at a concentration of 120 mg/kg. The lethal ventricular fibrillation may be monitored by telemetric ECG (cf., for example, Xiao et al., 2007, J. Biol. Chem. 282:34828-34838).

In another preferred embodiment, the peptides of the present invention have the ability to reduce calcium spark frequency in myocytes such as skeletal muscle cells and cardiomyocytes, preferably in cardiomyocytes. Preferably, the peptides of the present invention exhibit the ability to reduce calcium spark frequency in vitro as well as in vivo. Preferably, the in vivo effect is observed when the peptides are administered via a parenteral administration route. "Reducing" in this context preferably means that the calcium spark frequency in myocytes treated with a peptide is at least 15%, more preferably at least 25%, even more preferably at least 30%, and most preferably at least 40% reduced compared to control myocytes that have not been treated with the peptide. Preferably, this ability is dependent on the concentration of the peptide applied to the cardiomyocytes. Preferably, the peptides of the invention have the ability of reducing calcium spark frequency in intact cardiomyocytes when added to the liquid in which the cardiomyocytes are present. For example, the peptides of the present invention preferably reduce calcium spark frequency in quiescent cardiomyocytes, e.g., in cultured quiescent rat ventricular cardiomyocytes, when added to the medium of the cardiomyocytes at a concentration in the range of 50 nM to 500 nM, preferably, when applied at a concentration in the range of 50 nM to 250 nM, more preferably when applied at a concentration in the range of 75 to 150 nM, and most preferably when applied at 100 nM, whereas the calcium spark frequency is increased when applied at a concentration of 600 nM or higher, preferably at a concentration of 700 mM or higher, more preferably at a concentration of 800 nM or higher, even more preferably at a concentration of 900 nM or higher, and most preferably at a concentration of 1000 nM or higher (Voelkers M. et al., 2007, Cell Calcium 41:135-143). Thus, the skilled person can readily determine whether a peptide has the ability to reduce calcium spark frequency. In a particularly preferred embodiment, the peptides of the present invention exhibit an anti-arrhythmic potential and the ability to reduce calcium spark frequency as described above.

In another preferred embodiment, the peptides of the present invention protect myocytes, preferably skeletal muscle cells and/or cardiomyocytes from apoptotic cell death, preferably from calcium-induced apoptotic cell death, preferably from sarcoplasmic reticulum calcium leakage triggered apoptotic cell death. Thus, preferably, the peptides of the present invention exhibit anti-apoptotic potential. Preferably, the peptides of the present invention exhibit this anti-apoptotic effect in vitro as well as in vivo. Preferably, the peptides of the present invention prevent apoptotic cell death in failing myocardium in vivo, i.e., protect cardiomyocytes in failing myocardium from apoptotic cell death in vivo. Preferably, the in vivo protective effect is observed when a peptide is administered via a parenteral administration route. "Protecting" in this context means that the extent of apoptotic cell death is reduced in the cells treated with the peptide according to the present invention compared to a control group by at least 20%, preferably by at least 30%, more preferably by at least 40%, and even more preferably by at least 50%, and most preferably by at least 60%. The skilled person is able to test for this feature in vitro, for example, by observing the extent of apoptosis in myocytes, preferably in ventricular cardiomyocytes, with leaky RyR calcium release channels that are sensitized to luminal calcium by long-term caffeine exposure with and without the peptide. An indication for apoptosis is, for example, a fragmented genome which can be examined, e.g., by DNA laddering (Liu et al., 2005, Circulation 111:90-96), cytochrom-c release, or caspase 3 activity (Most et al., 2003, J. Biol. Chem. 278:48404-48412). The anti-apoptotic effect of a peptide may be assessed in vivo in an experimental heart failure animal model. For example, mice with postischemic contractile dysfunction may be treated with the peptide and cardiac tissue of treated and control mice may be assessed for the extent of apoptotic cardiomyocytes. The peptide may be administered preferably parenterally, such as intraperitoneally, intravenously, or subcutaneously, daily or every second day for several days, such as 6, 7, 8, or 9 days, up to a few weeks, such as 2, 3, or 4 weeks, preferably 2 weeks. The extent of apoptotic cells may be assessed by TUNEL staining of TnI and CD31 counterstained heart tissue sections (Most et al., 2006, Circulation 114:1258-1268). In a particularly preferred embodiment, the peptides of the invention exhibit anti-arrhythmic potential and protects myocytes from apoptotic cell death as described above.

In another preferred embodiment, the peptides of the present invention have the ability to prevent and/or reduce calcium leakage from the sarcoplasmic reticulum, preferably in quiescent myocytes such as skeletal muscle cells and cardiomyocytes. Preferably, the peptides of the present invention exhibit this effect in vitro and in vivo. Preferably, this in vivo effect is observed when a peptide is administered via a parenteral administration route. Without being bound by this theory, it is assumed that the peptides of the present invention stabilize RyR sarcoplasmic reticulum calcium release channels in their closed conformation, and thereby reduces calcium leakage from these channels (Most et al., 2006, Circulation 114:1258-1268; Voelkers M. et al., 2007, Cell Calcium 41:135-143). In a particularly preferred embodiment, the peptides of the present invention exhibit anti-arrhythmic potential and prevents and/or reduces calcium leakage as described above.

In another preferred embodiment, the peptides of the present invention exhibit the ability of restoring hemodynamic function in vivo. Preferably, the peptides of the present invention restore hemodynamic function in an individual suffering from heart failure such as during or after myocardial infarction. Preferably, this effect is observed when a peptide is administered via a parenteral administration route. The skilled person can readily test a peptide for this function, e.g., by using an experimental mouse heart failure model. For example, the skilled person may determine cardiac performance and survival rate in mice with postischemic contractile dysfunction with and without administration of the peptide. The peptide may be administered preferably parenterally, such as intraperitoneally, intravenously, or subcutaneously, daily or every second day for several days, such as 6, 7, 8, or 9 days, up to a few weeks, such as 2, 3, or 4 weeks, preferably 2 weeks. The left ventricular performance of the experimental animals may be assessed by serial echocardiography (Most et al., 2003, J. Bio. Chem. 278; 33809-33817; Most et al., 2006, Circulation 114:1258-1268). Preferably, the peptides of the present invention exhibit anti-arrhythmic potency and the ability of restoring hemodynamic function in vivo.

In another preferred embodiment, the peptides of the present invention enhance the isometric and/or tetanic twitch force in skeletal muscle tissue, such as skeletal muscle fibers. Preferably, the peptides of the present invention exhibit this effect in vitro and in vivo. Preferably, this in vivo effect is observed when a peptide is administered via a parenteral administration route. The skilled person can readily assess this function for a given peptide, for example, by isometric tension measurement in peptide treated and untreated intact muscles or muscle fibers, e.g., intact extensor digitorum longum skeletal muscles, isolated from an experimental animal. For example, the isolated muscle may be incubated for a certain period of time, such as 30 to 60 minutes, preferably 45 minutes, with the peptide at different concentrations, for example at a concentration in the range of 500 nM to 4 µM, preferably at a concentration of 1 µM. The isolated muscle may then be stimulated with a tetanic train, for example, applied at 125 Hz for 175 ms and the isometric tension may be measured (Weisleder et al., 2006, J. Cell Biol. 174:639-654). Preferably, the enhancing effect on isometric and/or tetanic twitch force is also observed for muscle fibers isolated from an experimental animal which was treated systemically with the peptide, wherein preferably the peptide was administered parenterally. Thus, in a preferred embodiment, the peptides of the present invention attenuate skeletal muscle dysfunction and enhance contractile performance in skeletal muscle cells in vivo when administered systemically, preferably parenterally, such as intraperitoneally, intravenously, or subcutaneously. In a particularly preferred embodiment, the peptides of the present invention exhibit the ability to enhance isometric and tetanic twitch force in skeletal muscle cells, the ability to increase contractile performance in cardiomyocytes, and the anti-arrhythmic potential described above.

In a particularly preferred embodiment, the peptides of the present invention exhibit one or more, e.g. 1, 2, 3, 4, or 5, preferably all of the above functions, i.e., anti-arrhythmic potential, anti-apoptotic potential, the ability to reduce calcium spark frequency, the ability to prevent and/or reduce calcium leakage from the sarcoplasmic reticulum, the ability to restore hemodynamic function preferably in an individual suffering from heart failure, and the ability to enhance isometric and/or tetanic twitch force in skeletal muscle cells and/or fibers. Preferably, said functions can be observed in vitro and in vivo. Preferably, said in vivo effects can be observed when the peptide is administered via a parenteral administration route.

The skilled person is well aware of methods for producing peptides according to the present invention. For example, the peptide may be chemically synthesized, e.g., by liquid phase or solid phase peptide synthesis, or the peptide may be genetically engineered using recombinant DNA techniques and a cellular expression system, such as bacteria (e.g., *Escherichia coli*), yeast cells, insect cells, mammalian cells etc, or an in vitro expression system.

In a third aspect, the present invention provides the peptide according to the first or second aspect of the present invention for medical use.

In a fourth aspect, the present invention provides the peptide according to the first or second aspect of the present invention for therapeutic use for treating and/or preventing a disorder associated with muscular malfunction, e.g., a myopathy. Preferably, said disorder is a cardiac and/or skeletal muscle disorder. The disorder may be acquired or congenital. In this context, the term "acquired" means that the medical condition, i.e., the disorder, developed postfetally. Such an acquired disorder in the context of the present invention may be a myocardial infarction. An example for an acquired skeletal muscle disorder is myositis. Congenital disorders involve defects to a developing fetus which may be the result of genetic abnormalities, errors of morphogenesis, or chromosomal abnormalities. Genetic diseases or disorders are all congenital, though they may not be expressed or recognized until later in life. Congenital disorders in the context of the present invention are, for example, Nemaline myopathy, Myotubular myopathy, or Centronuclear myopathy. Furthermore, in the context of the present invention, the cardiac or skeletal muscle disorder may be acute or chronic. For example, an acute cardiac muscle disorder is acute heart failure, an acute skeletal muscle disorder is Rhabdomyolysis. A chronic skeletal muscle disorder is, for example, Dermatomyositis. A chronic cardiac muscle disease is, for example, chronic heart failure.

In a preferred embodiment of the fourth aspect of the present invention, the muscular malfunction is associated with defective calcium cycling and/or defective contractile performance in muscle cells, preferably in skeletal muscle cells or cardiomyocytes. Preferably, the peptide is for enhancing and/or restoring calcium cycling and/or for enhancing and/or restoring contractile performance in muscle cells. Defective calcium cycling in myocytes may be a result of reduced calcium content in the sarcoplasmic reticulum, reduced release of calcium from the sarcoplasmic reticulum during excitation-contraction coupling, calcium leakage from the sarcoplasmic reticulum, for example, due to a leaky RyR sarcoplasmic reticulum calcium release channel, increased calcium spark frequency, or reduced or slowed re-uptake of calcium into the sarcoplasmic reticulum and/or the mitochondria after contraction, for example, due to a malfunctioning or non-functioning sarcoplasmic/endoplasmic reticulum calcium ATPase (SERCA). Without being bound to this theory, it is assumed that a defective calcium cycling is one of the major reasons for defective contractile performance, e.g., contractile dysfunction, of muscle cells. Thus, it is assumed that enhancing or restoring calcium cycling also enhances and/or restores contractile performance. Almost all cardiac and skeletal muscle disorders/diseases are a result of contractile dysfunction of the respective muscle cells. For example, in cardiac arrhythmias, the cardiac muscle contraction is not precisely timed. This may have lethal consequences. In most of the skeletal muscle disorders, the contractile performance is reduced which has the consequence of muscle weakness such as in various types of dystrophies. It is assumed that the peptide according to the first aspect of the present invention is capable of enhancing and/or restoring calcium cycling in myocytes, and thereby, enhances and/or restores contractile performance. However, it is emphasized that the peptides of the present invention are not only suitable for treating disorder associated with muscular malfunction, wherein the muscular malfunction is associated with defective calcium cycling, but also muscular diseases which are not based on malfunctioning calcium handling. In these diseases the peptide of the present invention may relief the symptoms such as muscle weakness.

In a preferred embodiment of the third and fourth aspect of the present invention, the peptide is for protecting myocytes, preferably skeletal muscle cells and/or cardiomyocytes, more preferably heart tissue from arrhythmias, preferably from catecholamine triggered arrhythmias, preferably for protecting an individual from ventricular arrhythmias, preferably from lethal ventricular tachyarrhythmias, and thus, preferably from sudden cardiac death. Preferably, said function is exhibited in vivo, preferably when the peptide is applied parenterally without the need for gene therapy.

In a further preferred embodiment of the third and fourth aspect of the present invention, the peptide is for reducing calcium spark frequency in myocytes, preferably in skeletal muscle cells and/or cardiomyocytes, and/or for preventing and/or reducing calcium leakage from the sarcoplasmic reticulum of myocytes, preferably in skeletal muscle cells and/or cardiomyocytes. Preferably, said function is exhibited in vivo, preferably when the peptide is applied parenterally without the need for gene therapy.

In a further preferred embodiment of the third and fourth aspect of the present invention, the peptide is for preventing or reducing calcium leakage from the sarcoplasmic reticulum of muscle cells, preferably of skeletal muscle cells and/or cardiomyocytes. Preferably, the peptide is for preventing or reducing calcium leakage from the sarcoplasmic reticulum due to leaky RyR sarcoplasmic reticulum calcium release channels. Preferably, said function is exhibited in vivo, preferably when the peptide is applied parenterally without the need for gene therapy.

In another preferred embodiment of the third and fourth aspect of the present invention, the peptide is for protecting myocytes, preferably skeletal muscle cells and/or cardiomyocytes from apoptotic cell death, preferably from calcium-induced apoptotic cell death, preferably from sarcoplasmic reticulum calcium leakage triggered apoptotic cell death. Preferably, the peptide is for preventing apoptotic cell death in failing myocardium, i.e., protecting cardiomyocytes from apoptotic cell death in failing myocardium. Preferably, said function is exhibited in vivo, preferably when the peptide is applied parenterally without the need for gene therapy.

In another particularly preferred embodiment of the third and fourth aspect of the present invention, the peptide is for restoring and/or enhancing hemodynamic function, for example, cardiac performance such as contractile performance of cardiomyocytes, preferably the peptide is for restoring and/or enhancing hemodynamic function in an individual suffering or has suffered from heart failure such as from myocardial infarction. Preferably, said function is exhibited in vivo when the peptide is applied parenterally without the need for gene therapy.

In another preferred embodiment of the third and fourth aspect of the present invention, the peptide is for enhancing and/or restoring contractile performance in skeletal muscle cells, preferably for enhancing and/or restoring isometric and/or tetanic twitch force in skeletal muscle cells, preferably in skeletal muscle tissue. The isometric twitch force is tension development without muscle shortening, the tetanic twitch force is the maximal isometric force development, normally, when single contractions start to merge above 50 Hz stimulation. Preferably, said function is exhibited in vivo, preferably when the peptide is applied parenterally without the need for gene therapy.

It is emphasized that the disclosure on functional characteristics of specific embodiments of the peptides according to the present invention in the first or second aspect of the present invention also applies to the third and fourth aspects of the present invention.

In a preferred embodiment of the fourth aspect of the present invention, the cardiac muscle disorder is selected from the group consisting of postischemic contractile dysfunction, preferably postischemic contractile right and/or left ventricular dysfunction, congestive heart failure, preferably compensated and/or decompensated congestive heart failure, cardiogenic shock, septic shock, myocardial infarction, cardiomyopathy, dysfunction of heart valves, and ventricular disorder, such as acute or chronic right ventricular disorder.

In a preferred embodiment of the fourth aspect of the present invention, the skeletal muscle disorder is selected from the group consisting of muscular dystrophy, muscle weakness, muscular atrophy, myositis, central core disease, nemaline (rod) myopathy, centronuclear myopathy, myotubular myopathy, centronuclear myotubular myopathy, ophthalmoplegia of the eye, and mitochondrial myopathy. The muscular dystrophy may be selected from the group consisting of Becker's muscular dystrophy, congenital muscular dystrophy, Duchenne muscular dystrophy, distal muscular dystrophy, Emery-Dreifuss muscular dystrophy, facioscapulohumeral muscular dystrophy, Limb-girdle muscular dystrophy, myotonic muscular dystrophy, and oculopharyngeal muscular dystrophy. The myositis may be selected from the group consisting of myositis ossificans, fibromyositis, idiopathic inflammatory myopathies (such as dermatomyositis, polymyositis, and inclusion body myositis), and pyomyositis.

In a fifth aspect, the present invention provides a pharmaceutical composition comprising the peptide of the first or second aspect or a pharmaceutically acceptable salt thereof and a pharmaceutically acceptable excipient, carrier, and/or diluent.

The term "pharmaceutically acceptable salt" refers to a salt of the peptide of the present invention. Suitable pharmaceutically acceptable salts include acid addition salts which may, for example, be formed by mixing a solution of the peptide of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the peptide carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

In a preferred embodiment, the pharmaceutical composition of the present invention is for treating or preventing disorders associated with muscular malfunction as specified above for the peptides of the invention in the fourth aspect of the present invention.

In another preferred embodiment, the pharmaceutical composition of the present invention is for protecting myocytes from arrhythmias, protecting an individual from ventricular arrhythmias, preferably from lethal ventricular tachyarrhythmias, and thus, preferably from sudden cardiac death, for reducing calcium spark frequency in myocytes, for preventing and/or reducing calcium leakage from the sarcoplasmic reticulum of myocytes, for protecting myocytes from apoptotic cell death, preferably protecting cardiomyocytes from apoptotic cell death in failing myocardium, for restoring and/or enhancing hemodynamic function, preferably enhancing hemodynamic function in an individual suffering from heart failure, and/or for enhancing and/or restoring contractile performance in skeletal muscle cells, preferably for enhancing and/or restoring isometric and/or tetanic twitch force in skeletal muscle cells as described above for the peptides according to the present invention in the fourth aspect of the present invention.

The pharmaceutical composition contemplated by the present invention may be formulated in various ways well known to one of skill in the art. For example, the pharmaceutical composition of the present invention may be in liquid form such as in the form of solutions, emulsions, or suspensions. Preferably, the pharmaceutical composition of the present invention is formulated for parenteral administration, preferably for intravenous, intramuscular, subcutaneous, transdermal, intrapulmonary, intraperitoneal, intracardiac administration, or administration via mucous membranes, preferably for intravenous, subcutaneous, or intraperitoneal administration. Preferably, the pharmaceutical composition of the present invention is in the form of a sterile aqueous solution which may contain other substances, for example, enough salts or glucose to make the solution isotonic with blood. The aqueous solutions should be suitably buffered (preferably to a pH of from 3 to 9, more preferably to a pH of from 5 to 7), if necessary.

The pharmaceutical composition is preferably in unit dosage form. In such form the pharmaceutical composition is subdivided into unit doses containing appropriate quantities of the active component. The unit dosage form can be a packaged preparation, the package containing discrete quantities of pharmaceutical composition such as vials or ampoules.

In a sixth aspect, the present invention provides a use of the peptide according to the first or second aspect of the present invention for the preparation of a pharmaceutical composition for treating or preventing disorders associated with muscular malfunction, wherein said disorder is preferably as specified above in the fourth aspect of the present invention. In a preferred embodiment, the use of the peptide is for the preparation of a pharmaceutical composition for protecting myocytes from arrhythmias, protecting an individual from ventricular arrhythmias, preferably from lethal ventricular tachyarrhythmias, and thus, preferably from sudden cardiac death, for reducing calcium spark frequency in myocytes, for preventing and/or reducing calcium leakage from the sarcoplasmic reticulum of myocytes, for protecting myocytes from apoptotic cell death, preferably protecting cardiomyocytes from apoptotic cell death in failing myocardium, for restoring and/or enhancing hemodynamic function in an individual suffering from heart failure, and/or for enhancing and/or restoring contractile performance in skeletal muscle cells, preferably for enhancing and/or restoring isometric and/or tetanic twitch force in skeletal muscle cells as described above for the peptide according to the present invention in the fourth aspect of the present invention. In a preferred embodiment of the sixth aspect of the present invention, the use is for the preparation of a pharmaceutical composition for ameliorating a disease condition associated with a muscular disorder, preferably a skeletal muscle disorder and/or a cardiac muscle disorder, wherein the term "ameliorating a disease condition" is as defined for the seventh aspect of the present invention.

In a seventh aspect, the present invention provides a method for treating or preventing disorders associated with muscular malfunction comprising administering to an individual in need thereof the peptide of the first or second aspect of the present invention or the pharmaceutical composition of the fifth aspect of the present invention in an amount sufficient to ameliorate the disease condition of said individual, preferably the patient. In this context, "ameliorating the disease condition" means, for example, that the individual has a subjective sensation of improvement after a certain period of time after the peptide or the pharmaceutical composition has been administered to the patient, or that the function of the diseased muscle has been measurably improved after treatment with the peptide or the pharmaceutical composition of the present invention. For example, if the contractile performance such as the contractile force of a muscular tissue, e.g. a diseased heart muscle or a diseased skeletal muscle, deviated from an average normal contractile function by 50%, the disease condition is ameliorated by the treatment if, after the treatment, the contractile performance of said musclular tissue deviates less than 50%, e.g. less than 40%, less than 30%, less than 20%, less than 10%, or not at all, from the average normal contractile function of a corresponding healthy muscular tissue. The contractile performance may also be improved compared to the average cardiac performance of a healthy cardiac tissue. The term "individual in need thereof" preferably refers to an animal patient, more preferably to a mammalian patient, most preferably to a human patient as defined above.

The disorder associated with muscular malfunction is preferably as defined for the fourth aspect of the present invention.

In a preferred embodiment, the method according to the seventh aspect of the present invention is for protecting myocytes from arrhythmias, protecting an individual from ventricular arrhythmias, preferably from lethal ventricular tachyarrhythmias, and thus, preferably from sudden cardiac death, for reducing calcium spark frequency in myocytes, for preventing and/or reducing calcium leakage from the sarcoplasmic reticulum of myocytes, for protecting myocytes from apoptotic cell death, preferably protecting cardiomyocytes from apoptotic cell death in failing myocardium, for restoring and/or enhancing hemodynamic function in an individual suffering from heart failure, and/or for enhancing and/or restoring contractile performance in skeletal muscle cells, preferably for enhancing and/or restoring isometric and/or tetanic twitch force in skeletal muscle cells as described above for the peptide according to the present invention in the fourth aspect of the present invention.

For treating or preventing a disorder associated with muscular malfunction as specified in the sixth and seventh aspect of the present invention, the peptide or the pharmaceutical composition according to the present invention can be administered to an animal patient, preferably a mammalian patient, preferably a human patient, preferably via a parenteral administration route, for example, intravenously, intramuscularly, subcutaneously, transdermally, intrapulmonary, intraperitoneally, intracardiacally, or via mucous membranes, preferably intravenously, subcutaneously, or intraperitoneally. Administration may be by infusion or classical injection, for example, using cannulas, or by needleless injection techniques.

In an eighth aspect, the present invention provides a composition comprising or consisting of the peptide according to the first or second aspect of the present invention in combination with another medicament usually administered for treating or preventing diseases associated with muscular malfunction, preferably skeletal muscle diseases, more preferably cardiac muscle diseases. Preferably, said composition is a pharmaceutical composition which may also comprise one or more pharmaceutically acceptable diluent(s), carrier(s), and/or excipient(s). In a preferred embodiment, said medicament exhibits pro-arrhythmogenic potential, preferably on cardiomyocytes. In a preferred embodiment of this aspect of the present invention, the peptides according to the present invention reduce the pro-arrhythmogenic potential of said medicament. Preferably, said medicament is a catecholamine, e.g., a direct β-mimetics such as endogenous or synthetic catecholamine or an indirect β-mimetics such as a phosphodiesterase inhibitor β-mimetics or another agent enhancing RyR2 calcium-sensitivity such as caffeine or similar chemicals, e.g., purine alkaloids or dimethylxanthines. In a preferred embodiment of the eigth aspect of the present invention, said medicament is selected form the group consisting of a catecholamine, a β-adrenergic receptor agonist, and a β-adrenergic receptor blocker. In one embodiment, said medicament is a catecholamine such as dobutamine, noradrenaline, adrenaline, dopamine, or isoprenalin, preferably dobutamine, noradrenaline, or adrenaline. In another embodiment, said medicament is a β-adrenergic receptor agonist such as isoproterenol, salbutamol, fenoterol, formoterol, metaproterenol, salmeterol, terbutaline, clenbuterol, arbutamine, befunolol, bromoacetylalprenololmenthane, broxaterol, cimaterol, cirazoline, denopamine, epinephrine, etilefrine, hexoprenaline, higenamine, isoetharine, isoxsuprine, mabuterol, methoxyphenamine, nylidrin, oxyfedrine, pirbuterol, prenalterol, procaterol, ractopamine, reproterol, rimiterol, ritodrine, tretoquinol, tolubuterol, xamoterol, zilpaterol, or zinterol, preferably isoproterenol, salbutamol, fenoterol, formoterol, metaproterenol, salmeterol, terbutaline, clenbuterol, more preferably isoproterenol. In another embodiment, said medicament is a β-adrenergic receptor blocker such as metoprolol, atenolol, bisoprolol, nebivolol, esmolol, betaxolol, acebutolol, celiprolol, bupranolol, propranolol, timolol, carvedilol, sotalol, pindolol, oxprenolol, or alprenolol, preferably metoprolol, atenolol, bisoprolol, nebivolol, esmolol, or betaxolol, most preferably metoprolol. The composition according to the eigth aspect of the invention may comprise one or more, e.g., 1, 2, 3, or 4 different medicaments either of the same category or of different categories, in combination with the peptide according to the first or second aspect of the present invention.

The present inventors have surprisingly found that the shortened peptides according to the present invention are functional despite their significantly reduced size, i.e. useful for treating or preventing disorders associated with muscular malfunction as specified throughout the description, that the peptides according to the present invention have the ability to reduce the pro-arrhythmogenic potential of medicaments such as catecholamines, β-adrenergic receptor agonists, or 1i-adrenergic receptor blocker without counteracting their beneficial effects, and that these therapeutic effects of said peptides are exerted even if the peptides are administered parenterally, preferably via an intravenous, intraperitoneal, or subcutaneous administration route, without the need for genetic modification by gene therapy and without causing major side effects.

EXAMPLES

The Examples are designed in order to further illustrate the present invention and serve a better understanding. They are not to be construed as limiting the scope of the invention in any way.

Example 1

Inotropic Effects of S100A1 Protein and S100A1 C-Terminal 20-mer Peptide on Permeabilized Cardiomyocytes and Skeletal Muscle Fibers Adult ventricular rabbit cardiomyocytes were isolated from four different animals as previously described (Loughrey C. M. et al., 2004, J. Physiol. 556:919-934) and permeabilized using β-escin (0.1 mg/ml). The permeabilized cells were incubated for 1 minute with rhodamine-labeled human S100A1 protein (0.1 μM) or FITC-labeled S100A1 C-terminal 20-mer peptide (0.1 μM) fused to a hydrophilic element (i.e. amino acids 75 to 94 of human S100A1 fused to the hydrophilic element D-K-D-D-P-P (SEQ ID NO: 17)). Cells were monitored using a Bio-Rad 2000 laser scanning confocal microscope (LSCM). A striated staining pattern can be observed that resembles the ryanodine staining pattern (FIG. 4).

Furthermore, $Ca^{2+}$-spark frequency has been assessed in the permeabilized cells treated with S100A1 protein or the S100A1 C-terminal 20-mer peptide fused to a hydrophilic element and it was shown that both, the full-length protein as well as the C-terminal fragment, decrease calcium spark frequency in permeabilized cardiomyocytes (FIGS. 5 and 6). Isolated cardiomyocytes were perfused with a mock intracellular solution and permeabilized using B-escin (0.1 mg/ml). Fluo-3 free acid (10 μM) present in the perfusing solution was excited at 488 nm (Kr-laser) and measured at >515 nm applying epifluorescence optics of an inverted microscope with a ×60-1.2 NA water-immersion objective lens. Fluorescence was acquired in line scan mode at 2 ms $line^{-1}$; pixel dimension was 0.3 μm (512 pixels $scan^{-1}$; zoom=1.4). The scanning laser line orientated parallel with the long axis and placed approximately equidistant between the outer edge of the cell and the nucleus/nuclei, to ensure the nuclear area was not included in the scan line. To enable this trace to be converted to free calcium concentration ($[Ca^{2+}]$) a series of calibration solutions were used at the end of each $Ca^{2+}$-spark measurement period incorporating 10 mM EGTA. In all experiments concerning $Ca^{2+}$-sparks, the $[Ca^{2+}]$ in the test solution was 145-160 nM. $Ca^{2+}$-sparks recorded in Fluo-3-containing solutions were quantified using an automated detection and measurement algorithm.

All $Ca^{2+}$-spark measurements were made within 7-8 min of cell permeabilization. This time was standardized to minimize loss of soluble proteins. S100A1 protein or S100A1-ct peptide was applied in mock solution using a gravity-fed perfusion system. Effects were compared to permeabilized control cardiomyocytes perfused with mock-solution without addition of S100A1. Up to four different cells from each animal were used for $Ca^{2+}$-spark measurements.

Muscle Fiber Preparation and Experimental Solutions. All of the animals were handled according to the guidelines of the animal care committee of the University of Heidelberg. Male BALB/c mice (3-6-months-old) were sacrificed by an overdose of carbon dioxide, and muscle fiber preparation was carried out as previously described (Fink R. H. and Stephenson D. G., 1987, Pflugers Arch. Eur. J. Physiol. 409:374-380; Makabe M. et al., 1996, Pflugers Arch. Eur. J. Physiol. 432: 717-726). Either EDL (M. ext. dig. longum) or Soleus was isolated, and a small fiber bundle containing two to four single fibers (between 80 and 150 μm in diameter and 3-4-mm-long) was dissected in paraffin oil. The fiber preparation was glued between a force transducer pin (AE801, Senso-Noras, Horton, Norway) and a micrometer-adjustable screw. All of the experiments were carried out at room temperature (23-25° C.). All of the solutions were adjusted to pH 7.0. The free ion concentrations were calculated with the computer program REACT (version 2.0) from G. L. Smith (Glasgow, Scotland). Table I shows the concentrations of the solution used in the experiments.

TABLE I

Total concentration, in brackets is free concentration

| | LR | HR | HA | SK | LS |
|---|---|---|---|---|---|
| ATP (mM) | 8 | 8 | 8 | 8 | 8 |
| CP (mM) | 10 | 10 | 10 | 10 | 10 |
| CK (unit/ml) | 150 | 150 | 150 | 150 | 150 |
| $Ca^{2+}$ (mM) | | 0.01 | 49.5 | | [4 × $10^{-4}$] |
| $Mg^{2+}$ (mM) | [0.5] | [0.5] | [0.5] | [0.5] | [0.5] |
| $Na^+$ (mM) | 36 | 36 | 36 | 36 | 36 |
| $K^+$ (mM) | 117 | 117 | 117 | 117 | 117 |
| HEPES (mM) | 60 | 60 | 60 | 60 | 60 |
| EGTA (mM) | 0.5 | 50 | 50 | 0.5 | 50 |
| HDTA (mM) | 49.5 | | | 49.5 | |
| Saponin (mg/ml) | | | | 50 | |

LR, low relaxing solution; HR, high relaxing solution; HA, high activation solution; SK, skinning solution; LS, loading solution.

The high relaxation and the high activation solution contained 50 mM EGTA to buffer free $Ca^{2+}$, whereas the low relaxing solution contained 0.5 mM EGTA and 49.5 mM 1,6-diamino hexane-N,N,N,N-tetraacetic acid (HDTA), which in contrast to EGTA has very low affinity to $Ca^{2+}$. The skinning solution is obtained by the addition of 50 μg/ml saponin to the low relaxing solution. The release solution consisted of the low relaxing solution with 5 mM caffeine added. Loading solution contained 50 mM EGTA to clamp free $Ca^{2+}$ to 0.4 μM (pCa 6.4). The solutions to measure the pCa-force relation were obtained by mixing high relaxing solution with appropriate amounts of high activating solution, and 5 mM caffeine added. All of the experiments were recorded using a strip chart recorder and were simultaneously digitally converted with an Axon Instruments Digidata 1200 board and interface (using the Axotape Software, version 2.0). For muscle fiber preparation and force measurements see also Weisleder N. et al., 2006, J. Cell Biol. 174:639-645.

Assessment of $Ca^{2+}$-Induced Isometric Twitch Force and $Ca^{2+}$ Transients in Skeletal Muscle Fibers.

It was shown that both, the full-length S100A1 protein as well as the C-terminal fragment, has a potency to enhance isometric twitch force in permeabilized murine skeletal muscle fibers (FIG. 7). Muscle fibers were skinned for 5 min in skinning solution while the sarcomere length was adjusted to 2.6±0.1 μm using the diffraction pattern of a helium-neon laser. Before loading the SR with the loading solution (pCa 6.4) for 1 min, the fibers were shortly immersed in release solution and high relaxing solution and then equilibrated for 2 min in low relaxing solution. Subsequently, the preparation was dipped for 1 s into the high relaxing solution and again for 2 min in low relaxing solution. The fibers were exposed to the release solution containing 5 mM caffeine until the initial force transient returned to the resting force level. Maximum force was measured in the high activating solution at pCa 4.28 and 5 mM caffeine. The fibers then were relaxed in high relaxing solution for 1 min to buffer $Ca^{2+}$. Several control transients were recorded before the fiber was exposed to the S100A1 protein or the S100A1 peptide mixture (N/H/C) or the C-terminal 20-mer alone, and the experiment was repeated as outlined above. S100A1 protein or peptides were added to the low relaxing solution before and during release and to the high activating solution. The pCa-force relation in response to S100A1 interventions (0.001-10 μM) was measured with six different $Ca^{2+}$ concentrations (EDL, pCa 9.07, 5.91, 5.72, 5.49, 5.17, and 4.28), each containing 5 mM caffeine. The EC50 and the Hill coefficient were obtained from a Hilltype fit. The EC50 value indicates the $Ca^{2+}$ concentration needed for half-maximal isometric force activation, which is as a measure of $Ca^{2+}$ sensitivity of the contractile apparatus. The Hill coefficient gives an indication of the maximum steepness of the sigmoidal curve. The correlation coefficients were calculated to determine the accuracy of the fit. The force transient was transformed into the corresponding free $Ca^{2+}$ transient by using the individual $pCa^{2+}$ force relation as a $Ca^{2+}$ indicator and reversing each point of the force transients into the corresponding free $Ca^{2+}$ level as previously described. Based on the fact that sensitivity of the $Ca^{2+}$-regulatory proteins and the corresponding force development directly provide a measure of the free myofibrillar $Ca^{2+}$, the pCa force relation relates free $Ca^{2+}$ and force. Thus, the pCa-force relation can be used as a bioassay, which converts the rather slow force transients from the $Ca^{2+}$ release from the SR into apparent $Ca^{2+}$ transients.

Example 2

Cell-Permeability of the S100A1ct$_{6/11}$ Peptide

Neither rhodamine-labeled S100A1 protein nor the FITC-labeled S100A1 C-terminal 20-mer peptide with or without a hydrophilic motif such as D-K-D-D-P-P (SEQ ID NO: 17) are able to penetrate the cell membrane of adult intact cardiomyocytes. However, the present inventors surprisingly found that a peptide having the sequence D-K-D-D-P-P-Y-V-V-L-V-A-A-L-T-V-A (SEQ ID NO: 42) referred to as S100A1ct$_{6/11}$ is cell permeable. FITC-labeled S100A-1ct$_{6/11}$ was incubated with intact rat ventricular cardiomyocytes for 15 minutes before the cells were monitored using confocal laser scanning microscopy. Endogenous S100A1 protein was stained using a conventional immunofluorescence protocol. The intracellular staining pattern of FITC-labeled S100A1ct$_{6/11}$ resembles that of endogenous S100A1 (FIG. 8).

Example 3

Functional Characterization of the S100A1ct$_{6/11}$ Peptide in Cardiomyocytes

All experiments performed for the functional characterization of the S100A1ct$_{6/11}$ peptide were performed on intact, i.e., non-permeabilized cardiomyocates. It was shown that the S100A1ct$_{6/11}$ peptide exerts positive inotropic effects on stimulated isolated ventricular cardiomyocytes (FIG. 9), while fragments thereof (FIG. 10) or corresponding peptides derived from the carboxy-terminus of S100A4 or S100B (FIG. 11) do not show this ability. Calcium transients were assessed in FURA2-AM field-stimulated cardiomyocytes employing epifluorescent digitalized microscopy and sarcoplasmic reticulum calcium load was determined (FIG. 12).

Calibration and Measurement of $Ca^{2+}$ Transients and SR $Ca^{2+}$ Load in Cardiomyocytes.

Intracellular $Ca^{2+}$ transients of mouse ventricular cardiomyocytes were calibrated and measured as previously described (Remppis A. et al., 2002, Basic Res. Cardiol. 97: I/56-I/62). Briefly, isolated cells were washed in HEPES-modified medium 199 (M199) (Sigma), incubated in 1 ml of M199 (2 mM $[Ca^{2+}]_e$) with 2 μM Fura2-AM for 20 min at room temperature. Calibration and fluorescence measurements were carried out using an inverse Olympus microscope (Ix70) with a UV filter connected to a monochromator (Polychrome II, T.I.L.L. Photonics GmbH, Germany). Cells were electrically stimulated with 1 Hz and excited at 340/380 nm. Fluorescence emission was detected at 510 nm, digitized, and analyzed with T.I.L.L.VISION software (v. 3.3). Baseline data from five consecutive steady-state transients were averaged for analysis of transient amplitude ($Ca^{2+}$ amplitude; (nM)), time to peak (ms), and time to 50% decline (ms). Calibration for Fura2-AM loaded mouse ventricular myocytes on 50 cells yielded a minimal ratio ($R_{min}$) of 0.38±0.05 and a maximal ratio ($R_{max}$) of 3.36±0.21, whereas β and Kd were estimated to amount to 5.21±0.24 and 236±29 nM, respectively. Free intracellular $Ca^{2+}$ concentration $[Ca^{2+}]i$ was calculated by the equation of Grynkiewicz et al. (Grynkiewicz G. et al., 1985, J. Biol. Chem. 260:3440-3450). $Ca^{2+}$ transients were investigated at baseline and throughout a stepwise increase of isoproterenol concentrations ($10^{-9}$-$10^{-5}$ M) under electrical stimulation at 1 Hz and 2 mM $[Ca^{2+}]_e$ in M199. SR $Ca^{2+}$ load was assessed using a standard caffeine pulse protocol. After 2 min of electrical stimulation (1 Hz), myocytes were abruptly exposed to 0 $Na^+$/0 $Ca^{2+}$ solution with caffeine (1 0 mM). The peak of the caffeine-induced $Ca^{2+}$ transient was used as an index of the SR $Ca^{2+}$ load.

Myocyte Contractile Parameters.

Contractility studies of isolated ventricular myocytes were performed as recently described (Most P. et al., 2001, Proc. Natl. Acad. Sci. U.S.A. 98:13889-13894) with a video-edge detection system (Crescent Electronics, Sandy, Utah). In brief, myocytes were electrically stimulated to contract at 1 Hz in M199 at room temperature; edge detection measurements were obtained under basal condition and incremental isoproterenol concentrations ($10^{-9}$-$10^{-5}$ M). Data from five consecutive steady-state twitches were averaged for analysis of fractional cellular shortening (% CS (%)), shortening velocity (−dL/dt, (μm/s)) and relengthening velocity (+dL/dt, (μm/s)).

Example 4

S100A1ct$_{6/11}$ does not Alter β-Adrenergic Receptor Signaling and Protects Cardiomyocytes from Pro-Arrhythmic Store-Overload-Induced Calcium Release (SOICR)

The inotropic effect of S100A1ct$_{6/11}$ is additive to and independent of β-adrenergic stimulation (FIG. 13). Ventricular cardiomyocytes have been isolated as described above and the calcium transient amplitude has been assessed in presence and absence of isoproterenol and in presence or absence of the S100A1ct$_{6/11}$ peptide, respectively. Furthermore, the S100A1ct$_{6/11}$ peptide protects cardiomyocytes from pro-arrhythmic store-overload-induced calcium release (SOICR) (FIG. 15). Calcium sparks were assessed in Fluo-3 AM loaded cardiomyocytes under control and βAR ($10^{-7}$ M Isoproterenol+0.5 mM caffeine) as described in Ventucci et al., 2007, Circ. Res. 100:105-111). It is important to note that the protective effect of S100A1ct$_{6/11}$ is effective at concentrations (100 and 1000 nM) that exert inotropic actions in cardiomyocytes due to enhanced SR calcium load. Thus, despite its own enhancing effect on SR Ca resequestration, S100A1ct$_{6/11}$ effectively antagonizes βAR-triggered SOICR highlighting the unique molecular profile combining inotropic actions with anti-arrhythmic potency.

Example 5

Functional Characterization of the S100A1ct$_{6/11}$ Peptide in Normal and Disease Hearts The S100A1ct$_{6/11}$ peptide exerts significant in vivo hemodynamic effects resulting in enhanced contractile performance under basal and βAR-stimulated conditions (FIG. 18). These hemodynamic effects are effective in response to the β1AR-blocker metoprolol (FIGS. 19 and 20). Furthermore, the S100A1ct$_{6/11}$ peptide exerts significant therapeutic effects in vivo restoring hemodynamic function in an experimental heart failure mouse model (FIG. 21) and preventing apoptotic cell death in failing myocardium in said mouse model (FIG. 22). Furthermore, the S100A1ct$_{6/11}$ peptide protects the heart failure mice from βAR-triggered lethal ventricular tachyarrhythmias (FIG. 22).

Transthoracic Echocardiography.

Two-dimensional guided M-mode and Doppler echocardiography was carried out using an HDI 5000 echocardiograph (ATL, Bothell, Wash.) in conscious mice as previously described (Kohout et al., 2001, Circulation 104:2485-2491). Three independent echocardiographic measurements were taken in both modes. Left ventricular chamber diameter in endsystole (LVESD) and end-diastole (LVEDD), interventricular septum (IVSth), LV posterior (LVPth) wall thickness in end-diastole, and LV fractional shortening (FS %) were determined in a short-axis M-modeview at the level of the papillary muscles; FS %=LVEDD−LVESD/LVEDD×100; (%). LV ejection time (LVET) and heart rate (bpm) taken from aortic valve Doppler measurements were used to assess heart rate corrected mean velocity of circumferential fiber shortening: mean Vcfc=FS %/ET×√60/bpm×10; (circ/s).

Cardiac Catheterization and Hemodynamic Assessment.

Transthoracic two-dimensional echocardiography (TTE) in lightly anesthesized mice (tribromoethanol/amylene hydrate; Avertin; 2.5% wt/vol, 8 μl/g IP) with spontaneous respiration was performed with a 12-MHz probe both in sham and infarcted mice (TTE in M-mode was carried out in the parasternal short axis before and after (7 and 28 days) surgical procedure to assess LV diameter and subsequently fractional shortening (FS %=[(LVEDD−LVESD)/LVEDD)×100]). Under the same anesthesia, a 1.4 French micromanometer-tipped catheter (SPC-320, Millar instruments, Inc.) was inserted into the right carotid artery and then advanced into the LV. Hemodynamic analysis, including heart rate (beats/min$^{-1}$), LV end-diastolic pressure (LVEDP) and maximal (LV+dp/dt$_{max}$) and minimal (LV dp/dt$_{min}$) first derivate of LV pressure Myocardial Histopathology and Apoptosis LV tissue was cryosectioned (5 μm) and stained with hematoxylin-eosin (HE) to measure myocyte width in the remote, non-infarcted area of the LV, and measures were obtained at the level of the nucleus in longitudinally sectioned myocytes using NIH image software (ImageJ 1.34; http:/rsb.info.nih.gov/ij). Terminal deoxy-nucleotidyl transferase-mediated dUTP nick end-labeling (TUNEL) staining was carried out according to the manufacturers protocol (Roche, 11684795001). The number of TUNEL-positive cardiac myocyte nuclei in the remote area were counted a IX 70 inverse Olympus microscope (T.I.L.L. Vision software, version 3.3) and normalized per $10^5$ total nuclei identified by HE staining in the same section. To identify cells or bodies of cardiac origin, the sections were double stained with a cardiac specific anti-troponin C antibody (Santa Cruz, sc-8117, 1:50 dilution) and a corresponding pair of donkey anti-goat Alexa Fluor 568 (Molecular Probes, 1:100) (data not shown). Caspase 3 activity in myocardial tissue was measured using a Caspase-Glo assay kit (Promega). Briefly, the proluminescent substrate is cleaved by caspase-3. After caspase cleavage, a substrate for luciferase (aminoluciferin) is released resulting in the luciferase reaction and the production of luminescent signal. Cytosolic extracts from heart tissue were prepared by homogenization in hypotonic extraction buffer (25 mM HEPES, pH 7.5, 5 mM MgCl$_2$, 1 mM EGTA) containing protease inhibitor mix (1 tablet/5 ml) (Roche; Mini complete EDTA free protease inhibitor) and subsequently centrifuged (15 min, 13.000 rpm, 4° C.). The protein concentration of the supernatant was adjusted to 1 mg/ml with extraction buffer and stored at −80° C. An equal volume of reagents and 10 μg/ml cytosolic protein were added to a white-walled 96-well plate and incubated at room temperature for 1 h. The luminescence of each sample was measured in triplicates in a plate-reading luminometer.

The pro-arrhythmic protocol was adapted from the previously published protocol by Wayne Chen and co-workers (Xiao et al., 2007, J. Biol. Chem. 282:34828-34838).

Example 6

Functional Characterization of the S100A1ct$_{6,11}$ Peptide in Normal and Skeletal Muscle The S100A1ct$_{6/11}$ peptide significantly enhances isometric twitch force in normal and diseased skeletal muscle (FIG. 24). The protocol used for assessing isometric twitch force in skeletal muscle fibers is described in Example 1. For the experiment S100A1ct$_{6/11}$ peptide, intact (non-permeabilized) extensor digitorum longum (EDL) skeletal muscles fibers have been used. The twitch force of the isolated muscle fibers were enhanced upon S100A1ct$_{6/11}$ treatment, irrespective of whether the peptide was incubated with the isolated muscle fiber (FIG. 24A) or whether the peptide was administered systemically before the muscle fiber was isolated (FIG. 24B).

Example 7

The Inotropic Effect of the S100A1ct$_{6/11}$ Peptide is also Exerted by a Shorter Peptide A peptide consisting of amino acids 76 to 85 of human S100A1 fused to a hydrophilic element (D-K-D-D-P-P, SEQ ID NO: 17) exerts the same inotropic function as the S100A1ct$_{6/11}$ peptide (FIG. 25). The protocol for assessing the calcium transient amplitude is described above. The hydrophobic element alone, the vehicle alone, or amino-terminal deletion peptides lacking more than the amino acid 76 do not exhibit the inotropic effect. This experiment demonstrates that the tyrosine at position 76 is not essential for the inotropic function and cell permeability of the S100A1ct$_{6/11}$ peptide.

Example 8

Peptides encompassing a core motif of aa 79-82 of the primary human S100A1 protein sequence coupled to a 6-mer peptide (D-K-D-D-P-P) at their N-terminus fully mimic intracellular effects of the S100A1ct$_{6/11}$ peptide.

Rat ventricular cardiomyocytes were isolated and cultured employing standard procedures as previously published by the inventors (Most et al., J Clin Invest. 2004; 114(11):1550-63). Peptides dissolved in a mixture of 20 mM TRIS-HCL (pH 7.0) with 50% DMSO were added to FURA2-AM loaded cells 30 min before assessment of calcium transients. Measurement of field-stimulated calcium transients at 2 Hz were carried out and analyzed as described in detail by the inventors (Pleger and Most et al., Circulation. 2007 May 15;115(19):2506-15).

The invention claimed is:

1. A positive inotropic peptide comprising or consisting of a hydrophilic domain and a S100A1 protein derived domain, wherein said S100A1 protein derived domain consists of 4 to 9 consecutive amino acids of the inotropic motif:

$$\Phi^1\text{-}\Phi^2\text{-}\Phi^3\text{-}\Phi^4\text{-}X^5\text{-}\psi^6\text{-}L^7\text{-}[T/A]^8\text{-}\psi^9\text{-}\psi^{10} \text{ (SEQ ID NO :395)}$$

and comprises at least the core motif $\Phi^4\text{-}X^5\text{-}\psi^6\text{-}L^7$, wherein $\Phi$ and $\psi$ are in each instance independently selected from the group consisting of alanine, methionine, isoleucine, leucine, and valine, and X is any amino acid, wherein said peptide has a total length of minimally 10 amino acids and maximally 30 amino acids, and the peptide exhibits a positive inotropic action, and wherein said hydrophilic domain comprises or consists of the hydrophilic amino acid motif: $\Lambda_4\text{-}\Theta_2$, wherein $\Lambda$ is in each instance independently selected from aspartate, glutamate, lysine, and arginine and $\Theta$ is an α-helix interrupter is in each instance independently selected from proline or glycine.

2. A positive inotropic peptide comprising or consisting of an S100A1 protein derived domain, wherein said S100A1 protein derived domain consists of 7 to 9 consecutive amino acids of the inotropic motif:

$$\Phi^1\text{-}\Phi^2\text{-}\Phi^3\text{-}\Phi^4\text{-}X^5\text{-}\psi^6\text{-}L^7\text{-}[T/A]^8\text{-}\psi^9\text{-}\psi^{10} \text{ (SEQ ID NO :395)}$$

and comprises at least the core motif $\Phi^4\text{-}X^5\text{-}\psi^6\text{-}L^7$, wherein $\Phi$ and $\psi$ are in each instance an independently selected hydrophobic non-aromatic amino acid, and X is any amino acid, under the proviso that the N-terminal amino acid of said S100A protein derived domain consisting of 7 to 9 consecutive amino acids is $\Phi^1$, and wherein said peptide has a total length of maximally 100 amino acids.

3. The peptide of claim 1, further comprising one or more of the elements selected from the group consisting of a hydrophilic domain, a membrane penetration enhancing domain, one or more epitope-tag(s), and a peptide targeting domain.

4. The peptide of claim 1, wherein the C-terminus of said hydrophilic domain is directly or indirectly linked to the N-terminus of said inotropic domain and wherein the amino acid linked to said N-terminus is no hydrophobic non-aromatic amino acid.

5. The peptide of claim 1, wherein said hydrophilic domain comprises acidic, basic, and/or otherwise negatively or positively charged amino acids.

6. The peptide of claim 1, wherein said hydrophilic domain comprises or consists of the amino acid sequence:

(SEQ ID NO: 3)
[D/E]-[K/R]-[D/E]-[D/E]-[P/G]-[P/G].

7. The peptide of claim 1, wherein said hydrophilic domain comprises or consists of the amino acid sequence:

(SEQ ID NO: 17)
D-K-D-D-P-P.

8. The peptide of claim 3, wherein said membrane penetration enhancing domain comprises a membrane penetration enhancing domain derived from protein transduction domains or amphiphatic peptides.

9. The peptide of claim 3, wherein said membrane penetration enhancing domain comprises a membrane penetration enhancing domain derived from the HIV Tat peptide, the penetratin peptide, the transportan peptide, an MPG/Pep family member peptide, or arginine rich peptides.

10. The peptide of claim 1, wherein said core motif is:

(SEQ ID NO: 1)
[V/I/M]-[A/G/S]-[A/V]-L.

11. The peptide of claim 1, wherein said core motif is selected from the group consisting of the amino acid sequences V-G-A-L (SEQ ID NO: 4), I-A-A-L (SEQ ID NO: 5), V-S-V-L (SEQ ID NO: 6), M-G-A-L (SEQ ID NO: 7), V-A-A-L (SEQ ID NO: 8), and preferably is V-A-A-L (SEQ ID NO: 8).

12. The peptide of claim 1, wherein said inotropic motif is:

(SEQ ID NO: 2)
[V/I]-[V/I]-[L/M]-[V/I/M]-[A/G/S]-[A/V]-L-[T/A]-[V/A/I]-[A/M/V].

13. The peptide of claim 1, wherein said inotropic motif is selected from the group consisting of the amino acid sequences V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-V-L-I-A-A-L-A-A-A (SEQ ID NO: 13), V-I-L-V-S-V-L-T-V-A (SEQ ID NO: 14), I-I-L-M-G-A-L-T-V-A (SEQ ID NO: 15), and V-V-M-V-A-L-T-V-V (SEQ ID NO: 16).

14. The peptide of claim 1, wherein said S100A1 protein derived domain is selected from the group consisting of the amino acid sequences V-V-L-V-A-A-L-T-V (SEQ ID NO: 18), V-V-L-V-A-A-L-T (SEQ ID NO: 19), V-V-L-V-A-A-L (SEQ ID NO: 20), V-L-V-A-A-L-T-V-A (SEQ ID NO: 21), V-L-V-A-A-L-T-V (SEQ ID NO: 22), V-L-V-A-A-L-T (SEQ ID NO: 23), V-L-V-A-A-L (SEQ ID NO: 24), L-V-A-A-L-T-V-A (SEQ ID NO: 25), and L-V-A-A-L-T-V (SEQ ID NO: 26), L-V-A-A-L-T (SEQ ID NO: 27), L-V-A-A-L (SEQ ID NO: 28), V-A-A-L-T-V-A (SEQ ID NO: 29), V-A-A-L-T-V (SEQ ID NO: 30), V-A-A-L-T (SEQ ID NO: 31), and V-A-A-L (SEQ ID NO: 8).

15. The peptide of claim 1, wherein said peptide comprises or consists of an amino acid sequence selected from the group consisting of the amino acid sequences D-K-D-D-P-P-V-L-V-A-A-L-T-V-A (SEQ ID NO: 32), D-K-D-D-P-P-L-V-A-A-L-T-V-A (SEQ ID NO: 33), D-K-D-D-P-P-V-A-A-L-T-V-A (SEQ ID NO: 34), D-K-D-D-P-P-V-V-L-V-A-A-L-T-V (SEQ ID NO: 35), D-K-D-D-P-P-V-V-L-V-A-A-L-T (SEQ ID NO: 36), and D-K-D-D-P-P-V-V-L-V-A-A-L (SEQ ID NO: 37).

16. The peptide of claim 1, wherein said S100A1 protein derived domain is located at the C-terminus of said peptide.

17. The peptide of claim 1, wherein said peptide does not contain more than 9 continuous amino acids comprised in the 20 amino acid C-terminus region of an S100A1 protein.

18. The peptide of claim 1, further comprising one or more of the elements selected from the group consisting of a membrane penetration enhancing domain, one or more epitope-tag(s), and a peptide targeting domain.

19. The peptide of claim 1, further comprising a marker moiety.

20. The peptide of claim 1 or a pharmaceutical composition comprising the peptide of claim 1 and a pharmaceutically acceptable excipient, carrier, and/or diluent for use in treating acquired or congenital cardiac disorder or skeletal muscle disorders.

21. The peptide or pharmaceutical composition of claim 20, wherein the cardiac disorder is selected from the group consisting of postischemic contractile dysfunction, acute and chronic cardiac systolic and diastolic dysfunction congestive heart failure, impaired cell survival and enhanced electrical excitability, cardiogenic shock, septic shock, myocardial infarction, cardiomyopathy, dysfunction of heart valves, and ventricular disorder.

22. The peptide or pharmaceutical composition of claim 21, wherein the skeletal muscle disorder is selected from the group consisting of muscular dystrophy, heart failure associated skeletal muscle dysfunction, muscle weakness, muscular atrophy, myositis, central core disease, nemaline rod myopathy, centronuclear myotubular myopathy, ophthalmoplegia of the eye, and mitochondrial myopathy.

23. A pharmaceutical composition comprising the peptide of claim 1 and a pharmaceutically acceptable excipient, carrier, and/or diluent.

24. The pharmaceutical composition of claim 23, further comprising an active ingredient selected from the group consisting of catecholamines, β-adrenergic receptor agonists, and β-adrenergic receptor blockers.

25. The peptide of claim 1, wherein ψ is in each instance independently selected from the group consisting of alanine, methionine, isoleucine, and valine.

26. The peptide of claim 1, wherein Φ is in each instance independently selected from the group consisting of methionine, isoleucine, leucine, and valine.

27. A positive inotropic peptide comprising or consisting of an amino acid sequence selected from the group consisting of the amino acid sequences D-K-D-D-P-P-V-L-V-A-A-L-T-V-A (SEQ ID NO: 32), D-K-D-D-P-P-L-V-A-A-L-T-V-A (SEQ ID NO: 33), D- K-D-D-P-P-V-A-A-L-T-V-A (SEQ ID NO: 34), D-K-D-D-P-P-V-V-L-V-A-A-L-T-V SEQ ID NO: 35), D-K-D-D-P-P-V-V-L-V-A-A-L-T (SEQ ID NO: 36), and D-K-D-D-P-P-V-V-L-V-A-A-L (SEQ ID NO: 37).

\* \* \* \* \*